US007429571B2

(12) United States Patent
Chand et al.

(10) Patent No.: US 7,429,571 B2
(45) Date of Patent: Sep. 30, 2008

(54) THERAPEUTIC FUROPYRIMIDINES AND THIENOPYRIMIDINES

(75) Inventors: Pooran Chand, Birmingham, AL (US); Minwan Wu, Vestavia Hills, AL (US)

(73) Assignee: BioCryst Pharmaceuticals, Inc., Birmingham, AL (US)

( * ) Notice: Subject to any disclaimer, the term of this patent is extended or adjusted under 35 U.S.C. 154(b) by 262 days.

(21) Appl. No.: 11/332,858

(22) Filed: Jan. 16, 2006

(65) Prior Publication Data

US 2006/0165655 A1 Jul. 27, 2006

Related U.S. Application Data

(63) Continuation of application No. PCT/US2005/039072, filed on Oct. 28, 2005.

(60) Provisional application No. 60/728,215, filed on Oct. 19, 2005, provisional application No. 60/692,572, filed on Jun. 22, 2005, provisional application No. 60/665,832, filed on Mar. 29, 2005, provisional application No. 60/641,754, filed on Jan. 7, 2005, provisional application No. 60/623,065, filed on Oct. 29, 2004.

(51) Int. Cl.
*A01N 43/04* (2006.01)
*A61K 31/70* (2006.01)
*C07H 19/00* (2006.01)
*C07H 19/22* (2006.01)

(52) U.S. Cl. .............................. 514/48; 514/43; 514/45; 536/27.13

(58) Field of Classification Search ........................ None
See application file for complete search history.

(56) References Cited

U.S. PATENT DOCUMENTS

| 4,584,369 | A | 4/1986 | Klein et al. |
| 6,339,089 | B2 | 1/2002 | Nakashima et al. |
| 2006/0234963 | A1 | 10/2006 | Babu et al. |

FOREIGN PATENT DOCUMENTS

| EP | 0 071 227 | 2/1983 |
| WO | WO 97/29110 | 8/1997 |
| WO | WO 98/08847 | 3/1998 |
| WO | WO 98/49899 | 11/1998 |
| WO | WO 03/051899 | 6/2003 |
| WO | WO 03/093290 | 11/2003 |
| WO | WO 2004/058792 | 7/2004 |
| WO | WO 2005/123087 | 12/2005 |
| WO | WO 2006/050161 | 5/2006 |

OTHER PUBLICATIONS

De Clerq Nature Reviews: Microbiology (2004), vol. 2, pp. 704-720.*

Alexander et al., "(Acyloxy)alkyl carbamates as novel bioreversible prodrugs for amines: Increased permeation through biological membranes", *J Med Chem*, 31(2), 318-322 (1988).

Blight et al., "Efficient initiation of HCV RNA replication in cell culture", *Science*, 290, 1972-1974 (2000).

Bodor, "Soft drugs. 1. Labile quaternary ammonium salts as soft antimicrobials", *J Med Chem*, 23(5), 469-474 (1980).

Bruenn, "Relationships among the positive strand and double-strand RNA viruses as viewed through their RNA-dependent RNA polymerases", *Nucleic Acids Res*, 19(2), 217-226 (1991).

Davis, "Current therapy for chronic hepatitis C", *Gastroenterology*, 118, S104-S114 (2000).

Korba et al., "Use of a standardized cell culture assay to assess activities of nucleoside analogs against hepatitis B virus replication", *Antiviral Res*, 19(1), 55-70 (1992).

Lefebvre et al., "Mononucleoside phosphotriester derivatives with S-acyl-2-thioethyl bioreversible phosphate-protecting groups: Intracellular delivery of 3'-azido-2',3'-dideoxythymidine 5'-monophosphate", *J Med Chem*, 38(20), 3941-3950 (1995).

Okuse et al., "Enhancement of antiviral activity against hepatitis C virus in vitro by interferon combination therapy", *Antiviral Res*, 65(1), 23-34 (2005).

International Search Report for International Application No. PCT/US2006/010948, mailed Sep. 7, 2006.

Bhattacharya et al., "Studies on the Synthesis of Furo [3,2-d] Pyrimidine C-Nucleosides: New Inosine Analogues with Antiprotozoan Activity", *Nucleosides & Nucleotides*, 9(8), 1021-1043 (1990).

Bhattacharya et al., "Synthesis of Furo[3,2-d] Pyrimidine Nucleosides: A Novel C-Nucleoside Isostere of Adenosine", *Tetrahedron Letters*, 27(7), 815-818 (1986).

Ikegami et al, "Structure of Pyrrolosine: A Novel Inhibitor of RNA Synthesis, from the Actinomycete *Streptomyces albus*", *J. Am. Chem. Soc.*, 112, 9668-9669 (1990).

Jourdan et al., "Synthesis of Thieno[3,2-d] pyrimidine-2,4-diones Cyclic and Acyclic Nucleosides as Potential Anti HIV Agents", *J. Heterocyclic Chem.*, 31, 305-312 (1994).

Morris et al., "New Syntheses of 7-Substituted-2-aminothieno- and Furo[3,2-d] pyrimidines", *J. Heterocyclic Chem.*, 36, 423-427 (1999).

Otter et al., "A Corrected Structure for Pyrrolosine", *J. Am. Chem. Soc.*, 114, 668-671 (1992).

International Search Report for International Application No. PCT/US05/39072, mailed Oct. 17, 2007.

Girgis et al., *J. Med. Chem.*, 33, 2750-2755 (1990).

* cited by examiner

*Primary Examiner*—Patrick Lewis
(74) *Attorney, Agent, or Firm*—Viksnins, Harris & Padys PLLP

(57) ABSTRACT

The invention provides compounds of formula I, II, and III as described herein, as well as pharmaceutical compositions comprising the compounds, and synthetic methods and intermediates that are useful for preparing the compounds. The compounds of formula I, II, and III are useful as anti-viral agents and/or as anti-cancer agents.

16 Claims, No Drawings

THERAPEUTIC FUROPYRIMIDINES AND THIENOPYRIMIDINES

PRIORITY

This application is a continuation of international patent application No. PCT/US2005/039072, filed 28 Oct. 2005; this application also claims priority from U.S. Provisional Patent Application Nos. 60/623,065, filed Oct. 29, 2004; 60/641,754, filed Jan. 7, 2005; 60/665,832, filed Mar. 29, 2005; and 60/692,572, filed Jun. 22, 2005; and 60/728,215, filed Oct. 19, 2005.

BACKGROUND OF THE INVENTION

Viral diseases are a major cause of death and economic loss in the world. The Flaviviridae family of viruses consists of three genera: the flaviviruses (including dengue, West Nile, and yellow fever viruses), hepacivirus (HCV), and the pestiviruses (including bovine viral diarrhea virus, BVDV). The disease states and conditions caused by members of this family include yellow fever, dengue, Japanese encephalitis, St. Louis encephalitis, Hepatitis B and C, West Nile disease, and AIDS. Currently, human immunodeficiency virus (HIV), hepatitis B virus (HBV) and hepatitis C virus (HCV) infections are responsible for the largest number of viral related deaths worldwide. Although there are some drugs useful for treating HIV, there are only a few drugs useful for treating HBV, and no drugs that are broadly useful for treating HCV.

Ribavirin (1-β-D-ribofuranosyl-1-1,2,4-triazole-3-carboxamide) is a synthetic, non-interferon-inducing, broad spectrum antiviral nucleoside. Ribavirin is structurally similar to guanosine, and has in vitro activity against several DNA and RNA viruses including Flaviviridae (Davis. Gastroenterology 118:S104-S114, 2000). Ribavirin reduces serum amino transferase levels to normal in 40% of patients, but it does not lower serum levels of HCV-RNA (Davis. Gastroenterology 118:S104-S114, 2000). Thus, ribavirin alone is not effective in reducing viral RNA levels. Additionally, ribavirin has significant toxicity and is known to induce anemia.

Interferons (IFNs) are compounds which have been commercially available for the treatment of chronic hepatitis for nearly a decade. IFNs are glycoproteins produced by immune cells in response to viral infection. IFNs inhibit viral replication of many viruses, including HCV. When used as the sole treatment for hepatitis C infection, IFN suppresses serum HCV-RNA to undetectable levels. Additionally, IFN normalizes serum amino transferase levels. Unfortunately, the effects of IFN are temporary and a sustained response occurs in only 8%-9% of patients chronically infected with HCV (Davis. Gastroenterology 118:S104-S114, 2000).

HCV is a positive stranded ss RNA virus with a well characterized RNA-dependent RNA polymerase (RdRp) and a well characterized disease progression. HCV has infected an estimated 170 million people worldwide, leading to a major health crisis as a result of the disease. Indeed, during the next few years the number of deaths from HCV-related liver disease and hepatocellular carcinoma may overtake those caused by AIDS. Egypt is the hardest hit country in the world, with 23% of the population estimated to be carrying the virus; whereas, in the USA the prevalence of chronic infections has recently been determined to be around 1.87% (2.7 million persons). HCV infections become chronic in about 50% of cases. Of these, about 20% develop liver cirrhosis that can lead to liver failure, including hepatocellular carcinoma.

The NS5B region of HCV encodes a 65 KDa RdRp thought to be responsible for viral genome replication. RdRps function as the catalytic subunit of the viral replicase required for the replication of all positive-strand viruses. The NS5B protein has been well characterized, shown to possess the conserved GDD motif of RdRps and in vitro assay systems have been reported. Cellular localization studies revealed that NS5B is membrane-associated in the endoplasmic reticulum like NS5A, suggesting that those two proteins may remain associated with one another after proteolytic processing. Additional evidence suggests that NS3, NS4A and NS5B interact with each other to form a complex that functions as part of the replication machinery of HCV.

The X-ray crystal structure of NS5B apoenzyme has been determined and three very recent publications describe the unusual shape of the molecule. This unique shape for a polymerase, resembling a flat sphere, is attributed to extensive interactions between the fingers and thumb subdomains in such a way that the active site is completely encircled, forming a cavity 15 Å across and 20 Å deep. Modeling studies showed that the NS5B apoenzyme can accommodate the template-primer without large movement of the subdomains, suggesting that the structure is preserved during the polymerization reaction. The RdRp polypeptides from various members of the Flaviviridae family and other viral families have been shown to be conserved (J. A. Bruenn, Nucleic Acids Research, Vol. 19, No. 2 p. 217, 1991).

Currently, there are no safe and effective therapeutic agents on the market that target HCV polymerase. There is currently a need for therapeutic agents and therapeutic methods that are useful for treating viral infections, such as HCV, HIV, and HBV.

In addition, there is also a current need for therapeutic agents and therapeutic methods that are useful for treating cancer. Even though significant advances have occurred in the treatment of cancer, it still remains a major health concern. It has been reported that cancer is the cause of death of up to one of every four Americans. Notwithstanding the advances in treatments for cancer and other diseases there is still a need for novel drugs that are effective to treat cancer.

SUMMARY OF THE INVENTION

The present invention provides compounds that are inhibitors of viral RNA and DNA polymerases (e.g. polymerases from hepatitis B, hepatitis C, human immunodeficiency virus, Polio, Coxsackie A and B, Rhino, Echo, small pox, Ebola, and West Nile virus) and that are useful for treating HCV, as well as other viral infections (e.g. flaviviral infections), and cancer.

Accordingly, the invention provides novel compounds of formulae I, II, and III as described herebelow, or a pharmaceutically acceptable salt or prodrug thereof.

The invention also provides a pharmaceutical composition comprising a compound of formula I, II, or III, or a pharmaceutically acceptable salt or prodrug thereof, and a pharmaceutically acceptable carrier. The composition can optionally comprise one or more additional anti-viral or anti-cancer agents.

The invention also provides a method for treating a viral infection in an animal comprising administering to the animal an effective amount of a compound of formula I, II, or III, or a pharmaceutically acceptable salt or prodrug thereof.

The invention also provides a method for inhibiting a viral RNA or DNA polymerase comprising contacting the polymerase (in vitro or in vivo) with an effective inhibitory amount of a compound of formula I, II, or III, or a pharmaceutically acceptable salt or prodrug thereof.

The invention also provides a method for treating cancer in an animal comprising administering to the animal an effective amount of a compound of formula I, II, or III, or a pharmaceutically acceptable salt or prodrug thereof.

The invention also provides a compound of formula I, II, or III, or a pharmaceutically acceptable salt or prodrug thereof, for use in medical therapy (e.g. for use in treating a viral infection or for use in treating cancer).

The invention also provides the use of a compound of formula I, II, or III, or a pharmaceutically acceptable salt or prodrug thereof, to prepare a medicament useful for treating a viral infection in an animal (e.g. a human).

The invention also provides the use of a compound of formula I, II, or III, or a pharmaceutically acceptable salt or prodrug thereof, to prepare a medicament useful for treating cancer in an animal (e.g. a human).

The invention also provides novel synthetic intermediates and synthetic methods that are disclosed herein as being useful for preparing compounds of formula I, II, or III. Some compounds of formula I, II, and III may be useful as synthetic intermediates for preparing other compounds of formula I, II, and III.

DETAILED DESCRIPTION OF THE INVENTION

Definitions

The term "pharmaceutically acceptable salt" as used herein refers to a compound of the present disclosure derived from pharmaceutically acceptable bases, inorganic or organic acids. Examples of suitable acids include, but are not limited to, hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include, but are not limited to, alkali such as sodium and ammonia.

The terms "treat", "treating" and "treatment" as used herein include administering a compound prior to the onset of clinical symptoms of a disease state/condition so as to prevent any symptom, as well as administering a compound after the onset of clinical symptoms of a disease state/condition so as to reduce or eliminate any symptom, aspect or characteristic of the disease state/condition. Such treating need not be absolute to be useful.

The term "animal" as used herein refers to any animal, including mammals, such as, but not limited to, mice, rats, other rodents, rabbits, dogs, cats, swine, cattle, sheep, horses, and primates. In one specific embodiment of the invention the animal is a human.

The term "therapeutically effective amount", in reference to treating a disease state/condition, refers to an amount of a compound either alone or as contained in a pharmaceutical composition that is capable of having any detectable, positive effect on any symptom, aspect, or characteristics of a disease state/condition when administered as a single dose or in multiple doses. Such effect need not be absolute to be beneficial.

The term "alkyl" as used herein refers to alkyl groups having from 1 to 6 carbon atoms. This term is exemplified by groups such as methyl, ethyl, n-propyl, iso-propyl, n-butyl, t-butyl, n-pentyl and the like. In a specific embodiment, the alkyl groups have from 1-4 carbon atoms and are referred to as lower alkyl.

The term "substituted alkyl" as used herein refers to an alkyl group having from 1 to 3 substituents, said substituents being selected from the group consisting of alkoxy, substituted alkoxy, acyl, substituted acyl, acylamino, acyloxy, oxyacyl, amino, substituted amino, aminoacyl, aryl, substituted aryl, aryloxy, substituted aryloxy, cyano, halogen, hydroxyl, nitro, $N_3$, carboxyl, carboxyl esters, thiol, thioalkyl, substituted thioalkyl, thioaryl, substituted thioaryl, thioheteroaryl, substituted thioheteroaryl, thiocycloalkyl, substituted thiocycloallcyl, thioheterocyclic, substituted thioheterocycliccycloalkyl, substituted cycloalkyl, heteroaryl, substituted heteroaryl, heterocyclic, and substituted heterocyclic.

The terms "alkenyl" or "alkene" as used herein refers to an alkenyl group having from 2 to 10 carbon atoms and having at least 1 site of alkenyl unsaturation. Such groups are exemplified by vinyl(ethen-1-yl), allyl, but-3-en-1-yl, and the like.

The term "substituted alkenyl" as used herein refers to alkenyl groups having from 1 to 3 substituents, said substituents being selected from those describe above for a substituted alkyl.

The term "alkynyl" or "alkyne" as used herein refers to an alkynyl group having from 2-10 carbon atoms and having at least 1 site of alkynyl unsaturation. Such groups are exemplified by, but not limited to, ethyn-1-yl, propyn-1-yl, propyn-2-yl, 1-methylprop-2-yn-1-yl, butyn-1-yl, butyn-2-yl, butyn-3-yl, and the like.

The term "substituted alkynyl" as used herein refers to alkynyl groups having from 1 to 3 substituents, said substituents being selected those describe above for a substituted alkyl.

The term "alkoxy" refers to the group alkyl-O—.

The term "substituted alkoxy" as used herein refers to the group substituted alkyl-O—.

The term "acyl" as used herein refers to the groups alkyl-C(O)—, alkenyl-C(O)-alkynyl-C(O)—, cycloalkyl-C(O)—, aryl-C(O)—, heteroaryl-C(O)—, and heterocyclic-C(O).

The term "substituted acyl" as used herein refers to the groups substituted alkyl-C(O)—, substituted alkenyl-C(O)—, substituted alkynyl-C(O)—, substituted cycloalkyl-C(O)—, substituted aryl-C(O)—, substituted heteroaryl-C(O), and substituted heterocyclic-C(O)—.

The term "acylamino" as used herein refers to the group-C(O)N$Z_1Z_2$ where each $Z_1$ and $Z_2$ are independently selected from the group consisting of hydrogen, alkyl, substituted alkyl, alkenyl, substituted alkenyl, alkynyl and substituted alkynyl, and the substituents described above in the definition of substituted alkyl.

The term "acyloxy" as used herein refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—.

The term "oxyacyl" as used herein refers to the groups alkyl-OC(O)—, substituted alkyl-OC(O)—, alkenyl-OC(O)—, substituted alkenyl-OC(O)—, alkynyl-OC(O)—, substituted alkynyl-OC(O)—, aryl-OC(O)—, substituted aryl-OC(O)—, cycloalkyl-OC(O)—, substituted cycloalkyl-OC(O)—, heteroaryl-OC(O)—, substituted heteroaryl-OC(O)—, heterocyclic-OC(O)—, and substituted heterocyclic-OC(O)—.

The term "amino" as used herein refers to the group —NH$_2$.

The term "substituted amino" as used herein refers to the group -N Z$_1$Z$_2$ where Z$_1$ and Z$_2$ are as described above in the definition of acylamino, provided that Z$_1$ and Z$_2$ are both not hydrogen.

The term "aminoacyl" as used herein refers to the groups —NZ$_3$C(O)alkyl, —NZ$_3$C(O)substituted alkyl, —NZ$_3$C(O)cycloalkyl, —NZ$_3$C(O)substituted cycloalkyl, —NZ$_3$C(O)alkenyl, —NZ$_3$C(O)substituted alkenyl, —NZ$_3$C(O)alkynyl, —NZ$_3$C(O)substituted alkynyl, —NZ$_3$C(O)aryl, —NZ$_3$C(O)substituted aryl, —NZ$_3$C(O)heteroaryl, —NZ$_3$C(O)substituted heteroaryl, —NZ$_3$C(O)heterocyclic, and —NZ$_3$C(O)substituted heterocyclic, where NZ$_3$ is hydrogen or alkyl.

The term "aryl" as used herein refers to a monovalent aromatic cyclic group of from 6 to 14 carbon atoms having a single ring (e.g., phenyl) or multiple condensed rings (e.g., naphthyl or anthryl) which condensed rings may or may not be aromatic. Exemplary aryls include, but are not limited to, phenyl and naphthyl.

The term "substituted aryl" as used herein refers to aryl groups which are substituted with from 1 to 3 substituents selected from alkyl, substituted alkyl, alkenyl, substituted alkenyl, alkynyl and substituted alkynyl, and those substituents described above in the definition of substituted alkyl.

The term "aryloxy" as used herein refers to the group aryl-O— that includes, by way of example but not limitation, phenoxy, naphthoxy, and the like.

The term "substituted aryloxy" as used herein refers to substituted aryl-O-groups.

The term "carboxyl" as used herein refers to —COOH or salts thereof.

The term "carboxyl esters" as used herein refers to the groups-C(O)O-alkyl, —C(O)O-substituted alkyl, —C(O)O-aryl, and —C(O)O-substituted aryl The term "cycloalkyl" as used herein refers to a saturated or unsaturated cyclic hydrocarbon ring systems, such as those containing 1 to 3 rings and 3 to 7 carbons per ring. Exemplary groups include but are not limited to cyclopropyl, cyclobutyl, cyclopentyl, cyclohexyl, cycloheptyl, and adamantyl.

The term "substituted cycloalkyl" as used herein refers to a cycloalkyl having from 1 to 5 substituents selected from the group consisting of oxo (=O), thioxo (=S), alkyl, substituted alkyl, and those substituents described in the definition of substituted alkyl.

The term "cycloalkoxy" as used herein refers to —O-cycloalkyl groups.

The term "substituted cycloalkoxy" as used herein refers to —O-substituted cycloalkyl groups.

The term "formyl" as used herein refers to HC(O)—.

The term "halogen" as used herein refers to fluoro, chloro, bromo and iodo.

The term "heteroaryl" as used herein refers to an aromatic group of from 1 to 10 carbon atoms and 1 to 4 heteroatoms selected from the group consisting of oxygen, nitrogen, sulfur in the ring. The sulfur and nitrogen heteroatoms atoms may also be present in their oxidized forms. Such heteroaryl groups can have a single ring (e.g., pyridyl or furyl) or multiple condensed rings (e.g., indolizinyl or benzothienyl) wherein the condensed rings may or may not be aromatic and/or contain a heteroatom. Exemplary heteroaryl groups include, but are not limited to, heteroaryls include pyridyl, pyrrolyl, thienyl, indolyl, thiophenyl, and furyl.

The term "substituted heteroaryl" as used herein refers to heteroaryl groups that are substituted with from 1 to 3 substituents selected from the same group of substituents defined for substituted aryl.

The term "heteroaryloxy" as used herein refers to the group —O-heteroaryl.

The term "substituted heteroaryloxy" as used herein refers to the group —O-substituted heteroaryl.

The term "heterocycle" or "heterocyclic" or "heterocycloalkyl" refers to a saturated or unsaturated group (but not heteroaryl) having a single ring or multiple condensed rings, from 1 to 10 carbon atoms and from 1 to 4 hetero atoms selected from the group consisting of nitrogen, oxygen, sulfur, within the ring wherein, in fused ring systems, one or more the rings can be cycloalkyl, aryl or heteroaryl provided that the point of attachment is through the heterocyclic ring. The sulfur and nitrogen heteroatoms atoms may also be present in their oxidized forms.

The term "substituted heterocycle" or "substituted heterocyclic" or "substituted heterocycloalkyl" refers to heterocycle groups that are substituted with from 1 to 3 of the same substituents as defined for substituted aryl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

The term "heterocyclyloxy" as used herein refers to the group —O-heterocyclic.

The term "substituted heterocyclyloxy" as used herein refers to the group-O-substituted heterocyclic.

The term "phosphate" as used herein refers to the groups —OP(O)(OH)$_2$ (monophosphate or phospho), —OP(O)(OH)OP(O)(OH)$_2$ (diphosphate or diphospho) and —OP(O)(OH)OP(O)(OH)OP(O)(OH)$_2$ (triphosphate or triphospho) or salts thereof including partial salts thereof. It is understood that the initial oxygen of the mono-, di-, and triphosphate may include the oxygen atom of a sugar.

The term "phosphate esters" as used herein refers to the mono-, di- and tri-phosphate groups described above wherein one or more of the hydroxyl groups is replaced by an alkoxy group.

The term "phosphonate" refers to the groups —OP(O)(Z$_4$)(OH) or —OP(O) (Z$_4$)(OZ$_4$) or salts thereof including partial salts thereof, wherein each Z$_4$ is independently selected from hydrogen, alkyl, substituted alkyl, carboxylic acid, and carboxyl ester. It is understood that the initial oxygen of the phosphonate may include the oxygen of a sugar.

The term "thiol" as used herein refers to the group —SH.

The term "thioalkyl" or "alkylthioether" or "thioalkoxy" refers to the group —S-alkyl.

The term "substituted thioalkyl" or "substituted alkylthioether" or "substituted thioalkoxy" refers to the group —S-substituted alkyl.

The term "thiocycloalkyl" as used herein refers to the group —S-cycloalkyl.

The term "substituted thiocycloalkyl" as used herein refers to the group —S-substituted cycloalkyl.

The term "thioaryl" as used herein refers to the group —S-aryl.

The term "substituted thioaryl" as used herein refers to the group —S-substituted aryl.

The term "thioheteroaryl" as used herein refers to the group —S-heteroaryl.

The term "substituted thioheteroaryl" as used herein refers to the group —S-substituted heteroaryl.

The term "thioheterocyclic" as used herein refers to the group —S-heterocyclic.

The term "substituted thioheterocyclic as used herein refers to the group —S-substituted heterocyclic.

The term "amino acid sidechain" refers to the $Z_7$ substituent of α-amino acids of the formula $Z_6NHCH(Z_7)COOH$ where $Z_7$ is selected from the group consisting of hydrogen, alkyl, substituted alkyl and aryl and $Z_6$ is hydrogen or together with $Z_7$ and the nitrogen and carbon atoms bound thereto respectively form a heterocyclic ring. In one embodiment, the α-amino acid sidechain is the sidechain one of the twenty naturally occurring L amino acids.

Sugars described herein may either be in D or L configuration.

Compounds of Formula I

Compounds of the invention include compounds of formula I:

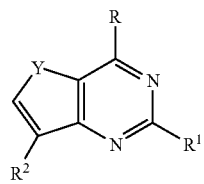

(I)

wherein:

Y is O or S;

R is $OR_3$, $SR_3$, $NR_3R_4$, $NR_3NR_4R_5$, alkyl, substituted alkyl, alkenyl, substituted alkenyl, alkynyl, substituted alkynyl, aryl, substituted aryl, $(CH_2)_n$—$CH(NHR_3)CO_2R_4$, Cl, F, Br, I, CN, $COOR_3$, $CONR_3R_4$, $NHC(=NR_3)NHR_4$, $NR_3OR_4$, $NR_3NO$, $NHCONHR_3$, $NR_3N=NR_4$, $NR_3N=CHR_4$, $NR_3C(O)NR_4R_5$, $NR_3C(S)NR_4R_5$, $NR_3C(O)OR_4$, $CH=N—OR_3$, $NR_3C(=NH)NR_4R_5$, $NR_3C(O)NR_4NR_5R_6$, O—$C(O)R_3$, OC(O)—$OR_3$, ONH—C(O)O-alkyl, ONHC(O)O-aryl, $ONR_3R_4$, $SNR_3R_4$, S—$ONR_3R_4$, or $SO_2NR_3R_4$;

n is 0-5;

$R^1$ is H, $NR_3R_4$, Cl, F, $OR_3$, $SR_3$, $NHCOR_3$, $NHSO_2R_3$, $NHCONHR_3$, CN, alkyl, aryl, $ONR_3R_4$, or $NR_3C(O)OR_4$;

$R^2$ is a nucleoside sugar group; and $R_3$, $R_4$, $R_5$, and $R_6$ are independently selected from the group consisting of H, alkyl, substituted alkyl, alkenyl, substituted alkenyl, alkynyl, substituted alkynyl, cycloalkyl, heterocyclic, aryl, substituted aryl, acyl, substituted acyl, $SO_2$-alkyl and NO; or $R_3$ and $R_4$ together with the nitrogen to which they are attached form a pyrrolidino, piperidino, piperazino, azetidino, morpholino, or thiomorpholino ring; or $R_4$ and $R_5$ together with the nitrogen to which they are attached form a pyrrolidino, piperidino, piperazino, azetidino, morpholino, or thiomorpholino ring;

or a pharmaceutically acceptable salt or prodrug thereof;

U.S. Pat. No. 4,584,369 relates to certain specific nucleosides. Accordingly, in one embodiment, the invention excludes compounds of formula I wherein Y is S; when R is —$NH_2$, —OH, —SH, or —$SCH_3$; $R^1$ is hydrogen; and $R^2$ is non-phosphorylated ribose; as well as compounds of formula I wherein Y is O; when R is —$NH_2$; $R^1$ is hydrogen; and $R^2$ is non-phosphorylated ribose.

In another embodiment the invention excludes compounds of formula I wherein Y is S; R is —$NH_2$, —OH, —SH, or —$SCH_3$; $R^1$ is hydrogen; and $R^2$ is ribose; as well as compounds of formula I wherein Y is O; R is —$NH_2$; $R^1$ is hydrogen; and $R^2$ is ribose.

In another embodiment, the invention excludes compounds of formula I wherein R is —SH, —OH, —S-alkyl, —O-alkyl, or $NR_3R_4$; $R_3$ and $R_4$ are each H or alkyl; and $R^2$ has the following formula:

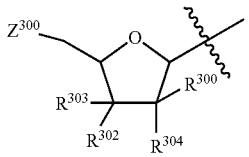

wherein: one of $R^{300}$ and $R^{304}$ is H and the other is H or OH; $R^{302}$ is OH, alkyl-O—, alkylC(=O)O—, alkyl-S—, or alkylC(=O)—S—; $R^{303}$ is H; and $Z^{300}$ is OH, alkyl-O—, alkylC(=O)O—, alkyl-S—, or alkylC(=O)—S—.

In another embodiment, the invention excludes compounds of formula I wherein $R^2$ has the following formula:

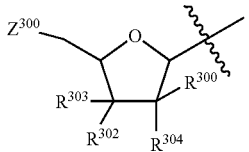

wherein: one of $R^{300}$ and $R^{304}$ is H and the other is H or OH; $R^{302}$ is OH, alkyl-O—, alkylC(=O)O, alkyl-S—, or -alkylC(=O)—S—; $R^{303}$ is H; and $Z^{300}$ is OH, alkyl-O—, alkylC(=O)O, alkyl-S—, or alkylC(=O)—S—.

In one embodiment the invention provides a compound of formula I as described above, wherein Y is O; or a pharmaceutically acceptable salt or prodrug thereof.

In one embodiment the invention provides a compound of formula I as described above, wherein Y is S; or a pharmaceutically acceptable salt or prodrug thereof.

In one embodiment the invention provides a compound of formula I as described above, wherein R is $OR_3$, Cl, $SR_3$, $NR_3R_4$, or $NR_3NR_4R_5$; or a pharmaceutically acceptable salt or prodrug thereof.

In one embodiment the invention provides a compound of formula I as described above, wherein R is $NR_3R_4$; $R_3$ is selected from the group consisting of H, alkyl, substituted alkyl, alkenyl, substituted alkenyl, alkynyl, substituted alkynyl, cycloalkyl, heterocyclic, aryl, substituted aryl, acyl, substituted acyl, $SO_2$-alkyl and NO; and $R_4$ is selected from the group consisting of H, alkyl, substituted alkyl, alkenyl, substituted alkenyl, alkynyl, substituted alkynyl, cycloalkyl, heterocyclic, aryl, substituted aryl, acyl, substituted acyl, $SO_2$-alkyl and NO; or $R_3$ and $R_4$ together with the nitrogen to which they are attached form a pyrrolidino, piperidino, piperazino, azetidino, morpholino, or thiomorpholino ring; or $R_4$ and $R_5$ together with the nitrogen to which they are attached form a pyrrolidino, piperidino, piperazino, azetidino, morpholino, or thiomorpholino ring.

In one embodiment the invention provides a compound of formula I as described above, wherein R is $NR_3NR_4R_5$, alkyl, substituted alkyl, alkenyl, substituted alkenyl, alkynyl, substituted alkynyl, aryl, substituted aryl, $(CH_2)_n$—$CH(NHR_3)$ $CO_2R_4$, Cl, F, Br, I, CN, $COOR_3$, $CONR_3R_4$, $NHC(=NR_3)$ $NHR_4$, $NR_3OR_4$, $NR_3NO$, $NHCONHR_3$, $NR_3N=NR_4$, $NR_3N=CHR_4$, $NR_3C(O)NR_4R_5$, $NR_3C(S)NR_4R_5$, $NR_3C$ $(O)OR_4$, $CH=N-OR_3$, $NR_3C(=NH)NR_4R_5$, $NR_3C(O)$ $NR_4NR_5R_6$, O—$C(O)R_3$, $OC(O)$—$OR_3$, $ONH$—$C(O)O$-alkyl, $ONHC(O)O$-aryl, $ONR_3R_4$, $SNR_3R_4$, S—$ONR_3R_4$, or $SO_2NR_3R_4$.

In one embodiment the invention provides a compound of formula I as described above, wherein $R_1$ is H or $NR_3R_4$; or a pharmaceutically acceptable salt or prodrug thereof.

In one embodiment the invention provides a compound of formula I as described above, wherein $R^2$ is a nucleoside sugar group of Group A, B, C, D, E, or F described hereinbelow; or a pharmaceutically acceptable salt or prodrug thereof.

In another embodiment the invention provides a compound of formula I as described above, wherein $R^2$ is ribose, 2-deoxyribose; 2-deoxy-2-fluororibose; arabinose; 2-deoxy-2-fluoroarabinose; 2,3-dideoxyribose; 2,3-dideoxy-2-fluoroarabinose; 2,3-dideoxy-3-fluororibose; 2,3-dideoxy-2,3-didehydroribose; 2,3-dideoxy-3-azidoribose; 2,3-dideoxy-3-thiaribose; or 2,3-dideoxy-3-oxaribose; or a pharmaceutically acceptable salt or prodrug thereof.

In another embodiment the invention provides a compound of formula I as described above, wherein $R^2$ is ribose, 2-methylribose, 2-deoxyribose; 2-deoxy-2-fluororibose; arabinose; 2-deoxy-2-fluoroarabinose; 2,3-dideoxyribose; 2,3-dideoxy-2-fluoroarabinose; 2,3-dideoxy-3-fluororibose; 2,3-dideoxy-2,3-didehydroribose; 2,3-dideoxy-3-azidoribose; 2,3-dideoxy-3-thiaribose; or 2,3-dideoxy-3-oxaribose; or a pharmaceutically acceptable salt or prodrug thereof.

In another embodiment the invention provides a compound of formula I as described above, wherein $R^2$ is thioribose, 2-deoxythioribose; 2-deoxy-2-fluorothioribose; thioarabinose; 2-deoxy-2-fluorothioarabinose; 2,3-dideoxythioribose; 2,3-dideoxy-2-fluorothioarabinose; 2,3-dideoxy-3-fluorothioribose; 2,3-dideoxy-2,3-didehydrothioribose; or 2,3-dideoxy-3-azidothioribose; or a pharmaceutically acceptable salt or prodrug thereof.

In another embodiment the invention provides a compound of formula I as described above, wherein $R^2$ is 4-hydroxymethylcyclopent-2-ene; 2,3-dihydroxy-4-hydroxymethylcyclopent-4-ene; 3-hydroxy-4-hydroxymethylcyclopentane; 2-hydroxy-4-hydroxymethylcyclopentene; 2-fluoro-3-hydroxy-4-hydroxymethylcyclopentane; 2,3-dihydroxy-4-hydroxymethyl-5-methylenecyclopentane; 4-hydroxymethylcyclopentane, 2,3-dihydroxy-4-hydroxymethylcyclopentane; or 2,3-dihydroxymethylcyclobutane; or a pharmaceutically acceptable salt or prodrug thereof.

In another embodiment the invention provides a compound of formula I as described above, wherein $R^2$ is 4-hydroxymethylpyrrolidine; 2,3-dihydroxy-4-hydroxymethylpyrrolidine; 2/3-hydroxy-4-hydroxymethylpyrrolidine; 2-fluoro-3-hydroxy-4-hydroxymethylpyrrolidine; or 3-fluoro-2-hydroxy-4-hydroxymethylpyrrolidine; or a pharmaceutically acceptable salt or prodrug thereof.

In another embodiment the invention provides a compound of formula I as described above, wherein $R_3$, $R_4$, $R_5$, and $R_6$ are independently selected from the group consisting of H, alkyl, and substituted alkyl; or $R_3$ and $R_4$ together with the nitrogen to which they are attached form a pyrrolidino, piperidino, piperazino, azetidino, morpholino, or thiomorpholino ring; or $R_4$ and $R_5$ together with the nitrogen to which they are attached form a pyrrolidino, piperidino, piperazino, azetidino, morpholino, or thiomorpholino ring.

Compounds of Formula II

The invention also provides novel compounds of formula II:

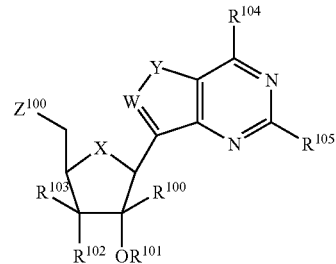

wherein:

$R^{100}$ is alkyl (1-4 carbon atom), alkenyl, or alkynyl, which $R^{100}$ may be unsubstituted or substituted;

$R^{101}$ is H, alkyl, —C(O)alkyl, or aryl-C(=O)—;

$R^{102}$ is H, OH, —Oalkyl, —OC(O)alkyl, aryl-C(=O)—O—, —$CH_2OH$, $CH_2NH_2$, $N_3$, $CH_2N_3$, or $NH_2$;

$R^{103}$ is H, OH, or $NH_2$; provided both $R^{102}$ and $R^{103}$ cannot be the same group except hydrogen.

$R^{104}$ is $NR^{110}R^{111}$, $NR^{110}$—$NR^{111}R^{112}$, $NR^{110}N=NR^{111}$, $NR^{110}N=CHR^{111}$, $NR^{110}N=O$, $NR^{110}C(O)NR^{111}R^{112}$, $NR^{110}C(S)NR^{111}R^{112}$, $NR^{110}C(=NH)NR^{111}R^{112}$, $NR^{110}C(O)NR^{111}NR^{112}R^{113}$, $NR^{110}R^{111}$, O—$C(O)R^{110}$, $OC(O)$—$OR^{110}$, O—NH—C(O)Oalkyl, ONHC(O)Oaryl, $ONR^{110}R^{111}$, S—$NR^{110}R^{111}$, S—$ONR^{110}R^{111}$, or $SO_2NR^{110}R^{111}$;

$R^{105}$ is H, halogen, $N_3$, $NHC(O)R^{106}$, $NR^{110}R^{111}$, $NHSO_2R^{106}$, $NHCONHR^{106}$, NH—$C(S)NHR^{106}$, $CH_2NHR^{106}$, $NHNH_2$, CN, alkyl, alkynyl, $CH_2$aryl, OH, or $SR^{106}$;

$R^{106}$ is H or alkyl;

$Z^{100}$ is OH, —O—$[P(=O)(OH)O-]_n$—H, —$CH_2$—$[P(=O)(OH)O-]_n$—H, —O—$P(=O)(R^{107})R^{108}$, —$CH_2$—$P(=O)(R^{107})R^{108}$, —O—$[P(=O)(R^{109})O-]_n$—H, or —$CH_2$—$[P(=O)(R^{109})O-]_n$—H;

$R^{107}$ and $R^{108}$ in phosphonic acid or phosphoric acid independently represent a protected or unprotected substituted or unsubstituted hydroxyl group to be decomposed under physiological conditions;

$R^{109}$ is a hydroxyl group that may be protected or substituted with a group to be decomposed under physiological conditions;

$R^{110}$, $R^{111}$, $R^{112}$ and $R^{113}$ are independently H, alkyl, substituted alkyl, cycloalkyl, heterocyclic, alkoxy, aryl, substituted aryl, acyl, substituted acyl, $SO_2$-alkyl, $NH_2$, OH or NO;

$R^{114}$ is H, alkyl, substituted alkyl, $C(O)R^{109}$, aryl, substituted aryl, or heterocycle;

n is 0-3;

X is O, S, NH, or $CH_2$;

W is $CHR^{114}$, N, or CH-halo;

Y is O, S, or $NR^{114}$; and or a pharmaceutically acceptable salt or prodrug thereof.

In one embodiment the invention provides a compound of formula II as described above, wherein Y is O or S; or a pharmaceutically acceptable salt or prodrug thereof.

In another embodiment the invention provides a compound of formula II as described above, wherein $R^{101}$ is H, alkyl, —C(O)alkyl, or benzoyl; and $R^{102}$ is H, OH, Oalkyl, —OC (O)alkyl, benzoyl-O—, —CH$_2$OH, CH$_2$NH$_2$, N$_3$, CH$_2$N$_3$, or NH$_2$; or a pharmaceutically acceptable salt or prodrug thereof.

In another embodiment the invention provides a compound of formula II as described above, wherein Y is O or S; R$^{101}$ is H, alkyl, —C(O)alkyl, or benzoyl; and R$^{102}$ is H, OH, Oalkyl, —OC(O)alkyl, benzoyl-O—, —CH$_2$OH, CH$_2$NH$_2$, N$_3$, CH$_2$N$_3$, or NH$_2$; or a pharmaceutically acceptable salt or prodrug thereof.

In another embodiment the invention provides a compound of formula II as described above, wherein Y is O or S; and W is CR$^{114}$, N, or C-halo; or a pharmaceutically acceptable salt or prodrug thereof.

In another embodiment the invention provides a compound of formula II as described above wherein Y is O or S; Z$^{100}$ is OH, —O—[P(=O)(OH)O—]$_n$—H, —CH$_2$—[P(=O)(OH)O—]$_n$—H, —O—P(=O)(R$^{107}$)R$^{108}$, —CH$_2$—P(=O)(R$^{107}$)R$^{108}$, —O—[P(=O)(R$^{109}$)O—]$_n$—H, or —CH$_2$—[P(=O)(R$^{109}$)O—]$_n$—H; and R$^{107}$ and R$^{108}$ are each H; or a pharmaceutically acceptable salt or prodrug thereof.

In another embodiment the invention provides a compound of formula II as described above wherein Y is O or S; Z$^{100}$ is OH, —O—[P(=O)(OH)O—]$_n$—H, —CH$_2$—[P(=O)(OH)O—]$_n$—H, —O—P(=O)(R$^{107}$)R$^{108}$, —CH$_2$—P(=O)(R$^{107}$)R$^{108}$, —O—[P(=O)(R$^{109}$)O—]$_n$—H, or —CH$_2$—[P(=O)(R$^{109}$)O—]$_n$—H; W is CR$^{114}$, N, or C-halo; and R$^{107}$ and R$^{108}$ are each H; or a pharmaceutically acceptable salt or prodrug thereof.

In another embodiment the invention provides a compound of formula II as described above wherein R$^{100}$ is alkyl; R$^{101}$ is H; R$^{102}$ is OH; R$^{103}$ is H; R$^{104}$ is NR$^{110}$R$^{111}$ or NR$^{110}$—NR$^{111}$R$^{112}$; R$^{105}$ is H or NH$_2$; R$^{110}$, R$^{111}$, R$^{112}$ and R$^{113}$ are independently H, alkyl, substituted alkyl, or cycloalkyl; and Z$^{100}$ is OH.

For a compound of formula II, a specific value for R$^{100}$ is alkyl.

For a compound of formula II, a specific value for R$^{101}$ is H.

For a compound of formula II, a specific value for R$^{102}$ is OH.

For a compound of formula II, a specific value for R$^{103}$ is H.

For a compound of formula II, a specific value for R$^{104}$ is NR$^{110}$R$^{111}$ or NR$^{110}$—NR$^{111}$R$^{112}$.

For a compound of formula II, a specific value for R$^{105}$ is H or NH$_2$.

For a compound of formula II, a specific value for R$^{107}$ is OH.

For a compound of formula II, a specific value for R$^{108}$ is OH.

For a compound of formula II, a specific value for R$^{110}$, R$^{111}$, R$^{112}$ and R$^{113}$ are independently H, alkyl, substituted alkyl, or cycloalkyl.

For a compound of formula II, a specific value for Z$^{100}$ is OH.

For a compound of formula II, a specific value for Z$^{100}$ is —O—[P(=O)(OH)O-]$_n$—H, —O—P(=O)(R$^{107}$)R$^{108}$, or —O—[P(=O)(R$^{109}$)O—]$_n$—H.

For a compound of formula II, a specific value for Z$^{100}$ is —CH$_2$—[P(=O)(R$^{109}$)O—]$_n$H.

Compounds of Formula III

The invention also provides novel compounds of formula III:

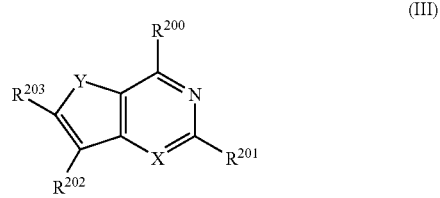

(III)

wherein:
X is N or CH;
Y is O, S or N—R$^{204}$;
R$^{200}$ is OR$^{205}$, OH, NHR$^{204}$, NR$^{204}$R$^{205}$, NHNHR$^{204}$, NR$^{204}$NHR$^{205}$, SR$^{205}$, SH, alkyl, aryl, Cl, NR$^{204}$OR$^{205}$, NR$^{204}$NO, or NHCONHR$^{204}$;
R$^{201}$ is H, NHR$^{204}$, Cl, F, OR$^{204}$, SR$^{204}$, NHCOR$^{204}$, NHSO$_2$R$^{204}$, NHCONHR$^{204}$, CN, alkyl, aryl, or NR$^{204}$R$^{205}$;
R$^{202}$ is a substituted alkyl, moiety from a sugar with the proviso that when Y=NH or S and R$^{200}$ is NH$_2$, OH, SH, alkylamino, alkyloxy, or alkylthio, the sugar moiety can not be from ribose or 2-deoxyribose; a moiety from a thio sugar; hydroxyl substituted cycloalkanes; or hydroxyl substituted 5-pyrrolidine moieties;
R$^{203}$ is H, alkyl, aryl, F, Cl, CN, CO$_2$H or NH$_2$;
R$^{204}$ is H, OH, alkyl, aryl, —COO-alkyl, CONH$_2$, CONH-alkyl, O—C(O)-alkyl, O—C(O)-aryl or alkoxy; and
R$^{205}$ is alkyl, aryl, OH or alkoxy;
and pharmaceutically acceptable salts thereof and prodrugs thereof.

In one embodiment the invention provides a compound of formula III as described above, wherein Y is O or S; or a pharmaceutically acceptable salt or prodrug thereof.

In one embodiment the invention provides a compound of formula III as described above, wherein R$^{200}$ is OR$^{205}$, NHR$^{204}$, NR$^{204}$R$^{205}$, NHNHR$^{204}$, NR$^{204}$NHR$^{205}$, SR$^{205}$, alkyl, aryl, Cl, NR$^{204}$OR$^{205}$, NR$^{204}$NO, or NHCONHR$^{204}$.

In one embodiment the invention provides a compound of formula III as described above, wherein R$^{202}$ is a nucleoside sugar group; or a pharmaceutically acceptable salt or prodrug thereof.

In another embodiment the invention provides a compound of formula III as described above, wherein R$^{202}$ is ribose, 2-deoxyribose; 2-deoxy-2-fluororibose; arabinose; 2-deoxy-2-fluoroarabinose; 2,3-dideoxyribose; 2,3-dideoxy-2-fluoroarabinose; 2,3-dideoxy-3-fluororibose; 2,3-dideoxy-2,3-didehydroribose; 2,3-dideoxy-3-azidoribose; 2,3-dideoxy-3-thiaribose; or 2,3-dideoxy-3-oxaribose.

In another embodiment the invention provides a compound of formula III as described above, wherein R$^{202}$ is ribose, 2-methylribose, 2-deoxyribose; 2-deoxy-2-fluororibose; arabinose; 2-deoxy-2-fluoroarabinose; 2,3-dideoxyribose; 2,3-dideoxy-2-fluoroarabinose; 2,3-dideoxy-3-fluororibose; 2,3-dideoxy-2,3-didehydroribose; 2,3-dideoxy-3-azidoribose; 2,3-dideoxy-3-thiaribose; or 2,3-dideoxy-3-oxaribose.

In another embodiment the invention provides a compound of formula III as described above, wherein R$^{202}$ is thioribose, 2-deoxythioribose; 2-deoxy-2-fluorothioribose; thioarabinose; 2-deoxy-2-fluorothioarabinose; 2,3-dideoxythioribose;

2,3-dideoxy-2-fluorothioarabinose; 2,3-dideoxy-3-fluorothioribose; 2,3-dideoxy-2,3-didehydrothioribose; or 2,3-dideoxy-3-azidothioribose.

In another embodiment the invention provides a compound of formula III as described above, wherein $R^{202}$ is 4-hydroxymethylcyclopent-2-ene; 2,3-dihydroxy-4-hydroxymethylcyclopent-4-ene; 3-hydroxy-4-hydroxymethylcyclopentane; 2-hydroxy-4-hydroxymethylcyclopentene; 2-fluoro-3-hydroxy-4-hydroxymethylcyclopentane; 2,3-dihydroxy-4-hydroxymethyl-5-methylenecyclopentane; 4-hydroxymethylcyclopentane, 2,3-dihydroxy-4-hydroxymethylcyclopentane; or 2,3-dihydroxymethylcyclobutane.

In another embodiment the invention provides a compound of formula III as described above, wherein $R^{202}$ is 4-hydroxymethylpyrrolidine; 2,3-dihydroxy-4-hydroxymethylpyrrolidine; 2/3-hydroxy-4-hydroxymethylpyrrolidine; 2-fluoro-3-hydroxy-4-hydroxymethylpyrrolidine; or 3-fluoro-2-hydroxy-4-hydroxymethylpyrrolidine.

In another embodiment the invention provides a compound of formula III as described above, wherein X is N; Y is NH; $R^{200}$ is $NH_2$; $R^{201}$ is H; and $R^{203}$ is H; or a pharmaceutically acceptable salt or prodrug thereof.

In another embodiment the invention provides a compound of formula III as described above, wherein X is N; Y is NH; $R^{200}$ is OH; $R^{201}$ is H; and $R^3$ is H; or a pharmaceutically acceptable salt or prodrug thereof.

In another embodiment the invention provides a compound of formula III as described above, wherein X is N; Y is S; $R^{200}$ is $NH_2$; $R^{201}$ is H; and $R^{203}$ is H; or a pharmaceutically acceptable salt or prodrug thereof.

In another embodiment the invention provides a compound of formula III as described above, wherein X is N; Y is O; $R^{200}$ is $NH_2$; $R^{201}$ is H; and $R^{203}$ is H; or a pharmaceutically acceptable salt or prodrug thereof.

In another embodiment the invention provides a compound of formula III as described above, wherein X is N; Y is O; $R^{200}$ is Cl, SH or S-alkyl; $R^{201}$ is H; and $R^{203}$ is H; or a pharmaceutically acceptable salt or prodrug thereof.

In another embodiment the invention provides a compound of formula III as described above, wherein X is N; Y is O; $R^{200}$ is Cl; $R^{201}$ is H; and $R^{203}$ is H; or a pharmaceutically acceptable salt or prodrug thereof.

In another embodiment the invention provides a compound of formula III as described above, wherein X is N; Y is O, S or NH; $R^{200}$ is OH; $R^{201}$ is $NH_2$; and $R^{203}$ is H; or a pharmaceutically acceptable salt or prodrug thereof.

In another embodiment the invention provides a compound of formula III as described above, wherein X is N; Y is O, S or NH; $R^{200}$ is $NHR^{204}$, $NR^{204}R^{205}$, aryl, $NR^{204}OR^{205}$, $NR^{204}NHR^{205}$, $NHNHR^{204}$, $SR^{205}$ or $OR^{205}$; $R^{201}$ is H, and $R^{203}$ is H; or a pharmaceutically acceptable salt or prodrug thereof.

In another embodiment the invention provides a compound of formula III as described above, wherein X is CH; Y is O, NH or S; $R^{200}$ is Cl, aryl, $NHR^{204}$, $NR^{204}R^{205}$, $OR^{205}$, $SR^{205}$, $NHNHR^{204}$, $NR^{204}NHR^{205}$, or $NR^{204}OR^{205}$; $R^{201}$ is H, and $R^{203}$ is H; or a pharmaceutically acceptable salt or prodrug thereof.

In another embodiment the invention provides a compound of formula III as described above, wherein X is N; Y is O, S or NH; $R^{200}$ is $NH_2$; $R^{201}$ is H, $R^{202}$ is any alkyl group containing hydroxyl; and $R^{203}$ is H; or a pharmaceutically acceptable salt or prodrug thereof.

In another embodiment the invention provides a compound of formula III as described above, wherein: X is N; Y is O or S; $R^{200}$ is $OR^{205}$, $NHR^{204}$, $NR^{204}R^{205}$, $NHNHR^{204}$, $NR^{204}NHR^{205}$, $SR^{205}$, or Cl; $R^{201}$ is H or $NHR^{204}$; $R^{202}$ is a substituted alkyl, moiety from a sugar with the proviso that when Y=NH or S and $R^{200}$ is $NH_2$, OH, SH, alkylamino, alkyloxy, or alkylthio, the sugar moiety can not be from ribose or 2-deoxyribose; a moiety from a thio sugar; hydroxyl substituted cycloalkanes; or hydroxyl substituted 5-pyrrolidine moieties; $R^{203}$ is H; $R^{204}$ is H, or alkyl; and $R^{205}$ is alkyl; or a pharmaceutically acceptable salt or prodrug thereof.

In another embodiment the invention provides a compound of formula III as described above, wherein: X is N; Y is O or S; $R^{200}$ is $OR^{205}$, $NHR^{204}$, $NR^{204}R^{205}$, $NHNHR^{204}$, $NR^{204}NHR^{205}$, $SR^{205}$, or Cl; $R^{201}$ is H or $NHR^{204}$; $R^{202}$ is a nucleoside sugar group with the proviso that when Y=NH or S and $R^{200}$ is $NH_2$, OH, SH, alkylamino, alkyloxy, or alkylthio, the sugar moiety is not ribose or 2-deoxyribose; $R^{203}$ is H; $R^{204}$ is H, or alkyl; and $R^{205}$ is alkyl; or a pharmaceutically acceptable salt or prodrug thereof.

For a compound of formula III, a specific value for X is N.

For a compound of formula III, a specific value for Y is O or S.

For a compound of formula III, a specific value for $R^{200}$ is $OR^{205}$, $NHR^{204}$, $NR^{204}R^{205}$, $NHNHR^{204}$, $NR^{204}NHR^{205}$, $SR^{205}$, or Cl.

For a compound of formula III, a specific value for $R^{201}$ is H or $NHR^{204}$.

For a compound of formula III, a specific value for $R^{202}$ is a substituted alkyl, moiety from a sugar.

For a compound of formula III, a specific value for $R^{203}$ is H, alkyl, aryl, F, Cl, CN, $CO_2H$ or $NH_2$.

Prodrugs

The term "prodrug" as used herein refers to a compound that can be metabolized in vivo to provide a compound of formula I, II, or III. Thus prodrugs include compounds that can be prepared by modifying one or more functional groups in a compound of formula I, II, or II, to provide a corresponding compound that can be metabolized in vivo to provide a compound of formula I, II, or III. Such modifications are known in the art. For example, one or more hydroxy groups or amine groups in a compound of formula I, II, or III, can be acylated with alkyl-C(=O)-groups or with residues from amino acids to provide a prodrug. Alternatively, one or more pendent hydroxyl groups from a mono-, di-, or tri-phosphate functionality in a compound of formula I, II, or III can be converted to an alkoxy, substituted alkoxy, aryloxy, or substituted aryloxy group.

In one embodiment, the term prodrug includes a compound wherein one or more hydroxy groups on a nucleoside sugar group (e.g. a 2', 3', or 5' hydroxy group) have been converted to a group that can be metabolized in vivo to provide a compound of formula I, II, or III. For example, the invention provides a compound wherein one or more hydroxy groups on a nucleoside sugar group (e.g. a 2', 3', or 5' hydroxy group) have been converted to an acyloxy, acylamino or R—O group, wherein R is a carboxy-linled amino acid.

In one embodiment, the term prodrug includes a compound wherein one or more pendent hydroxyl groups from a mono-, di-, or tri-phosphate functionality in a compound of formula I, II, or III is converted to a group $R_y$—O—; wherein each $R_y$ is independently a 1-20 carbon branched or unbranched, saturated or unsaturated chain, wherein one or more (e.g. 1, 2, 3, or 4) of the carbon atoms is optionally replaced with —O— or —S— and wherein one or more of the carbon atoms is optionally substituted with oxo (=O) or thioxo (=S) (See Lefebvre et al., J. Med. Chem. 1995, 38, 3941-50).

In another embodiment, the term prodrug includes a compound wherein one or more pendent hydroxyl groups from a mono-, di-, or tri-phosphate functionality in a compound of formula I, II, or III is converted to a group $R_z$—N—; wherein each $R_z$ is a residue of an amino acid. Thus, in the methods of treatment of the present invention, the term "administering" includes administration of a compound of formula I, II, or III, as well as administration of a prodrug which converts to a compound of formula I, II, or III or a salt thereof in vivo. Conventional procedures for the selection and preparation of prodrug derivatives are described, for example, in "Design of Prodrugs", ed. H. Bundgaard, Elsevier, 1985; and in International Patent Application Publication Number WO 2005/084192. A variety of prodrugs are also described in International Patent Application Number PCT US2004/013063, which was published as International Publication Number WO 2004/096286.

In another embodiment the prodrug comprises one of more groups of formula:

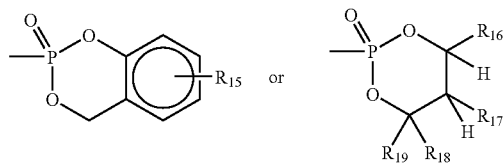

wherein:

$R_{15}$ is H, alkyl, substituted alkyl, aryl, substituted aryl, cycloalkyl, substituted cycloalkyl, heteroaryl, substituted heteroaryl, heterocyclic, substituted heterocyclic, and an amino acid;

$R_{16}$ is H, optionally substituted monocyclic aryl, or optionally substituted monocyclic heteroaryl; and $R_{17}$ is H, halogen, CN, —CO—$R_{20}$, —CON($R_{21}$)$_2$, —CO$_2$$R_{20}$, —SO$_2$$R_{20}$, —SO$_2$N($R_{21}$)$_2$, —O$R_{21}$, —S$R_{21}$, —$R_{21}$, —N($R_{21}$)$_2$, —O—CO$R_{20}$, —O—CO$_2$$R_{20}$, —SCO$R_{20}$, —S—CO$_2$$R_{20}$, —NHCO$R_{21}$, —NHCO$_2$$R_{21}$, —(CH$_2$)$_p$—O$R_{22}$, or —(CH$_2$)$_p$—S$R_{22}$; or $R_{16}$ and $R_{17}$ are connected via an additional 3-5 atoms to form a cyclic group, optionally containing one heteroatom, that is fused to an aryl group at the beta and gamma position to the O attached to the phosphorus; or $R_{17}$ and $R_{18}$ are connected as described below;

$R_{18}$ and $R_{19}$ are each independently H, alkyl, aryl, heterocycloalkyl, aralkyl, optionally substituted monocyclic aryl or optionally substituted monocyclic heteroaryl; or $R_{18}$ and $R_{19}$ are connected via an additional 2-5 atoms to form a cyclic group, optionally containing 0-2 heteroatoms; or $R_{17}$ and $R_{18}$ are connected via an additional 3-5 atoms to form a cyclic group, optionally containing one heteroatom and $R_{19}$ is H, alkyl, aryl, heterocycloalkyl, aralkyl, optionally substituted monocyclic aryl or optionally substituted monocyclic heteroaryl; and $R_{20}$ is alkyl, aryl, heterocycloalkyl, or arylalkyl;
$R_{21}$ is H, alkyl, aryl, heterocycloalkyl, or arylalkyl;
$R_{22}$ is H or lower acyl;
n is an integer from 2-5;
m is an integer from 10-20; and
p is an integer from 2-3.

Prodrug forms of a compound bearing various nitrogen functions (amino, hydroxyamino, amide, etc.) may include the following types of derivatives where each $R_p$ group individually may be hydrogen, substituted or unsubstituted alkyl, aryl, alkenyl, alkynyl, heterocycle, alkylaryl, aralkyl, aralkenyl, aralkynyl, cycloalkyl or cycloalkenyl groups as defined earlier.

(a) Carboxamides, represented as —NHC(O)$R_p$
(b) Carbamates, represented as —NHC(O)O$R_p$
(c) (Acyloxy)alkyl Carbamates, represented as NHC(O)OROC(O)$R_p$
(d) Enamines, represented as —NHCR(=CHCO$_2$$R_p$) or —NHCR(=CHCONR$_p$$R_p$)
(e) Schiff Bases, represented as —N=CR$_p$R$_p$
(f) Mannich Bases (from carboximide compounds), represented as RCONHCH$_2$NR$_p$R$_p$ Preparations of such prodrug derivatives are discussed in various literature sources (examples are: Alexander et al., J. Med. Chem. 1988, 31, 318; Aligas-Martin et al., PCT WO0041531, p. 30).

Prodrug forms of carboxyl-bearing compounds include esters (—CO$_2$$R_m$) where the $R_m$ group corresponds to any alcohol whose release in the body through enzymatic or hydrolytic processes would be at pharmaceutically acceptable levels. Another prodrug derived from a carboxylic acid form of the disclosure may be a quaternary salt type of structure described by Bodor et al., J. Med. Chem. 1980, 23, 469.

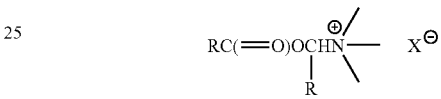

Nucleoside Sugar Groups

The term "nucleoside sugar group" as used herein includes cyclic and acyclic groups that can be included as the sugar portion of a nucleoside analog of formula I, II, or III. Many examples of such groups are known in the field of nucleoside chemistry (See for example Antiviral Drugs by John S. Driscoll (2002) published by Ashgate Publishing Ltd.).

The term nucleoside sugar group includes substituted and unsubstituted tetrahydrofuranyl and dihydrofuranyl compounds including those set forth in group (A) below, substituted and unsubstituted tetrahydrothiophenyl and dihydrothiophenyl compounds including those set forth in group (B) below, substituted and unsubstituted alkyl compounds including those set forth in group (C) below, substituted and unsubstituted cycloalkyl and cycloalkenyl compounds including those set forth in group (D) below, substituted and unsubstituted dihydropyrrolidinyl and tetrahydropyrrolidinyl compounds including those set forth in group (E) below, and substituted and unsubstituted dioxolane, substituted and unsubstituted thioxolane, and substituted and unsubstituted dithiolane compounds including those set forth in group (F) below.

Group A

Examples of substituted tetrahydro and dihydrofuranyl compounds include those compounds represented by the general structures:

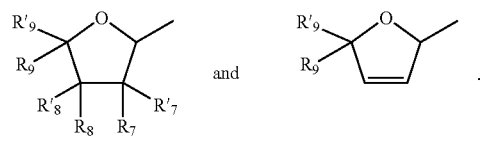

Specific examples include, but are not limited to, the following compounds:

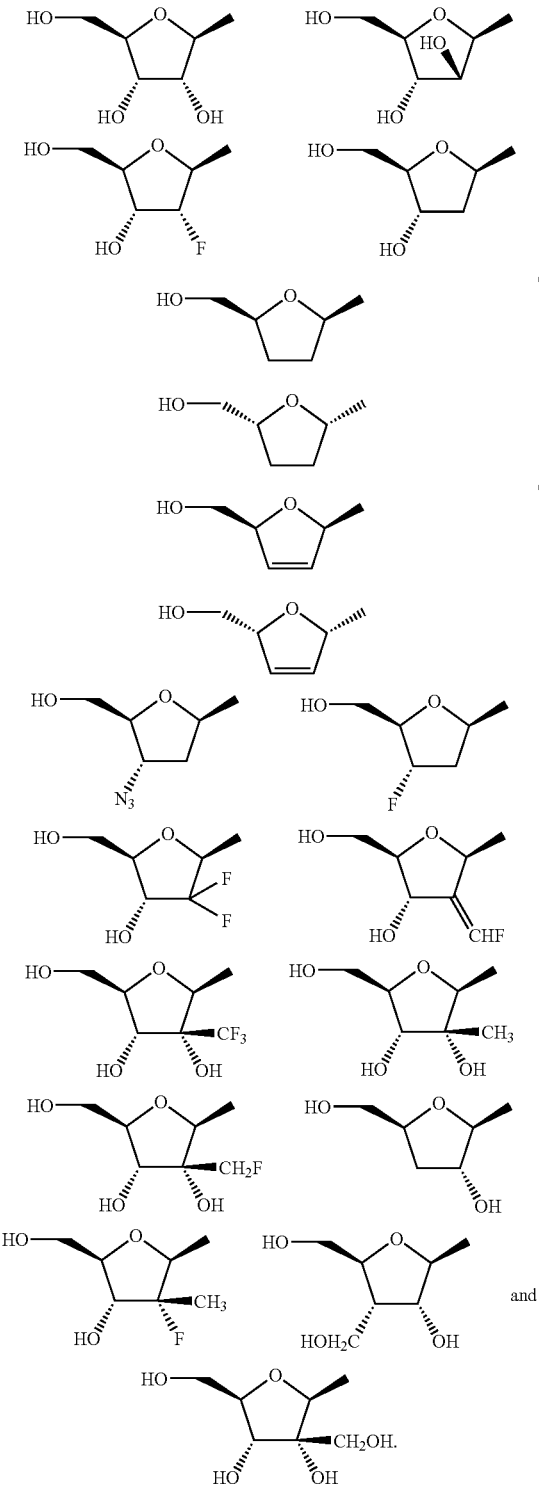

Group B

Examples of substituted tetrahydrothiophenyl and dihydrothiophenyl compounds include those compounds represented by the general structures:

and

Specific examples include, but are not limited to, the following compounds:

Group C

Examples of substituted alkyl compounds include those compounds represented by:

-continued

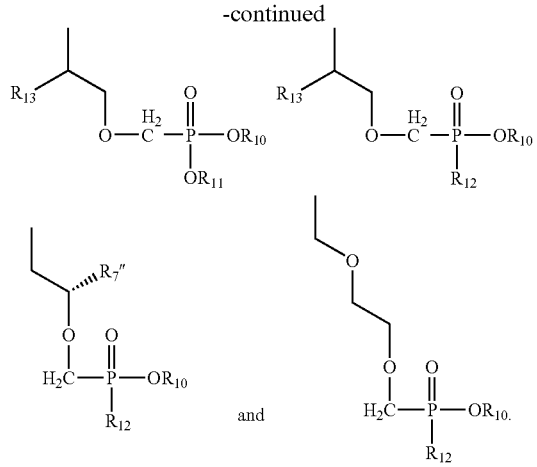

Specific examples include, but are not limited to, the following compounds:

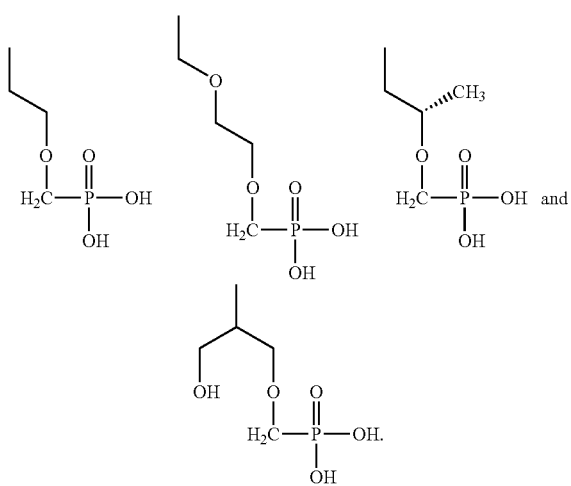

Group D
Examples of substituted cycloalkyl and cycloalkenyl compounds include those compounds represented by the general structures:

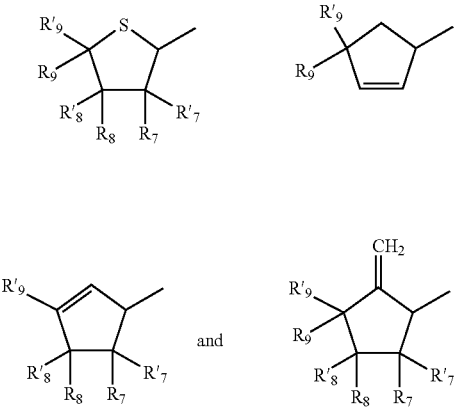

Specific examples include, but are not limited to, the following compounds:

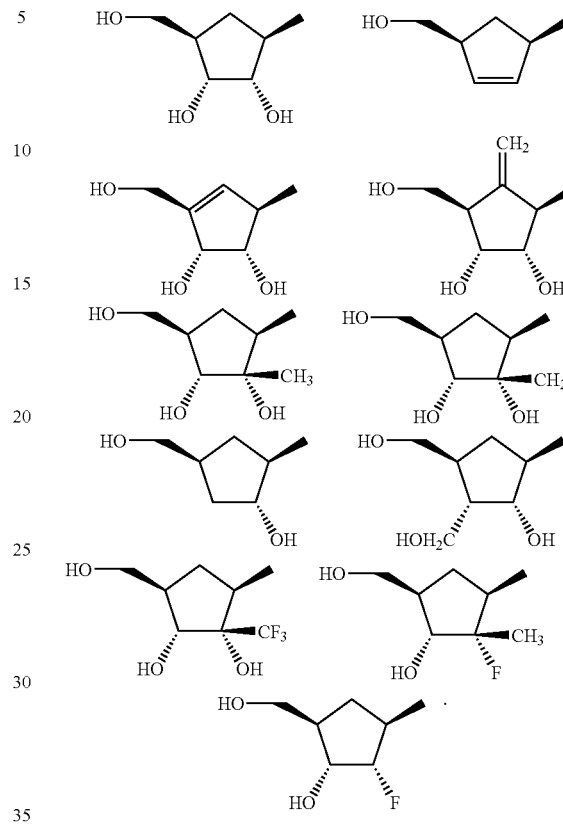

Group E
Examples of substituted dihydropyrrolidinyl and tetrahydropyrrolidinyl compounds include those compounds represented by the general structures:

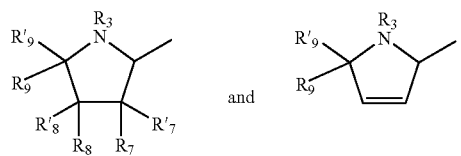

Specific examples include, but are not limited to, the following compounds:

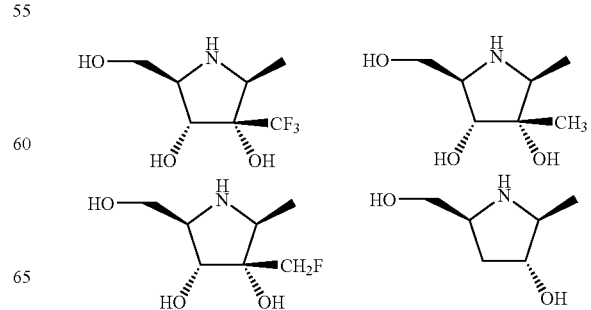

-continued

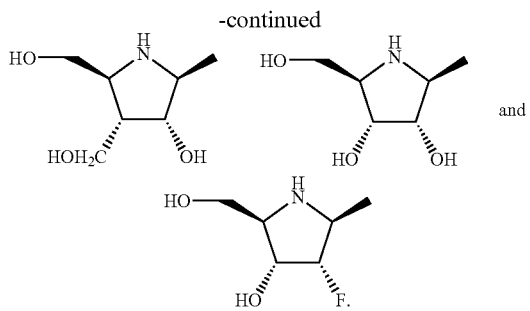

Group F

Examples of substituted dioxolane, substituted thioxolane and substituted dithiolane compounds include those compounds represented by the general structures:

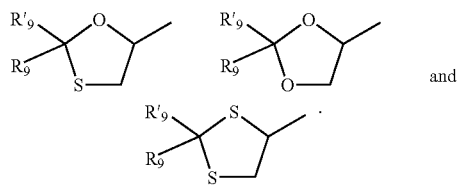

Specific examples include, but are not limited to, the following compounds:

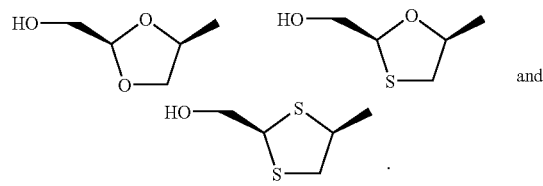

For the structures in Groups A-F, the following definitions apply:

$R_7$ is H, $OR_{14}$, $N_3$, $NH_2$, or F; and $R'_7$ is H, F, OH, O-alkyl, alkyl, substituted alkyl, alkenyl, substituted alkenyl, alkynyl, or substituted alkynyl; or $R_7$ and $R'_7$ together may be =$CH_2$, =CHF; wherein both $R_7$ and $R'_7$ are not OH; and when one of $R_7$ and $R'_7$ is $NH_2$, the other is not OH; and when one of $R_7$ and $R'_7$ is $N_3$, the other is not OH; $R_7''$ is alkyl or substituted alkyl.

$R_8$ is H, $OR_{14}$, $N_3$, $NH_2$, or F; and $R'_8$ is H, F, OH, O alkyl, alkyl, substituted alkyl, alkenyl, substituted alkenyl, alkynyl, or substituted alkynyl; or $R_8$ and $R'_8$ together may be =$CH_2$, =CHF; wherein both $R_8$ and $R'_8$ are not OH; and when one of $R_8$ and $R'_8$ is $NH_2$, the other is not OH; and when one of $R_8$ and $R'_8$ is $N_3$, the other is not OH;

$R_9$ is H, $CH_3$, $C_2H_5$, or $N_3$;

$R'_9$ is $CH_2OR_{14}$, $CH_2F$, $CH_2SH$, CHFOH, $CF_2OH$,

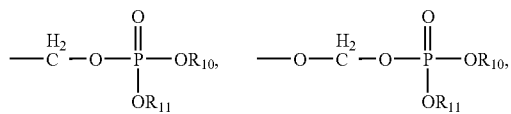

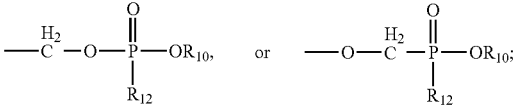

$R_{10}$ and $R_{11}$ are each independently H, alkyl, aryl, substituted aryl, acyloxyalkyl, or $(CH_2)_n$—O—$(CH_2)_mCH_3$;

$R_{12}$ is an N-linked amino acid residue (e.g. —NH—CH($CH_3$)$CO_2$alkyl or —NH—CH(isopropyl)-$CO_2$alkyl);

$R_{13}$ is H, $CH_3$, $C_2H_5$, $CH_2F$, $CH_2OH$, $CH_2CH_2F$, $CH_2CH_2OH$, $CH_2N_3$, $CH_2CH_2N_3$, $CH_2NH_2$, or $CH_2CH_2NH_2$; and $R_{14}$ is H.

In one embodiment, for a compound of formula I, $R_{14}$ is replaced to form a pharmaceutically acceptable prodrug, for example, a prodrug selected from the group consisting of: acyl, oxyacyl, phosphonate, phosphate, phosphate esters, phosphonamidate, phosphorodiamidate, phosphoramidate mono ester, cyclic phosphoramidate, cyclic phosphorodiamidate, phosphoramidate diester, $C(O)CHR_{15}NH_2$,

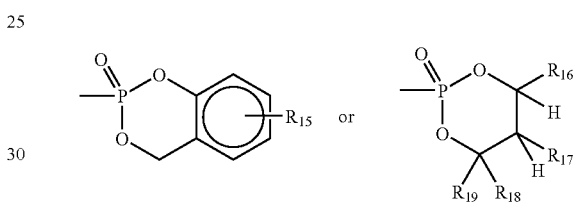

wherein:

$R_{15}$ is H, alkyl, substituted alkyl, aryl, substituted aryl, cycloalkyl, substituted cycloalkyl, heteroaryl, substituted heteroaryl, heterocyclic, substituted heterocyclic, or an amino acid;

$R_{16}$ is H, optionally substituted monocyclic aryl, or optionally substituted monocyclic heteroaryl; and $R_{17}$ is H, halogen, CN, —CO—$R_{20}$, —CON($R_{21}$)$_2$, —$CO_2R_{20}$, —$SO_2R_{20}$, —$SO_2N(R_{21})_2$, —$OR_{21}$, —$SR_{21}$, —$R_{21}$, —$N(R_{21})_2$, —O—$COR_{20}$, —O—$CO_2R_{20}$, —$SCOR_{20}$, —S—$CO_2R_{20}$, —$NHCOR_{21}$, —$NHCO_2R_{21}$, —$(CH_2)_p$—$OR_{22}$, or —$(CH_2)_p$—$SR_{22}$; or $R_{16}$ and $R_{17}$ are connected via an additional 3-5 atoms to form a cyclic group, optionally containing one heteroatom, that is fused to an aryl group at the beta and gamma position to the O attached to the phosphorus; or $R_{17}$ and $R_{18}$ are connected as described below;

$R_{18}$ and $R_{19}$ are each independently H, alkyl, aryl, heterocycloalkyl, aralkyl, optionally substituted monocyclic aryl or optionally substituted monocyclic heteroaryl; or $R_{18}$ and $R_{19}$ are connected via an additional 2-5 atoms to form a cyclic group, optionally containing 0-2 heteroatoms; or $R_{17}$ and $R_{18}$ are connected via an additional 3-5 atoms to form a cyclic group, optionally containing one heteroatom and $R_{19}$ is H, alkyl, aryl, heterocycloalkyl, aralkyl, optionally substituted monocyclic aryl or optionally substituted monocyclic heteroaryl; and $R_{20}$ is alkyl, aryl, heterocycloalkyl, or arylalkyl;

$R_{21}$ is H, alkyl, aryl, heterocycloalkyl, or arylalkyl;

$R_{22}$ is H or lower acyl;

n is an integer from 2-5;

m is an integer from 10-20; and p is an integer from 2-3.

In one embodiment of the invention, $R^2$ has the following formula:

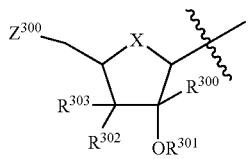

wherein:

$R^{300}$ is alkyl, substituted alkyl, alkenyl, substituted alkenyl, alkynyl, or substituted alkynyl;

$R^{301}$ is H, alkyl, —C(O)alkyl, or aryl-C(=O)—;

$R^{302}$ is H, OH, —Oalkyl, —OC(O)alkyl, benzoyloxy, —CH$_2$OH, CH$_2$NH$_2$, N$_3$, CH$_2$N$_3$, or NH$_2$;

$R^{303}$ is H, OH, or NH$_2$; provided both $R^{302}$ and $R^{303}$ cannot be the same group except hydrogen;

X is O, S, NH or CH$_2$;

$Z^{300}$ is —O—[P(=O)(R$^{307}$)O—]$_n$—R$^{308}$, or —CH$_2$—[P(=O)(R$^{307}$)O—]$_n$—R$^{308}$;

each $R^{307}$ is independently OH, —Oalkyl, or —OC(O)alkyl;

each $R^{308}$ is independently H, alkyl, or —C(O)alkyl; and n is 0, 1, 2, or 3.

In one embodiment of the invention, $R^2$ has the following formula:

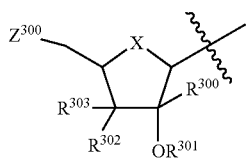

wherein: $R^{300}$ is H or methyl; $R^{301}$ is H; $R^{302}$ is OH; $R^{303}$ is H; X is O, S, NH or CH$_2$; $Z^{300}$ is —O—[P(=O)(R$^{307}$)O—]$_n$—R$^{308}$, or —CH$_2$—[P(=O)(R$^{307}$)O—]$_n$—R$^{308}$; each $R^{307}$ is OH; each $R^{308}$ is H; and n is 0, 1, 2, or 3.

In another embodiment of the invention, $R^2$ has the following formula:

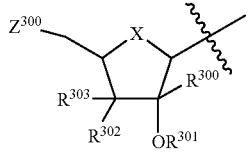

wherein: $R^{300}$ is H or alkyl; $R^{301}$ is H, alkyl, or benzoyl; $R^{302}$ is OH, or benzoyloxy, $R^{303}$ is H; X is O, S, NH or CH$_2$; $Z^{300}$ is —O—[P(=O)(R$^{307}$)O—]$_n$—R$^{308}$, or —CH$_2$—[P(=O)(R$^{307}$)O—]$_n$—R$^{308}$; each $R^{307}$ is OH; each $R^{308}$ is H; and n is 0, 1, 2, or 3.

In another embodiment of the invention, $R^2$ has the following formula:

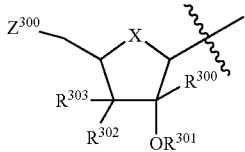

wherein: $R^{300}$ is H or methyl; $R^{301}$ is H, methyl, or benzoyl; $R^{302}$ is OH, or benzoyloxy, $R^{303}$ is H; X is O, S, NH or CH$_2$; $Z^{300}$ is —O—[P(=O)(R$^{307}$)O—]$_n$—R$^{308}$, or —CH$_2$—[P(=O)(R$^{307}$)O—]$_n$—R$^{308}$; each $R^{307}$ is OH; each $R^{308}$ is H; and n is 0, 1, 2, or 3.

In another embodiment of the invention, $R^2$ has the following formula:

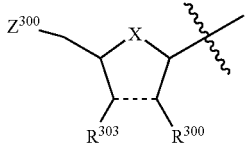

wherein: $R^{300}$ is H or alkyl; $R^{303}$ is H or alkyl; the bond represented by - - - is a single or a double bond; X is O, S, NH or CH$_2$; $Z^{300}$ is —O—[P(=O)(R$^{307}$)O—]$_n$—R$^{308}$, or —CH$_2$—[P(=O)(R$^{307}$)O—]$_n$—R$^{308}$; each $R^{307}$ is OH; each $R^{308}$ is H; and n is 0, 1, 2, or 3.

In another embodiment of the invention, $R^2$ has the formula: —CH$_2$CH$_2$OCH$_2$P(=O)(OH)$_2$,

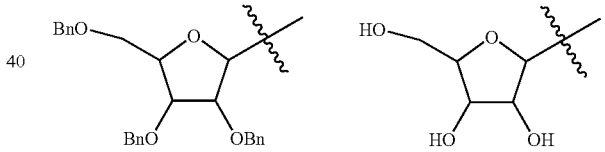

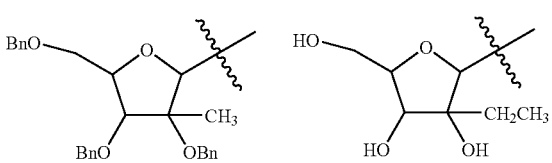

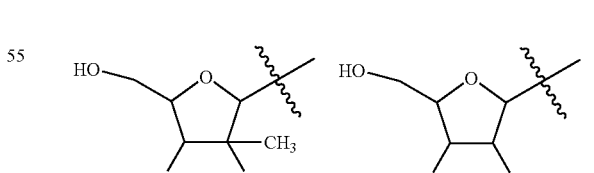

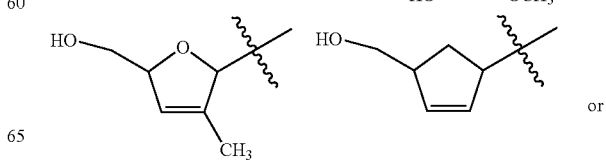

or

-continued

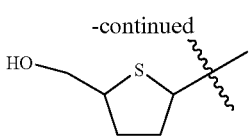

Synthetic Processes

Processes for preparing compounds of formula I, II, and III or pharmaceutically acceptable salts or prodrugs thereof, as well as processes for preparing intermediate compounds that can be used to prepare compounds of formula I, II, or III or pharmaceutically acceptable salts or prodrugs thereof are provided as further embodiments of the invention. For example in one embodiment the invention provides a method for preparing a pharmaceutically acceptable salt of compound of formula I, II, or III, comprising converting a corresponding compound of formula I, II, or III to the salt.

In another embodiment the invention provides a method for preparing a prodrug of a compound of formula I, II, or III, comprising converting a corresponding compound of formula I, II, or III to the prodrug.

In another embodiment the invention provides a method for preparing a compound of formula I, II, or III, comprising deprotecting a corresponding compound of formula I, II, or III that comprises one or more protecting groups to provide the compound of formula I, II, or III.

Synthetic Intermediates

The invention also provides synthetic intermediates that are useful for preparing compounds of formula I, II, or III. For example, the invention provides novel synthetic intermediates such as those described in the Examples herein.

In one embodiment the invention provides a compound of formula:

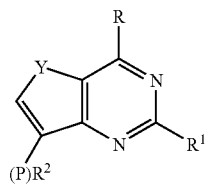

wherein: R is chloro or bromo; $R^1$ and Y have any of the values defined herein; and $(P)R^2$ is a nucleoside sugar group bearing one or more protecting groups.

In one embodiment, the invention provides the compound: 2-(3,4-Bis(benzyloxy)-5-(benzyloxymethyl)-tetrahydrofuran-2-yl)acetonitrile; 2-(6-((tert-Butyldiphenylsilyloxy)methyl)-2,2,3a-trimethyl-tetrahydrofuro[3,4-d][1,3]dioxol-4-yl)acetonitrile; 2-(3,4-Bis(benzyloxy)-5-(benzyloxymethyl)-3-methyl-tetrahydrofuran-2-yl) acetonitrile; 2-(3,4-Bis(benzyloxy)-5-(benzyloxymethyl)-3-methyl-tetrahydrofuran-2-yl)acetonitrile; 2-(4-(Benzyloxy)-5-(benzyloxymethyl)-3-methoxy-tetrahydrofuran-2-yl) acetonitrile; 2-(3-Methyl-5-(trityloxymethyl)-2,5-dihydrofuran-2-yl)acetonitrile; 2-(3,4-Bis(benzyloxy)-5-(benzyloxymethyl)-3-ethyl-tetrahydrofuran-2-yl) acetonitrile; Ethyl 3-amino-4-(3,4-bis(benzyloxy)-5-(benzyloxymethyl)-tetrahydrofuran-2-yl)furan-2-carboxylate; 3-Amino-4-(3,4-bis(benzyloxy)-5-(benzyloxymethyl)-tetrahydrofuran-2-yl)furan-2-carbonitrile; Ethyl 3-amino-4-(3,4-bis(benzyloxy)-5-(benzyloxymethyl)-3-methyl-tetrahydrofuran-2-yl)furan-2-carboxylate; 3-Amino-4-(3,4-bis(benzyloxy)-5-(benzyloxymethyl)-3-methyl-tetrahydrofuran-2-yl)furan-2-carbonitrile; 3-Amino-4-(3,4-bis(benzyloxy)-5-(benzyloxymethyl)-3-vinyl-tetrahydrofuran-2-yl)furan-2-carbonitrile; 3-Amino-4-(3,4-bis(benzyloxy)-5-(benzyloxymethyl)-3-ethyl-tetrahydrofuran-2-yl)furan-2-carbonitrile; 3-Amino-4-(3,4-bis(benzyloxy)-5-(benzyloxymethyl)-3-(hydroxymethyl)-tetrahydrofuran-2-yl)furan-2-carbonitrile; 3-Amino-4-(3-methyl-5-(trityloxymethyl)-2,5-dihydrofuran-2-yl)furan-2-carbonitrile; 3-Amino-4-(3,4-bis(benzyloxy)-5-(benzyloxymethyl)-2,5-dihydrofuran-2-yl)thiophene-2-carbonitrile; 3-Amino-4-(3,4-bis(benzyloxy)-5-(benzyloxymethyl)-3-methyl-tetrahydrofuran-2-yl) thiophene-2-carbonitrile; 3-Amino-4-(4-(benzyloxy)-5-(benzyloxymethyl)-3-methoxy-tetrahydrofuran-2-yl)furan-2-carbonitrile; 3-Amino-4-(3,4-bis(benzyloxy)-5-(benzyloxymethyl)-3-methyl-tetrahydrofuran-2-yl)furan-2-carboxamide; 3-Amino-4-(3,4-bis(benzyloxy)-5-(benzyloxymethyl)-tetrahydrofuran-2-yl)furan-2-carboxamide; 3-Amino-4-(3,4-bis(benzyloxy)-5-(benzyloxymethyl)-3-methyl-tetrahydrofuran-2-yl)furan-2-carbothioamide; 3-Amino-4-(3,4-bis(benzyloxy)-5-(benzyloxymethyl)-tetrahydrofuran-2-yl)furan-2-carbothioamide; 3-Amino-4-(4-(trityloxymethyl)cyclopent-2-enyl)furan-2-carbonitrile; 3-Amino-4-(5-(trityloxymethyl)-tetrahydrothiophen-2-yl)furan-2-carbonitrile; 3-Amino-4-(2-(trityloxy)ethyl)furan-2-carbonitrile; 2-Amino-7-(3,4-dihydroxy-5-(hydroxymethyl)-tetrahydrofuran-2-yl)furo[3,2-d] pyrimidin-4(3H)-one; or 7-(3,4-Dihydroxy-5-(hydroxymethyl)-3-methyl-tetrahydrofuran-2-yl)furo[3,2-d] pyrimidin-4(3H)-one; 7-β-(2',3',5'-Tri-O-benzyl-D-ribofuranosyl)-furo[3,2-d]pyrimidin-4(3H)-one; 4-Chloro-7-β-(2',3',5'-tri-O-benzyl-D-ribofuranosyl)-furo[3,2-d] pyrimidine; 7-β-(2',3',5'-Tri-O-benzyl-2'-C-methyl-D-ribofuranosyl)-furo[3,2-d]pyrimidin-4(3H)-one; 4-Chloro-7-β-(2',3',5'-tri-O-benzyl-2'-C-methyl-D-ribofuranosyl)-furo[3,2-d]pyrimidine; or 7-(2-(Trityloxy)ethyl)furo[3,2-d] pyrimidin-4-amine.

Isomers and Physical Forms

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixtures thereof, of a compound of the invention (e.g. a compound of formula I, II, or III), which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine anti-viral or anti-cancer activity using the standard tests described herein, or using other similar tests which are well known in the art. Although the invention includes all isomeric forms of the compounds described herein, one embodiment of the invention provides compounds having the absolute stereochemistry depicted in the Examples hereinbelow.

For example, it would be known in the field of chemistry that a compound of formula I:

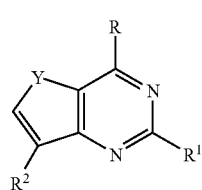

wherein R is OH would form a tautomer of the following formula:

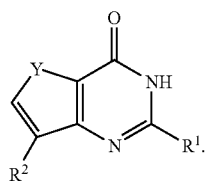

Accordingly, the invention includes all tautometric forms of the compounds of formulae I, II, and III.

Pharmaceutical Compositions, Modes of Administration and Methods of Treatment

The present disclosure provides compounds of the general formula (I, II, and III) as detailed above which are inhibitors of DNA and/or RNA viral polymerases and anticancer agents. Various forms of DNA and RNA viral polymerases are inhibited by the compounds disclosed, such as but not limited to viral RdRps. The compounds of the present disclosure therefore have utility in treating and/or preventing viral infections in a host and in treatment and/or preventing a variety of disease states and/or conditions caused by or related to such viral infections. In one embodiment, the compounds are useful in the above mentioned treating and/or preventing by inhibiting a viral RNA and DNA polymerases. Such viral agents include, but are not limited to, hepatitis B, hepatitis C, human immunodeficiency virus, Polio, Coxsackie A and B, Rhino, Echo, small pox, Ebola, and West Nile virus. In a particular embodiment, the causative agent of the viral infection is a flavivirus.

The present disclosure provides for a compound of the general formula (I, II, and III) and a pharmaceutical composition comprising a pharmaceutically effective amount of at least one compound of general formula (I, II, or III) as described herein. Such compounds and/or pharmaceutical compositions may be used in the manufacture of a medicament for treating and/or preventing a disease or condition in which it is desirable to inhibit a viral RNA and DNA polymerases. Such pharmaceutical compositions may also comprise a pharmaceutically acceptable carrier and other ingredients known in the art, or may comprise solely a compound of the general formula (I, II, and III).

The pharmaceutically acceptable carriers described herein, including, but not limited to, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The compounds described in the instant disclosure can be administered by any conventional method available for use in conjunction with pharmaceuticals, either as individual therapeutic agents or in combination with additional therapeutic agents.

The compounds described are administered in a pharmaceutically effective amount. The pharmaceutically effective amount of the compound and the dosage of the pharmaceutical composition administered will, of course, vary depending upon known factors, such as the pharmacodynamic characteristics of the particular agent and its mode and route of administration; the age, health and weight of the recipient; the severity and stage of the disease state or condition; the kind of concurrent treatment; the frequency of treatment; and the effect desired.

A daily dosage of active ingredient can be expected to be about 0.001 to 1000 milligrams (mg) per kilogram (kg) of body weight per day. In one embodiment, the total amount is between about 0.1 mg/kg and about 100 mg/kg of body weight per day; in an alternate embodiment between about 1.1 mg/kg and about 50 mg/kg of body weight per day; in yet another alternate embodiment between 0.1 mg/kg and about 30 mg/kg of body weight per day. The above described amounts may be administered as a series of smaller doses over a period of time if desired. The pharmaceutically effective amount can be calculated based on the weight of the parent compound to be delivered. If the salt or prodrug exhibits activity in itself, the pharmaceutically effective amount can be estimated as above using the weight of the salt or prodrug, or by other means known to those skilled in the art. The dosage of active ingredient may be given other than daily if desired.

The total amount of the compound administered will also be determined by the route, timing and frequency of administration as well as the existence, nature, and extent of any adverse side effects that might accompany the administration of the compound and the desired physiological effect. It will be appreciated by one skilled in the art that various conditions or disease states, in particular chronic conditions or disease states, may require prolonged treatment involving multiple administrations.

Dosage forms of the pharmaceutical compositions described herein (forms of the pharmaceutical compositions suitable for administration) contain from about 0.1 mg to about 3000 mg of active ingredient (i.e. the compounds disclosed) per unit. In these pharmaceutical compositions, the active ingredient will ordinarily be present in an amount of about 0.5-95% weight based on the total weight of the composition. Multiple dosage forms may be administered as part of a single treatment. The active ingredient may be administered to achieve peak plasma concentrations of the active ingredient of from about 0.2 to 70 μM, or from about 1.0 to 10 μM.

The active ingredient can be administered orally in solid dosage forms, such as capsules, tablets, and powders, or in liquid dosage forms, such as elixirs, syrups and suspensions. It can also be administered parenterally, in sterile liquid dosage forms. The active ingredient can also be administered intranasally (nose drops) or by inhalation via the pulmonary system, such as by propellant based metered dose inhalers or dry powders inhalation devices. Other dosage forms are potentially possible such as administration transdermally, via patch mechanisms or ointment.

Formulations suitable for oral administration can include (a) liquid solutions, such as a pharmaceutically effective amount of the compound dissolved in diluents, such as water, saline, or orange juice; (b) capsules, sachets, tablets, lozenges, and troches, each containing a predetermined pharmaceutically effective amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the patient, and aqueous and non-aqueous sterile suspensions that can include suspending agents, solubilizers, thickening agents, stabilizers, and preservatives. The compound can be administered in a physiologically acceptable diluent in a pharmaceutically acceptable carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly (ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl .beta.-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The compounds of the present invention, alone or in combination with other suitable components, can be made into aerosol formulations to be administered via inhalation. These aerosol formulations can be placed into pressurized acceptable propellants, such as dichlorodifluoromethane, propane, and nitrogen. Such aerosol formulations may be administered by metered dose inhalers. They also may be formulated as pharmaceuticals for non-pressured preparations, such as in a nebulizer or an atomizer.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutically acceptable carriers for injectable compositions are well known to those of ordinary skill in the art. See Pharmaceutics and Pharmacy Practice, J.B. Lippincott Co., Philadelphia, Pa., Banker and Chalmers, Eds., 238-250 (1982) and ASHP Handbook on Injectable Drugs, Toissel, 4th ed., 622-630 (1986).

Formulations suitable for topical administration include pastilles comprising the active ingredient in an inert base, such as gelatin and glycerin, or sucrose and acacia, as well as creams, emulsions, and gels containing, in addition to the active ingredient, such carriers as are known in the art. Furthermore, transdermal patches can be prepared using methods known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of administering a compound of the present invention to an patient are available, and, although more than one route can be used to administer a particular compound, a particular route can provide a more immediate and more effective reaction than another route.

Useful embodiments of pharmaceutical dosage forms for administration of the compounds according to the present invention can be illustrated as follows.

A large number of hard-shell capsules are prepared by filling standard two-piece hard gelatine capsules each with 100 mg of powdered active ingredient, 150 mg of lactose, 50 mg of cellulose and 6 mg of magnesium stearate.

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

A large number of tablets are prepared by conventional procedures so that the dosage unit is 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability or delay absorption.

Immediate release tablets/capsules are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Moreover, the compounds of the present invention can be administered in the form of nose drops, or metered dose and a nasal or buccal inhaler. The drug is delivered from a nasal solution as a fine mist or from a powder as an aerosol.

In one embodiment, the teachings of the present disclosure provide for the use of such pharmaceutical compositions and medicaments in a method of treating a viral infection or treating a disease state and/or condition caused by or related to such viral infection. In one embodiment, the treatment is the result of the inhibition of a viral RNA or DNA polymerase, such as but not limited to a RdRp. Such treatment or inhibition need not be complete to be useful. The method of treatment comprises the steps of: (i) identifying a patient in need of such treatment; (ii) providing such pharmaceutical composition containing at least one compound of the invention; and (iii) administering such pharmaceutical composition in a therapeutically effective amount to treat the viral infection in a patient in need of such treatment or to inhibit the activity of a viral RNA or DNA polymerase in a patient in need of such treatment.

In one embodiment, the teachings of the present disclosure provide for the use of such pharmaceutical compositions and medicaments in a method of preventing or suppressing a viral infection or preventing or suppressing a disease state and/or condition caused by or related to such viral infection. In one embodiment, the prevention or suppression is the result of the inhibition of a viral RNA or DNA polymerase, such as but not limited to a RdRp. Such prevention, suppression or inhibition need not be complete to be useful. The method of preventing or suppressing comprises the steps of: (i) identifying a patient in need of such prevention; (ii) providing such pharmaceutical composition containing at least one compound of the general formula (I, II, or III); and (iii) administering such pharmaceutical composition in a therapeutically effective amount to prevent or suppress the viral infection in a patient in need of such treatment or to inhibit the activity of a viral RNA and DNA polymerase in a patient in need of such treatment.

The methods of the treating and preventing a viral infection or a disease state and/or condition caused by or related to said viral infection may further comprise administering a therapeutically effective amount of a compound of the present invention in combination with a therapeutically effective amount of another anti-viral agent which, in particular, may be active against HCV. Agents active against HCV include, but are not limited to, ribavirin, levovirin, viramidine, thymosin alpha-1, an inhibitor of HCV NS3 serine protease, an inhibitor of inosine monophosphatedehydrognease, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a, interferon-α2b, a consensus interferon, and a purified interferon-α product.

The compounds and pharmaceutical compositions of the present disclosure can be administered to patients to prevent and/or treat a number of cancers. Cancers include, but are not limited to, leukemias and lymphomas such as acute lymphocytic leukemia, acute nonlymphocytic leukemias, chronic lymphocytic leukemia, chronic myelogenous leukemia, Hodgkin's Disease, non-Hodgkin's lymphomas, and multiple myeloma, childhood solid tumors such as brain tumors, neuroblastoma, retinoblastoma, Wilms Tumor, bone tumors, and soft-tissue sarcomas, common solid tumors of adults such as lung cancer, colon and rectum cancer, breast cancer, prostate cancer, urinary cancers, uterine cancers, oral cancers, pancreatic cancer, melanoma and other skin cancers, stomach cancer, ovarian cancer, brain tumors, liver cancer, laryngeal cancer, thyroid cancer, esophageal cancer, and testicular cancer. The cancer may be related to a viral infection or an activity of a viral DNA or RNA polymerase.

The methods of the treating and preventing cancer may also comprises further administering of a chemotherapeutic agent in combination with any of the compounds or pharmaceutical compositions of the present disclosure. Any suitable chemotherapeutic agent can be employed for this purpose. The chemotherapeutic agent is typically selected from the group consisting of alkylating agents, antimetabolites, natural products, hormonal agents, and miscellaneous agents.

Examples of alkylating chemotherapeutic agents include carmustine, chlorambucil, cisplatin, lomustine, cyclophosphamide, melphalan, mechlorethamine, procarbazine, thiotepa, uracil mustard, triethylenemelamine, busulfan, pipobroman, streptozocin, ifosfamide, dacarbazine, carboplatin, and hexamethylmelamine.

Examples of chemotherapeutic agents that are antimetabolites include cytosine arabinoside, fluorouracil, gemcitabine, hydroxyurea, mercaptopurine, methotrexate, azaserine, thioguanine, floxuridine, fludarabine, cladribine and L-asparaginase.

Examples of chemotherapeutic agents that are natural products include actinomycin D, bleomycin, camptothecins, daunomycin, doxorubicin, etoposide, mitomycin C, TAXOL™ (paclitaxel), taxotere, teniposide, vincristine, vinorelbine, mithramycin, idarubicin, MITHRACIN™. (plicamycin), and deoxycoformycin.

An example of a hormonal chemotherapeutic agent includes tamoxifen. Examples of the aforesaid miscellaneous chemotherapeutic agents include mitotane, mitoxantrone, vinblastine, and levamisole.

The ability of a compound to inhibit viral polymerases can be evaluated using known assays. The ability of a compound to inhibit HCV NS5B polymerase can be evaluated using the following assay.

HCV NS5B Polymerase Assay

Antiviral activity of the test compounds was assessed (Okuse et al., Antiviral Res. 2005, 65, 23-34) in the stably HCV RNA-replicating cell line, AVA5, derived by transfection of the human hepatoblastoma cell line, Huh7 (Blight et al., Sci. 2000, 290, 1972). Compounds were added to dividing cultures once daily for three days. Media was changed with each addition of compound. Cultures generally started the assay at 30-50% confluence and reached confluence during the last day of treatment. Intracellular HCV RNA levels and cytotoxicity were assessed 24 hours after the last dose of compound.

Triplicate cultures for HCV RNA levels (on 48-well and 96-well plates) and cytotoxicity (on 96-well plates) were used. A total of six untreated control cultures, and triplicate cultures treated with α-interferon and ribavirin served as positive antiviral and toxicity controls.

Intracellular HCV RNA levels were measured using a conventional blot hybridization method in which HCV RNA levels are normalized to the levels of B-actin RNA in each individual culture (Okuse et al., Antivir. Res. 2005, 65, 23-34). Cytotoxicity was measured using a neutral red dye uptake assay (Korba and Gerin, Antivir. Res. 1992, 19, 55). HCV RNA levels in the treated cultures are expressed as a percentage of the mean levels of RNA detected in untreated cultures.

Representative compounds of formulae I, II, and III demonstrated significant activity in this assay.

Compound Synthesis

Compound of formula I, II, and III can be prepared using synthetic intermediates and synthetic procedures that are known, or they can be prepared using the synthetic intermediates and synthetic procedures identified in Schemes A1-D2, and the accompanying Examples herein. The following abbreviations are used herein.

Tr: trityl
Bn: benzyl
TBDPS: tert-butyldiphenylsilyl
m-CPBA: 3-chloroperoxybenzoic acid
TFA: trifluoroacetic acid
TBDMSCl: tert-butyldimethylsilyl chloride
DMF: dimethylformamide
THF: tetrahydrofuran
LDA: lithium diisopropylamine
TEAB: triethylammonium bicarbonate
mMTrCl: monomethoxytrityl chloride
DMAP: dimethylaminopyridine
DEAE: diethylaminoethyl-sepharose
CMA-80: Chloroform 80:MeOH 18:NH$_4$OH:2
CMA-50: Chloroform 50:MeOH 40:NH$_4$OH:10
Bz: benzoyl
BnBr: benzyl bromide
LiHMDS: lithium hexamethyldisalazane
TBDPSCl: tert-butyldiphenylsilyl chloride
DMSO: dimethylsulfoxide
RMgBr: alkyl magnesium bromide
DIBAL: diisobutylaluminum hydride
DBN: 1,5-diazabicyclo[4.3.0]non-5-ene
DBU: 1,8-diazabicyclo[5.4.0]undec-7-ene
MeMgBr: methylmagnesium bromide Preparation of R$^2$—CH$_2$CN Compounds:

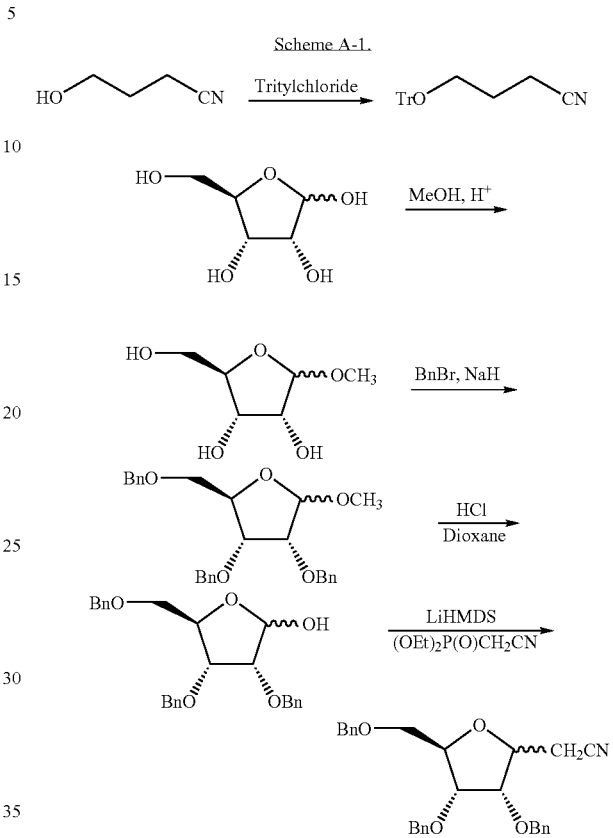

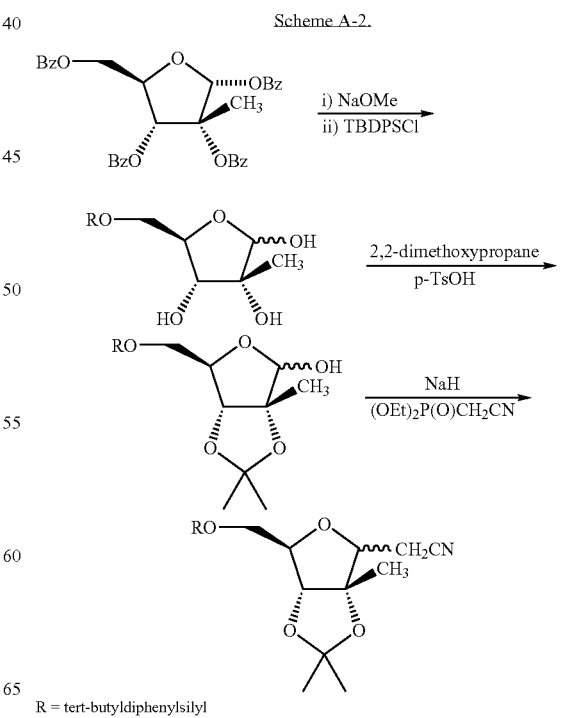

Scheme A-3.
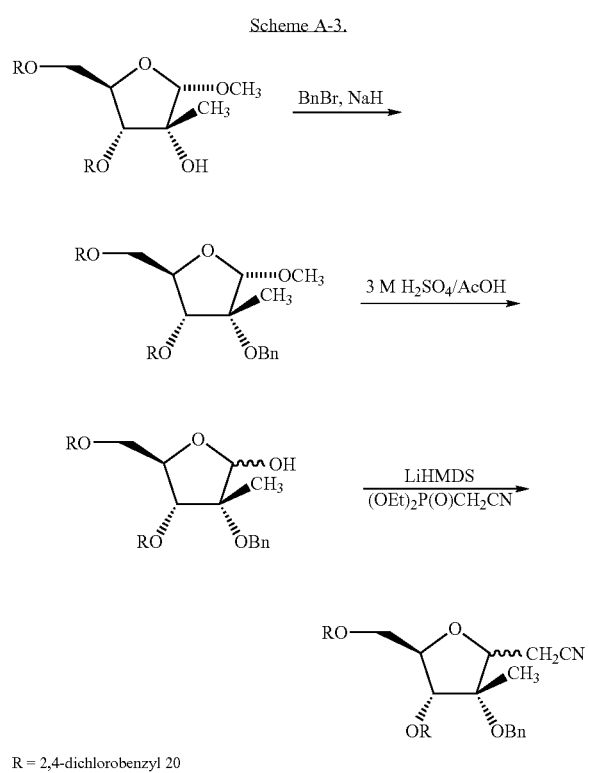
R = 2,4-dichlorobenzyl 20
Scheme A-4.
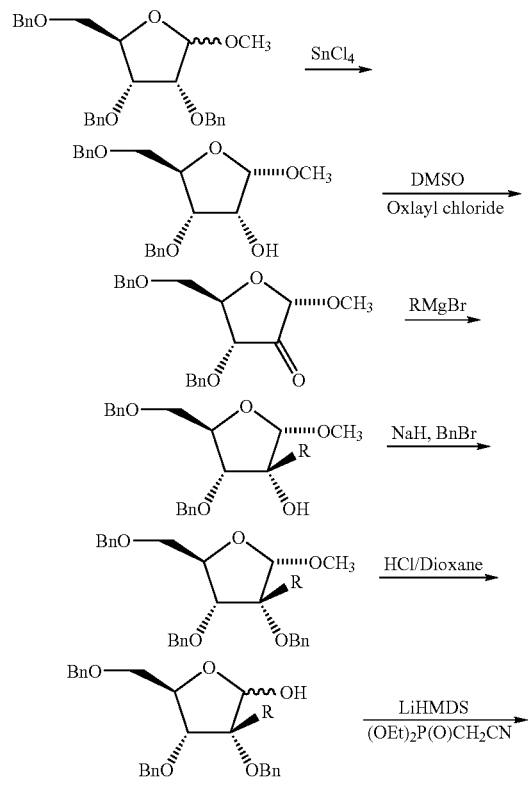
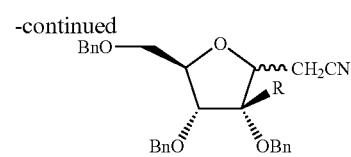
R = CH₃, C₂H₅, CH=CH₂
Scheme A-5.
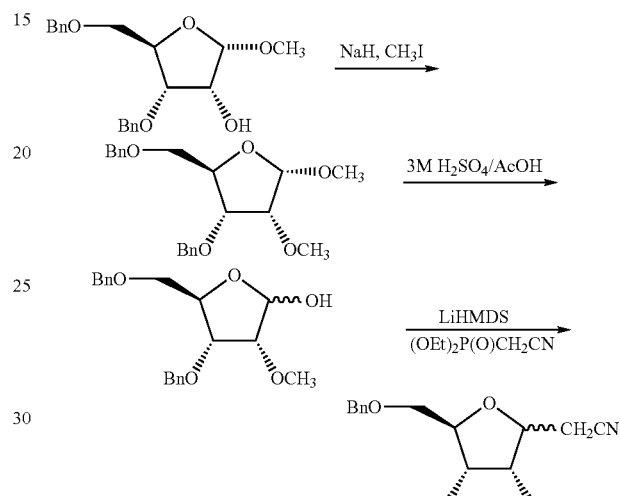
Scheme A-6.
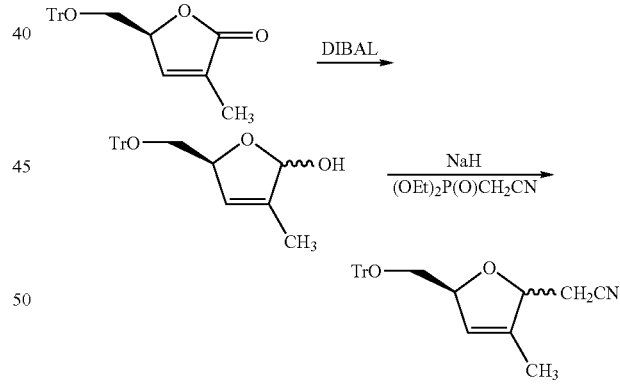
Scheme A-7.
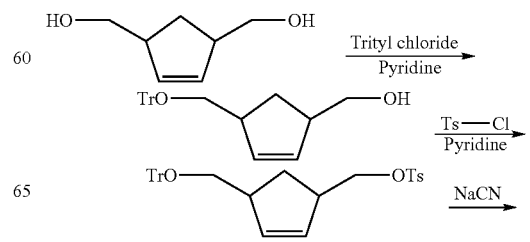

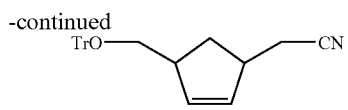

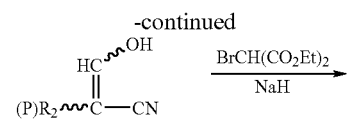

Scheme A-8.

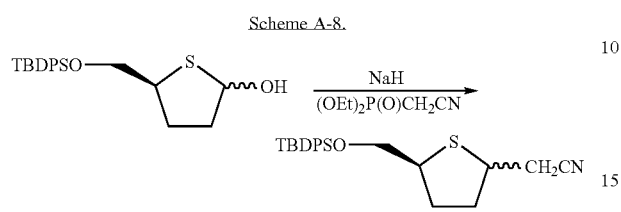

Preparation of Compounds of the Invention from $R^2CH_2CN$ Intermediates

In the following schemes, $R^2$ is a nucleoside sugar group (e.g. a substituted tetrahydro or dihydrofuranyl; a substituted tetrahydro or dihydrothiophenyl; a substituted alkyl, substituted cycloalkyl or cycloalkenyl; a substituted pyrrolidinyl; or a substituted dioxolanyl, thioxolanyl or dithiolanyl). $(P)R^2$ is a nucleoside sugar group bearing one or more protecting groups.

Scheme B-1.

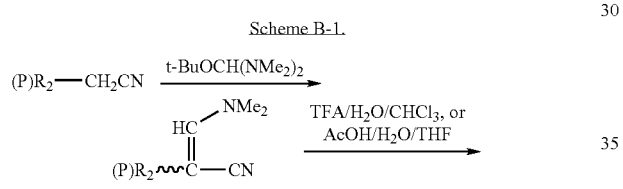

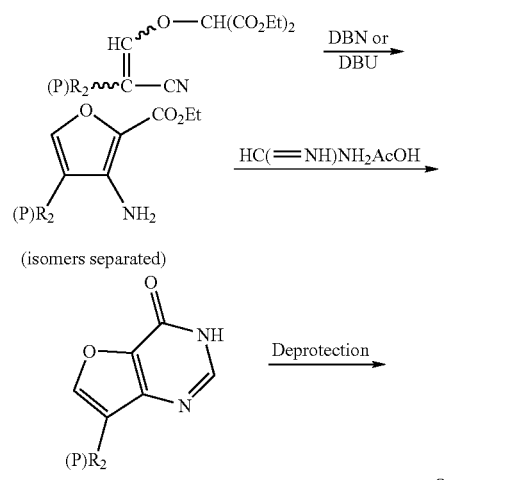

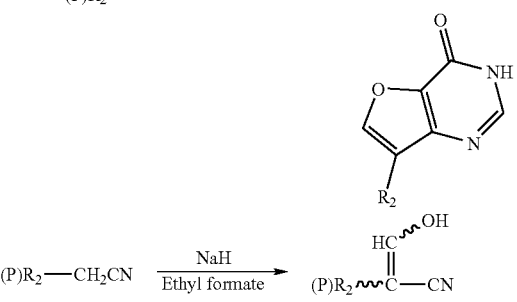

(P) = Protecting group

Scheme B-2.

Scheme B-3.

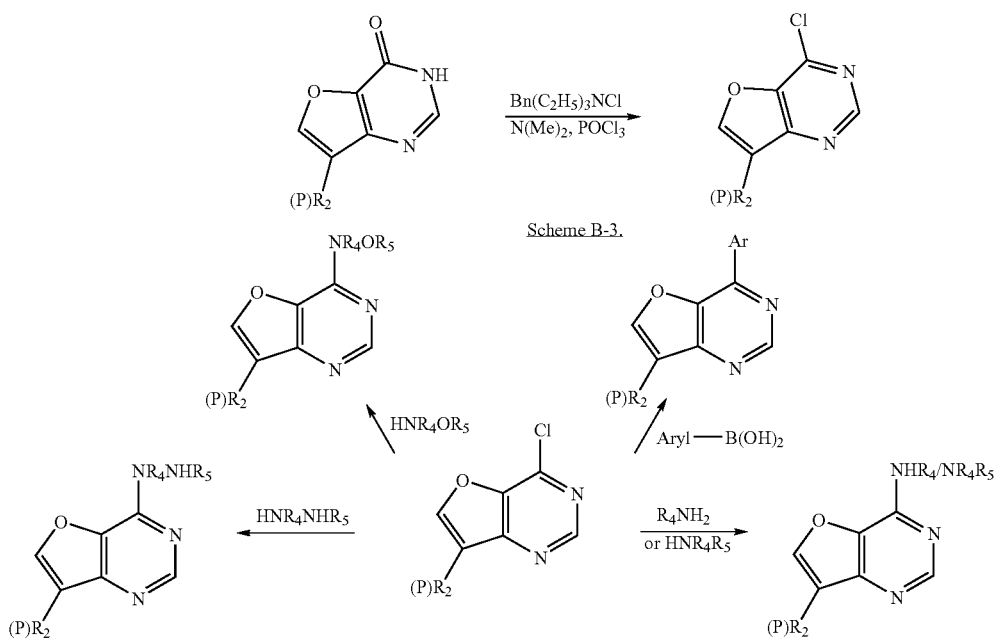

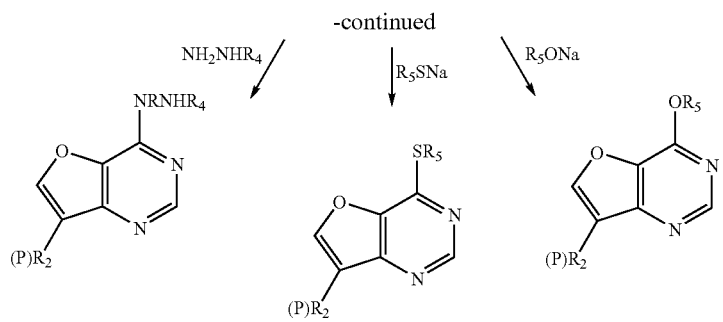
Deprotection of protecting groups in $R_2$ gives the target molecules
$NR_4R_5$=Azetidine, pyrrolidine
$R_4, R_5$=H, $CH_3$, $C_2H_5$, n-$C_3H_7$, i-$C_3H_7$,
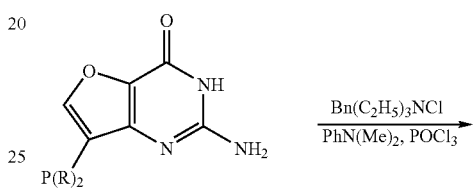
,
$CH_2CH_2OH$, $CH_2CH_2NH_2$, $NH_2(CH_2)_nNH_2$
Scheme B-4.
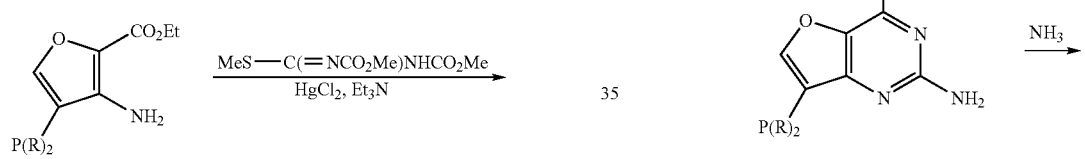
Scheme B-5.
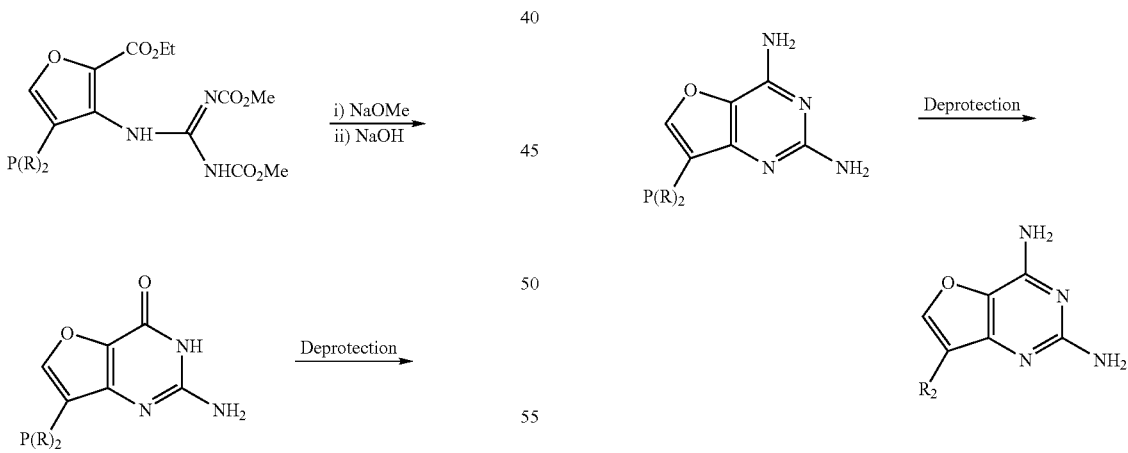
Scheme B-6.
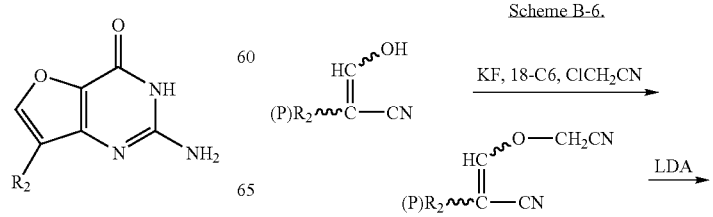

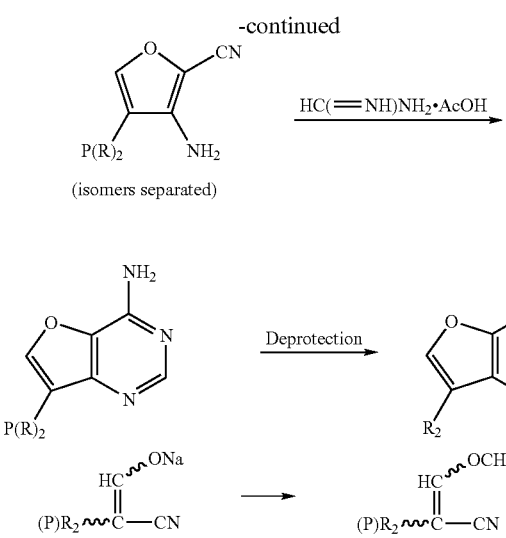
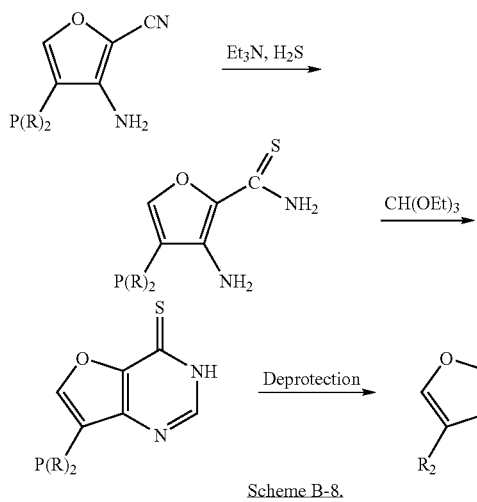
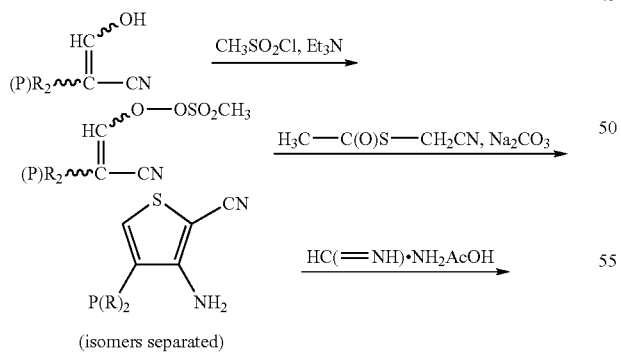
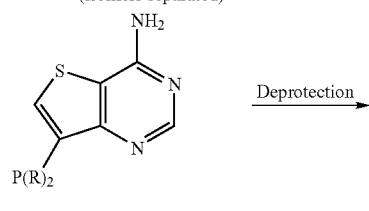
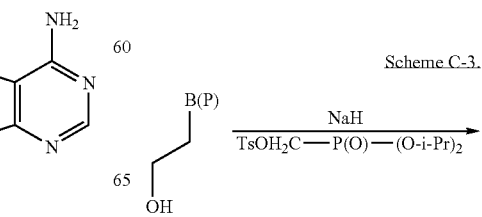

Preparation of Monophosphates and Triphosphates of Nucleosides (Represented by Examples C-1 to C-6)

The following Schemes illustrate the preparation of compounds of formula I, II, and III that have one or more phosphate groups. In these Schemes, B represents the furopyrimidine or thienopyrimidine base of formula I, and B(P) represents the furopyrimidine or thienopyrimidine base of formula I, bearing one or more protecting groups.

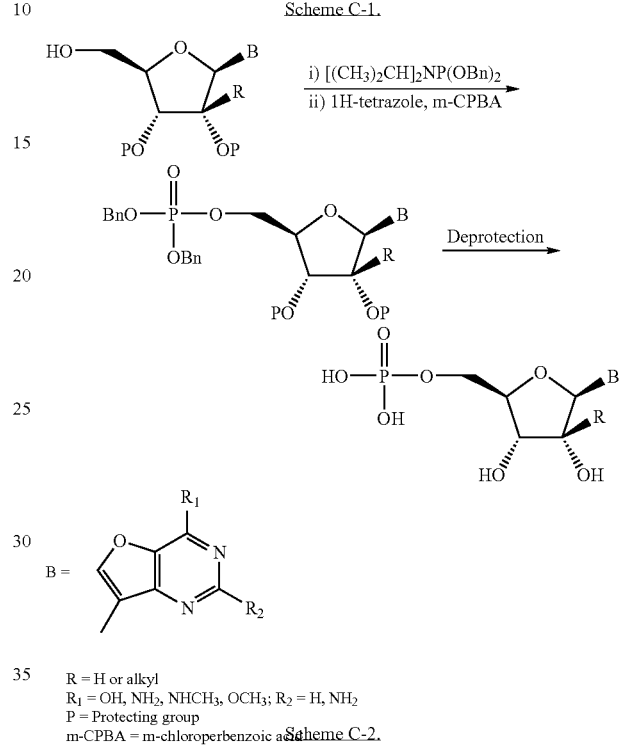

R = H or alkyl
$R_1$ = OH, $NH_2$, $NHCH_3$, $OCH_3$; $R_2$ = H, $NH_2$
P = Protecting group
m-CPBA = m-chloroperbenzoic acid Scheme C-2.

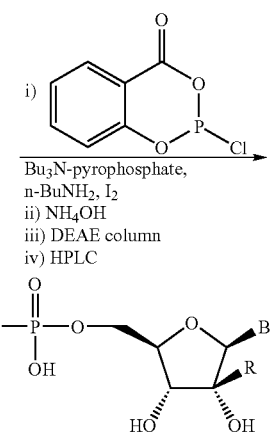

B and R are the same as in Scheme C-1

Scheme C-3.

-continued
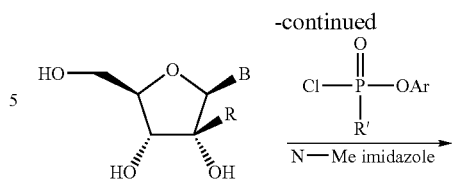
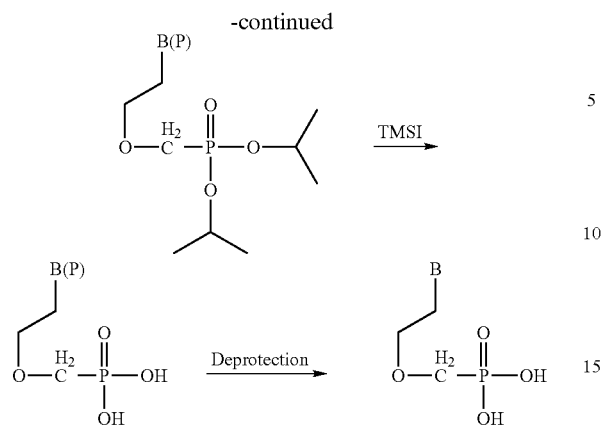
Preparation of Prodrugs
The following Schemes illustrate the preparation of prodrugs of the invention.
Scheme D-1.
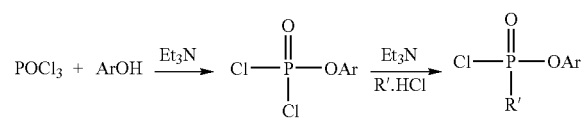
B and R are the same as in Scheme C-1
R' = aminoacid ester
Scheme D-2.
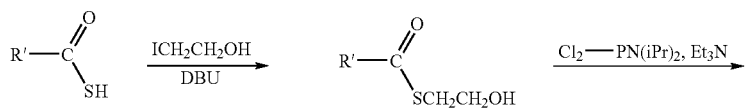
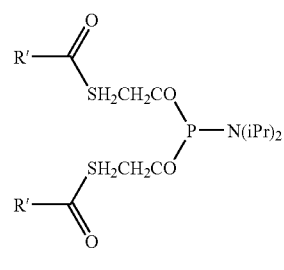
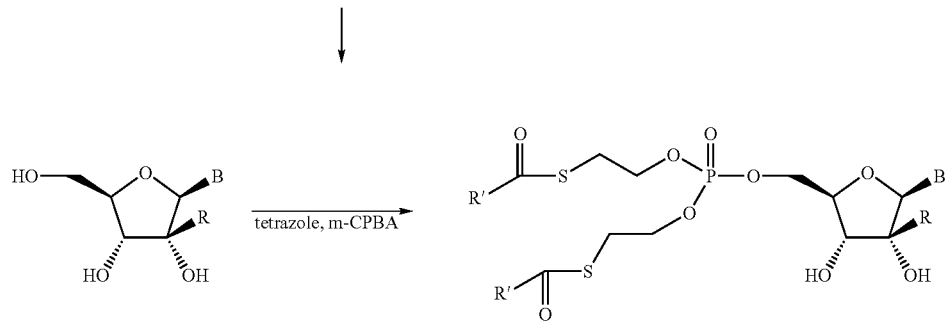
B and R are the same as in Scheme C-1
R' = CH$_3$, C(CH$_3$)$_3$ The invention will now be illustrated by the following non-limiting Examples.

EXAMPLES

Example A-1

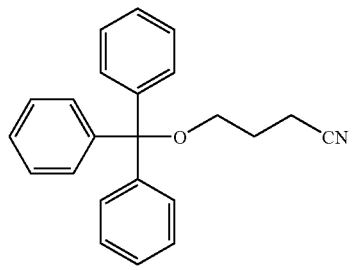

4-(Trityloxy)butanenitrile (Scheme A-1)

To a solution of 3-cyano-1-n-propanol (16.85 g, 198 mmol, prepared by method of Blicke, et al., J. Org. Chem. 1961, 26, 3685) in dichloromethane (250 mL) were added triethylamine (80.1 g, 792 mmol) and trityl chloride (82.8 g, 297 mmol) at room temperature and the mixture was stirred for 16 h. To the reaction mixture was added methanol (25 mL) and stirred for 1 h. After concentration, the residue was purified on a column of silica gel using ethyl acetate and hexanes as eluent to give 40 g (61.7%) of the desired product.

$^1$HNMR (DMSO-$d_6$): δ 7.15-7.40 (m, 15H), 3.01-3.12 (m, 2H), 2.51-2.64 (m, 2H), 1.75-1.90 (m, 2H).

Example A-2

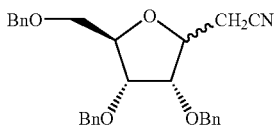

2-(3,4-Bis(benzyloxy)-5-(benzyloxymethyl)-tetrahydrofuran-2-yl)acetonitrile (Scheme A-1)

Step 1: To a solution of D-ribose (61 g, 406.66 mmol) in methanol (1 L) was added conc. sulfuric acid (6.1 mL) and stirred at 4° C. for 16 h. The reaction mixture was neutralized using triethylamine (40 mL), concentrated to dryness and co-distilled twice with 200 mL of toluene to remove trace amount of water. This furnished 72 g of crude O-methyl-D-ribofuranose, which was used as such for next step.

Step 2: To a slurry of NaH (65 g, 60%, 1.626 mol) in DMF (200 mL) was added crude compound from Step 1 (72 g, 406.66 mmol) in DMF (800 mL) over a period of 0.5 h, maintaining the temperature below 5° C. The anion formed was stirred at room temperature for 30 min. Benzyl bromide (219.1 g, 1280.9 mmol) was added dropwise over a period of 1 h maintaining temperature between 0-5° C. The reaction was stirred at room temperature for 12 h (TLC analysis in 30% ethyl acetate/hexane showed complete disappearance of starting material), was diluted with water (500 mL) and extracted with ethyl acetate (2×1 L). The combined organic extracts were washed twice with water (1 L), brine (500 mL), and dried over MgSO$_4$ and filtered. The filtrate was concentrated under vacuum to furnish crude residue. The crude residue was purified by flash chromatography (silica gel 1 kg), eluting with ethyl acetate in hexanes to furnish 112 g (63.3%) of desired product as an oil.

$^1$H NMR (DMSO-$d_6$): δ 7.36-7.27 (m, 15H), 4.92 (s, 1H), 4.66-4.44 (m, 6H), 4.12-4.07 (m, 1H), 3.97 (dd, J=6.78 and 4.5 Hz, 1H), 3.91 (d, J=4.5 Hz, 1H), 3.55 (dd, J=10.73 and 3.4 Hz, 1H), 3.42 (dd, J=10.7 and 6.0 Hz, 1H), 3.21 (s, 3H).

Step 3: To a solution of product from Step 2 (114 g, 262.35 mmol) in dioxane (250 mL) was added 4 N HCl (250 mL) and heated at reflux for 4 h. The reaction mixture was allowed to attain room temperature and diluted with ethyl acetate (1.5 L). The aqueous layer was separated and extracted with ethyl acetate (3×1 L). The organic layers were combined, washed with water (2×500 mL), saturated aqueous NaHCO$_3$ (250 mL), water (500 mL), and brine (250 mL), and dried over MgSO$_4$ and filtered. The filtrate was concentrated under vacuum to furnish crude product. The crude product was purified by flash chromatography (silica gel 1.5 kg, eluting with ethyl acetate in hexanes 0 to 30%) to furnish starting material (9.9 g,) and 85.3 g (45%) of desired product (mixture of isomers) as an oil.

$^1$H NMR (DMSO-$d_6$): δ 7.32-7.25 (m, 15H), 6.57 (d, J=4.8 Hz, 0.7H, D$_2$O exchangeable), 5.82 (d, J=7.7 Hz, 0.3H), 5.26 (dd, J=7.7, 3.5 Hz, 0.3H), 5.21 (dd, J=4.8, 1.3 Hz, 0.7H), 4.70-4.43 (m, 6H), 4.16 (q, J=4.1 Hz, 0.3H), 4.06-3.96 (m, 1.3H), 3.93-3.87 (m, 0.7H), 3.80 (dd, J=4.3, 1.5 Hz, 0.7H), 3.58-3.41 (m, 2H);

Step 4: To a stirred solution of product from Step 3 (15 g, 35.67 mmol) in THF (150 mL) was added diethyl (cyanomethyl)phosphonate (6.95 g, 39.23 mmol) at room temperature followed by lithium bis(trimethylsilyl)amide (39.2 mL, 1M solution in THF) addition at −78° C. The reaction mixture was stirred at −78° C. for about 20 min and at 0° C. for 1.5 h and then was quenched by adding water (50 mL). The reaction was extracted with ether (2×200 mL), washed with water (2×50 mL), brine (1×50 mL), and dried over MgSO$_4$. After filtration, the filtrate was concentrated and purified by flash chromatography using 0 to 30% ethyl acetate in hexanes to give 10.79 g (68.2%) of desired compound as a mixture of isomers as an oil.

MS (ES$^+$) 444.33 (M+1).

Example A-3

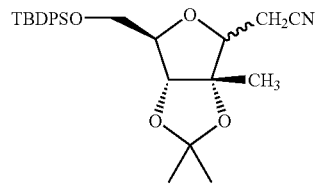

2-(6-((tert-Butyldiphenylsilyloxy)methyl)-2,2,3a-trimethyl-tetrahydrofuro[3,4-d][1,3]dioxol-4-yl)acetonitrile (Scheme A-2)

Step 1: A solution of 2'-C-methyl-1,3,5-tribenzoylribofuranose (19.1 g, 40.09 mmol, prepared according to literature procedures (a) Harry-O'kuru et. al., J. Org. Chem. 1997, 62, 1754-1759 and (b) Du, J. et. al. Nucleosides &Nucleotides, 1999, 18, 187-195) in MeOH (850 mL) was treated with NaOMe (25 wt % in MeOH, 55 mL, 240.35 mmol) followed by stirring at room temperature for 2.5 h. The reaction mixture was neutralized with conc. HCl until pH reached between 7 and 8 and concentrated to dryness. The residue was treated with MeOH (300 mL), stirred, filtrated to remove insolubles, and the filtrate was concentrated. The residue was treated with water (400 mL) and extracted with EtOAc (2×200 mL). The aqueous phase was concentrated to dryness to give 11.64 g of yellow syrup. Part of the syrup (474 mg) was treated with DMF (6 mL), imidazole (325 mg, 4.77 mmol), and TBDPSCl (0.50 mL, 1.92 mmol) followed by stirring at room temperature for 22 h. The reaction mixture was diluted with EtOAc (100 mL) and washed with water (2×50 mL), brine (50 mL), and dried over MgSO$_4$. After filtration, the filtrate was concentrated and the residue was purified on a silica gel column using hexanes:ethyl acetate (1:0 to 1:1) as eluent to give 293 mg (45%, two steps) of product as a colorless oil.

$^1$H NMR (a mixture of anomeric isomers, ratio=1:3, CDCl$_3$): δ 7.70-7.62 (m, 4H), 7.45-7.34 (m, 6H), 5.07, 5.03 (s, s, 1H), 4.15-3.69 (m, 4H), 1.36, 1.31 (s, s, 3H), 1.07, 1.05 (s, s, 9H). MS (ES$^+$) 425.41 (M+Na).

Step 2: A mixture of compound from Step 1 (7.2 g, 17.89 mmol), dimethoxypropane (27 mL, 98%, 0.22 mol), p-TsOH (160 mg, 0.84 mmol) in acetone (80 mL) was stirred at room temperature for 1 h. The reaction mixture was treated with EtOAc (800 mL), water (500 mL), saturated NaHCO$_3$ (30 mL), and the organic layer was separated. The aqueous phase was further extracted with EtOAc (500 mL). The combined organic extracts were washed with water (2×300 mL), brine (300 mL), and dried over MgSO$_4$. After filtration, the filtrate was concentrated and the residue was purified on a silica gel column using hexanes:ethyl acetate (1:0 to 10:1) as eluent to give 6.16 g (58%) of desired product with some inseparable undesired compound as a colorless oil which was used as such for the next step.

Step 3: A suspension of NaH (60%, 760 mg, 19 mmol) in DME (65 mL) was cooled to 0° C. and treated with diethyl cyanomethylphoshonate (3.1 mL, 19 mmol) dropwise. After stirring for 10 min at about 0° C., the mixture was treated dropwise with a solution of product from Step 2 (4.2 g, 9.49 mmol) in DMF (25 mL) followed by stirring at room temperature for 2 h. The reaction mixture was treated with ether (500 mL) and water (250 mL) and organic layer was separated. The aqueous phase was further extracted with ether (250 mL) and the combined organic extracts were washed with water (2×250 mL), and dried over MgSO$_4$. After filtration, the filtrate was concentrated and the residue was purified on a silica gel column using hexanes:ethyl acetate (1:0 to 10:1) as eluent to give 2.84 g (50%, two steps) of 2-(6-((tert-butyldiphenylsilyloxy)methyl)-2,2,3a-trimethyl-tetrahydrofuro[3,4-d][1,3]dioxol-4-yl)acetonitrile as a colorless oil.

$^1$H NMR (CDCl$_3$): δ 7.76-7.60 (m, 4H), 7.59-7.49 (m, 6H), 4.59 (bs, 1H), 4.15-4.03 (m, 2H), 3.84-3.73 (m, 2H), 2.93 (dd, J=16.8, 4.5 Hz, 1H), 2.70 (dd, J=16.7, 8.1 Hz, 1H), 1.46 (s, 3H), 1.44 (s, 3H), 1.42 (s, 3H), 1.08 (s, 9H). MS (ES$^+$) 488.35 (M+Na).

Example A-4

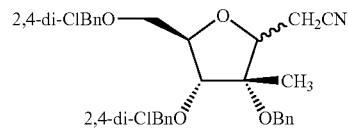

2-(3-(Benzyloxy)-4-(2,4-dichlorobenzyloxy)-5-((2,4-dichlorobenzyloxy)methyl)-3-methyl-tetrahydrofuran-2-yl)acetonitrile (Scheme A-3)

Step 1: A solution of 3,5-bis-O-(2,4-dichlorophenylmethyl)-2-C-β-methyl-1-O-methyl-α-D-ribofuranose (20.11 g, 40.53 mmol, prepared according to literature procedures a) Martin, P., Helvetica Chimica Acta, 1995, 78, 486-504 and b) Eldrup et al., J. Med. Chem. 2004, 47, 5284-5297) in THF (500 mL) was treated with NaH (60%, 6.45 g, 161.25 mmol) and stirred at room temperature for 0.5 h followed by addition of BnBr (14.6 mL, 122.74 mmol) over 10 min. The reaction mixture was stirred at 70° C. overnight and diluted with EtOAc (2 L), washed with water (2×) and brine, and dried over MgSO$_4$. After filtration, the filtrate was concentrated and the residue was purified on a silica gel column using hexanes:ethyl acetate (1:0 to 4:1) as eluent to give 16.2 g (68%) of desired product as a yellow oil.

$^1$H NMR (DMSO-d$_6$): δ 7.70-7.25 (m, 11H), 4.85-4.50 (m, 7H), 4.20-4.13 (m, 1H), 3.76-3.67 (m, 3H), 3.37 (s, 3H), 1.40 (s, 3H); IR (neat, cm$^{-1}$) 2904, 1591, 1472, 1199, 1102; Anal. Calcd for C$_{28}$H$_{28}$Cl$_4$O$_5$: C, 57.36; H, 4.81; Cl, 24.19. Found: C, 57.23; H, 4.65; Cl, 24.32; MS (ES$^+$) 609.07 (M+Na).

Step 2: A mixture of product from Step 1 (15.19 g, 25.91 mmol) and 3M H$_2$SO$_4$/HOAc (1:4, 150 mL) was heated at 70° C. for 9 h. The reaction mixture was diluted with chloroform (500 mL) and washed with water (2×), 1M NaHCO$_3$, water, and dried over MgSO$_4$. After filtration, the filtrate was concentrated and the residue was purified on a silica gel column using hexanes:ethyl acetate (1:0 to 4:1) as eluent to give 8.6 g (58%) of desired product as a light yellow oil.

$^1$H NMR (a mixture of anomeric isomers, ratio=5:4, DMSO-d$_6$): δ 7.80-7.40 (m, 11H), 6.86 and 6.23 (2d, J=4.8 and 6.3 Hz, 1H), 6.23 (J=6.3 Hz) (2d, 1H), 5.25-5.19 (m, 1H), 4.95-4.70 (m, 6H), 4.42-3.75 (m, 4H), 1.55, 1.53 (2s, 3H); IR (neat, cm$^{-1}$) 3435, 2916, 2873, 1591, 1472, 1384, 1095; MS (ES$^+$) 593.03 (M+Na); Anal. Calcd for C$_{27}$H$_{26}$Cl$_4$O$_5$: C, 56.66; H, 4.58; Cl, 24.78. Found: C, 56.44; H, 4.48; Cl, 24.76.

Step 3. A solution of product from Step 2 (4.25 g, 7.43 mmol) in THF (35 mL) was cooled to −78° C. and treated with diethyl cyanomethylphoshonate (3.6 mL, 22.25 mmol) followed by addition of 1M lithium bis(trimethylsilyl)amide (9 mL). The reaction mixture was warmed to room temperature and stirred for 21 h. It was diluted with ether (400 mL) and water (200 mL) and the organic layer was separated. The aqueous phase was further extracted with ether (200 mL). The combined organic extracts were washed with water (2×) and dried over MgSO$_4$. After filtration, the filtrate was concentrated and the residue was purified on a silica gel column using hexanes:ethyl acetate (1:0 to 4:1) as eluent to give 3.9 g (88%) of desired product as a colorless oil.

$^1$H NMR (a mixture of anomeric isomers, ratio=3:2, DMSO-d$_6$): δ 7.53-7.10 (m, 11H), 4.71-4.43 (m, 7H), 4.07-

3.75 (m, 2H), 3.62-3.48 (m, 2H), 2.77-2.54 (m, 2H), 1.35, 1.21 (2s, 3H); IR (neat, cm$^{-1}$) 2879, 2252, 1591, 1472, 1383, 1095; MS (ES$^+$) 618.13 (M+Na) Anal. Calcd for $C_{29}H_{27}Cl_4NO_4$: C, 58.51; H, 4.57; N, 2.35. Found: C, 58.31; H, 4.49; N, 2.27.

Example A-5

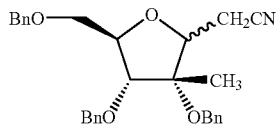

2-(3,4-Bis(benzyloxy)-5-(benzyloxymethyl)-3-methyl-tetrahydrofuran-2-yl)acetonitrile (Scheme A-4)

Step 1: To a solution of the compound from Step 2 of Example A-2 (111 g, 255.45 mmol) in $CH_2Cl_2$ (800 mL) at −20° C. was added dropwise a solution of stannic chloride (280.99 mL, 1M solution in $CH_2Cl_2$, 280.99 mmol) over a period of 30 min while stirring and maintaining the temperature between −20 and −10° C. After the solution was kept at 0° C. for 23 h, the reaction mixture was quenched carefully by the addition of saturated $NaHCO_3$ solution (1 L) over a 10-min period. Tin salts were removed via filtration through Celite®, and from the filtrate the organic phase was separated. The aqueous layer was extracted with chloroform (1000 mL). The combined organic extracts were washed twice with water (500 mL) and brine (200 mL), and dried over $MgSO_4$. After filtration, the filtrate was concentrated to furnish crude product as dark yellow oil. The crude oil was purified by flash chromatography (silica gel 1 kg, eluting with ethyl acetate in hexanes) to furnish 78.7 g (89.5%) of 4-(benzyloxy)-5-(benzyloxymethyl)-2-methoxy-tetrahydrofuran-3-ol as an oil.

$^1$H NMR (DMSO-d$_6$): δ 7.35-7.26 (m, 10H), 4.77 (d, J=4.3 Hz, 1H), 4.56 (dd, J=42.8 and 12.4 Hz, 2H), 4.46 (bs, 2H), 4.06 (dd, J=8.3 and 4.3 Hz, 1H), 3.98 (dd, J=6.6 and 4.7 Hz, 1H), 3.68 (dd, J=6.6 and 3.8 Hz, 1H), 3.44 (d, J=4.5 Hz, 2H), 3.30 (bs, 3H); IR (neat) 3554.8, 3030.7, 2926.0, 2912.0, 2863.2, 1957.1, 1732.1, 1650.4, 1494.8, 1452.4, 1414.7, 1362.0, 1323.2, 1269.2, 1187.7, 1124.5, 1095.7, 1040.0, 914.4, 853.3, 738.8 and 698.5 cm$^{-1}$; MS (ES$^+$) 367.38 (M+Na); Anal. Calcd for $C_{20}H_{24}O_5$: C, 69.74; H, 7.02. Found: C, 69.84; H, 7.00.

Step 2: A solution of DMSO (45.05 g, 576.66 mmol) in anhydrous $CH_2Cl_2$ (150 mL) was added dropwise to a solution of oxalylchloride (36.88 g, 290.5 mmol) at −78° C. with stirring over a period of 30 min (maintaining the internal temperature below −65° C. during addition). To this was added dropwise a solution of compound from Step 1 in $CH_2Cl_2$ (150 mL) over a period of 30 min. The reaction mixture was stirred at −70° C. for 3.5 h and quenched by dropwise addition of triethylamine (113.08 g, 1117.5 mmol) at −70° C. over 30 min. The reaction mixture was allowed to warm to room temperature and diluted with water (500 mL). The organic layer was separated and aqueous layer was extracted with chloroform (2×500 mL). The combined organic layers were washed with water (1 L), brine (1 L), and dried over $MgSO_4$. After filtration, the filtrate was concentrated and the residue was dried under vacuum to furnish 79 g of the product as a light yellow syrup. This compound was used as such without further purification for the next step.

Step 3: A solution of MeMgBr (3M in ether, 263.5 mL, 790.5 mmol) was added dropwise to a solution of compound from Step 2 (76.4 g, 223.5 mmol) in anhydrous diethyl ether at −70° C. over a period of 2 h (maintaining the inside temperature around −70° C.). The reaction was stirred at the same temperature for 2.5 h (TLC analysis using 30% ethyl acetate in hexanes of an aliquot showed completion of reaction). The reaction mixture was quenched by pouring into ice cold water (3 L) and neutralized with 1N HCl (750 mL) to pH 6-7. The aqueous layer was separated and extracted once with ethyl acetate (2 L). The combined organic layers were washed with water (2×1 L), saturated $NaHCO_3$ (2×200 mL) and brine (250 mL), and dried over $MgSO_4$. After filtration, the filtrate was concentrated and the residue was purified on a silica gel column (1 kg silica gel) and eluted with ethyl acetate in hexanes (0 to 25%) to furnish 41 g (50%) of desired product which was used in the next reaction without further purification.

Step 4: To a solution of compound from Step 3 (40 g, 111.6 mmol) in DMF (250 mL) at 0° C. was added 60% NaH (17.85 g, 446.4 mmol) and the mixture was stirred at 20° C. for 30 min. To this mixture at 0° C. was added benzyl bromide (23.86 g, 139.5 mmol) dropwise over a period of 30 min and was heated at 70° C. for 19 h. After cooling to room temperature, the reaction mixture was diluted with water (100 mL) and acidified with acetic acid to pH 7-8. The reaction mixture was extracted with ethyl acetate (2×500 mL) and the combined organic layers were washed with water (1 L), brine (1 L), and dried over $MgSO_4$ (200 g). After filtration, the filtrate was concentrated and the residue was purified by flash chromatography (1 kg silica gel, eluting with ethyl acetate in hexanes 0 to 20%) to furnish 33.78 g (67.4%) of desired product as an oil.

$^1$H NMR (DMSO-d$_6$): δ 7.39-7.23 (m, 15H), 4.72 (s, 1H), 4.64 (dd, J=15.4 and 11.6 Hz, 2H), 4.55-4.44 (m, 4H), 4.06 (dd, J=9.4 and 4.9 Hz, 1H), 3.61-3.51 (m, 3H), 3.30 (s, 3H), 1.32 (s, 3H); IR (neat) 3427, 3063, 3030, 2901, 1952, 1495, 1453, 1369, 1200, 1103, 1028, 736 and 698 cm$^{-1}$; MS (ES$^+$) 471.38 (M+Na). Anal. Calcd for $C_{28}H_{32}O_5$: C, 74.97; H, 7.19. Found: C, 74.87; H, 7.22.

Step 5: To a solution of product from Step 4 (33.5 g, 74.77 mmol) in dioxane (250 mL) was added 2 N HCl (250 mL) and heated at reflux for 20 h. The reaction mixture was allowed to attain room temperature and diluted with ethyl acetate (1 L) and organic layer was collected. The aqueous layer was further extracted with ethyl acetate (1 L). The combined organic layers were washed with water (2×500 mL), saturated aqueous $NaHCO_3$ (150 mL), and brine (500 mL), and dried over $MgSO_4$. After filtration, the filtrate was concentrated and the residue was purified by flash chromatography (1.5 kg silica gel, eluting with ethyl acetate in hexanes) to furnish 14.52 g (45%) of desired product, 3,4-bis(benzyloxy)-5-(benzyloxymethyl)-3-methyl-tetrahydrofuran-2-ol, as an oil which is a mixture of isomers.

$^1$H NMR (DMSO-d$_6$): δ 7.38-7.24 (m, 15H), 6.60 (bs, 1H, $D_2O$ exchangeable), 5.00 (s, 0.7H), 4.99 (s, 0.3H), 4.73-4.47 (m, 6H), 4.19-4.14 (m, 0.3H), 4.06-4.00 (m, 0.7H), 3.79 (d, J=7.5 Hz, 0.7H), 3.67 (d, J=6.2 Hz, 0.3H), 3.61-3.49 (m, 2H), 1.34 (s, 2H), 1.32 (s, 1H);); IR (neat): 3425, 3064, 3031, 2926, 2870, 1954, 1878, 1812, 1735, 1603, 1497, 1454, 1364, 1311, 1252, 1202, 1094, 1028, 910, 855, 814, 737, 698 cm$^{-1}$; MS (ES$^+$) 457.38 (100% M+Na).

Step 6: To a stirred solution of compound from Step 5 (14.06 g, 32.37 mmol) in THF (150 mL) was added diethyl (cyanomethyl)phosphonate (6.30 g, 35.60 mmol) and cooled to −78° C. To this cooled solution, lithium bis(trimethylsilyl) amide (35.60 mL, 35.60 mmol, 1M solution in THF) was added over a period of 15 min. The temperature of the reaction mixture was brought to 20° C. over a period of 4 h and further stirred for another 16 h. The reaction mixture was again cooled to −78° C. and to this were added diethyl (cyanomethyl)-phosphonate (8.6 g, 48.55 mmol) and lithium bis(trimethylsilyl)amide (16.18 mL, 16.18 mmol, 1M solution in THF) and stirred for 24 h at 20° C. The reaction was quenched by adding water (50 mL), stirred for 30 min and extracted with ethyl acetate (2×1000 mL). The combined organic extracts were washed with water (1×500 mL), brine (1×250 mL), and dried (MgSO$_4$). After filtration, the filtrate was concentrated to afford 14.7 g (98.6%) of the product, which was used as such for next step.

Example A-6

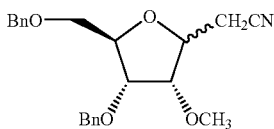

2-(4-(Benzyloxy)-5-(benzyloxymethyl)-3-methoxy-tetrahydrofuran-2-yl)acetonitrile (Scheme A-5)

Step 1: A solution of compound from Example A-5, Step 1 (4 g, 11.61 mmol) in DMF (95 mL) was treated with NaH (60%, 1.86 g, 46.5 mmol) and stirred at room temperature for 1 h followed by addition of MeI (0.87 mL, 13.84 mmol) in DMF (15 mL). The reaction mixture was stirred at room temperature for 23 h and was diluted with EtOAc (600 mL), neutralized with HOAc, washed with water (2×300 mL) and brine (200 mL), and dried over MgSO$_4$. After filtration and concentration of the filtrate, the residue (5.8 g, light yellow oil) was used as such for next step.
MS (ES$^+$) 381.46 (M+Na).

Step 2: A solution of product from Step 1 (5.8 g crude) in a mixture of 3M H$_2$SO$_4$/HOAc (1:4, 60 mL) was heated at 70° C. for 2 h. The reaction mixture was diluted with chloroform (300 mL) and washed with water (2×200 mL), 1M NaHCO$_3$ (200 mL), water again (200 mL), and dried over MgSO$_4$. After filtration and concentration of the filtrate, the residue (4.5 g, yellow oil) was used as such for next step.
MS (ES$^+$) 367.48 (M+Na).

Step 3: A solution of product from Step 2 (3.5 g) in THF (42 mL) was cooled to −78° C. and treated with diethyl (cyanomethyl)phosphonate (4.2 mL, 25.96 mmol) followed by addition of 1M lithium bis(trimethylsilyl)amide in THF (10.5 mL, 10.5 mmol). The reaction mixture was warmed to room temperature and stirred for 18 h and was diluted with ether (400 mL) and water (200 mL). The aqueous phase was extracted further with ether (200 mL). The combined organic extracts were washed with water (2×200 mL) and dried over MgSO$_4$. After filtration and concentration of the filtrate, the residue was purified on a silica gel column using hexanes:ethyl acetate (1:0 to 2:1) as eluent to give 2.4 g (a mixture of anomeric isomers, 72% for three steps) of 2-(4-(benzyloxy)-5-(benzyloxymethyl)-3-methoxy-tetrahydrofuran-2-yl)acetonitrile as a colorless oil.
MS (ES$^+$): 390.43 (M+Na)$^+$.

Example A-7

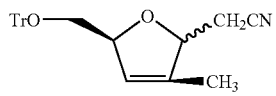

2-(3-Methyl-5-(trityloxymethyl)-2,5-dihydrofuran-2-yl)acetonitrile (Scheme A-6)

Step 1: To a solution of 3-methyl-5-trityloxymethyl-5H-furan-2-one (1.85 g, 5 mmol, prepared by the method of Lopez-Herrera et. al., J. Carbohydrate Chem. 1994, 13, 767) in toluene (25 mL) under N$_2$ atmosphere at −78° C. was added dropwise with stirring DiBAL (10 mL, 10 mmol, 1M solution in toluene). The addition rate was maintained to keep the temperature of the reaction below −70° C. The reaction was stirred at −78° C. for 2 h and quenched with ethyl acetate (4 mL) at that temperature. The reaction mixture was allowed to warm to room temperature and concentrated under vacuum to dryness. The residue obtained was purified by flash chromatography on silica gel eluting with 20% ethyl acetate in hexanes to furnish 1.65 g (88%) of 3-methyl-5-trityloxymethyl-2,5-dihydrofuran-2-ol (a mixture of isomers) as a white solid; mp 100-102° C.

$^1$H NMR (DMSO-d$_6$): δ 7.43-7.23 (m, 15H), 6.31 (dd, J=2.8 and 7.3 Hz, 1H), 5.74-5.65 (m, 2H), 4.85 (bs, 0.4H), 4.65 (bs, 0.6H), 3.06 (dd, J=6.8 and 9.1 Hz, 0.6H), 2.95-2.83 (m, 1.4H), 1.69, 1.66 (2s, 3H); IR (KBr) 3414, 3058, 3028, 2918, 2869, 1962, 1737, 1597, 1489, 1445, 1222, 1069, 1033, 985, 747, 702 cm$^{-1}$; Anal. Calcd for C$_{25}$H$_{24}$O$_3$: C, 80.61; H, 6.50. Found: C, 80.15; H, 6.39.

Step 2: To a slurry of NaH (0.19 g, 4.8 mmol, 60%) in DME (24 mL) cooled to 0° C. was added dropwise diethyl (cyanomethyl)phosphonate (0.96 mL, 6 mmol). The solution became homogenous on completion of addition and was stirred at 0° C. for 30 min. To this solution was added dropwise a solution of product from Step 6, 3-methyl-5-trityloxymethyl-2,5-dihydro-furan-2-ol (1.85 g, 5 mmol) in DME (15 mL). The reaction mixture was allowed to warm to room temperature, stirred overnight, diluted with water (50 mL) and was extracted with ether (2×50 mL). The combined organic layers were washed with water (50 mL), brine (50 mL), and dried over MgSO$_4$. After filtration, the filtrate was concentrated and the residue was purified by flash chromatography (25 g silica gel) eluting with ethyl acetate in hexanes to furnish 1.06 g (90%) of 2-(3-methyl-5-trityloxymethyl-2,5-dihydro-furan-2-yl)-acetonitrile (a mixture of isomers), as a colorless oil.

$^1$H NMR (CDCl$_3$): δ 7.47-7.41 (m, 6H), 7.33-7.19 (m., 9H), 5.64 (s, 0.6H), 5.53 (s, 0.4H), 5.10 (m, 0.4H), 4.96-4.83 (m, 1.6H), 3.26 (dd, J=5.6 and 9.7 Hz, 0.4H), 3.18-3.05 (m, 1.6H), 2.83-2.53 (m, 2H), 1.79 (m, 3H); IR (KBr) 3430, 3059, 2917, 2865, 2363, 2249, 1967, 1735, 1491, 1445, 1242, 1074, 993, 748, 704 cm$^{-1}$; Anal. Calcd for C$_{27}$H$_{25}$NO$_2$: C, 81.07; H, 6.43; N, 3.50. Found: C, 81.37; H, 6.25; N, 3.49.

Example A-8

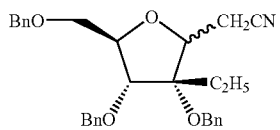

2-(3,4-Bis(benzyloxy)-5-(benzyloxymethyl)-3-ethyl-tetrahydrofuran-2-yl)acetonitrile (Scheme A-4)

Step 1: A solution of oxalylchloride (4 mL, 0.04 mol) was added dropwise to a solution of DMSO (6.18 mL, 0.087 mol) in anhydrous $CH_2Cl_2$ (100 mL) at −78° C. with stirring over a period of 30 min. To this was added dropwise a solution of product from Step 1 of Example A-5 (10 g, 0.029 mol) in $CH_2Cl_2$ (25 mL) over a period of 30 min. The reaction mixture was stirred at −70° C. for 3.5 h and quenched by dropwise addition of triethylamine (5 mL) at −70° C. over 30 min. The reaction mixture was allowed to warm to room temperature and diluted with water (200 mL). The organic layer was separated and aqueous layer was extracted with chloroform (2×200 mL). The combined organic layers were washed with water (200 mL), brine (200 mL), and dried over $MgSO_4$. After filtration, the filtrate was concentrated and the residue was dissolved in tert-butyl dimethyl ether (150 mL), and cooled to −78° C. To this cooled solution was added dropwise a solution of ethyl magnesium bromide (43.5 mL, 1M in THF, 0.043 mol). The reaction was further stirred at −78° C. for 2.5 h and poured into ice cold water (200 mL) and neutralized with 1N HCl (300 mL) to pH 6-7. The organic layer was collected and the aqueous layer was extracted with ethyl acetate (200 mL). The combined organic layers were washed with water (2×200 mL), saturated $NaHCO_3$ (2×200 mL), water (100 mL) and brine (200 mL), and dried over $MgSO_4$. After filtration, the filtrate was concentrated and the residue was purified on silica gel column using gradient 0 to 25% EtOAc in hexanes to give 3.0 g (30%) of desired product.

Step 2: To a solution of the product from Step 1 (3 g, 8 mmol) in THF (100 mL) at 0° C. was added NaH (0.5 g, 12 mmol) and the mixture was stirred at 20° C. for 30 min. After cooling to 0° C., benzyl bromide (1.5 mL, 12 mmol) was added dropwise and heated to 70° C. for 16 h. After cooling, the reaction mixture was diluted with water (100 mL), acidified with acetic acid to pH 7-8 and was extracted with ethyl acetate (2×200 mL). The combined organic layers were washed with water (200 mL), brine (200 mL), and dried over $MgSO_4$. After filtration, the filtrate was concentrated and the residue was purified by flash chromatography (gradient 0 to 20% EtOAc in hexanes) to give 1.3 g (86%) of 3,4-bis-benzyloxy-5-benzyloxymethyl-3-ethyl-2-methoxy-tetrahydro-furan.
MS (ES$^+$) 463.25 (M+1).

Step 3: To a solution of the product from Step 2 (3.2 g, 6.9 mmol) in dioxane (50 mL) was added 2 N HCl (50 mL) and heated at reflux for 20 h. The reaction mixture was allowed to attain room temperature and diluted with ethyl acetate (100 mL). The organic layer was collected and the aqueous layer was further extracted with ethyl acetate (100 mL). The combined organic layers were washed with water (2×100 mL), saturated aqueous $NaHCO_3$ (50 mL), water (50 mL) and brine (50 mL), and dried over $MgSO_4$. After filtration, the filtrate was concentrated and the residue was purified by flash chromatography (gradient 0 to 20% EtOAc in hexanes) to furnish 1.2 g (30%) of 3,4-bis-benzyloxy-5-benzyloxymethyl-3-ethyl-tetrahydro-furan-2-ol, as an oil.

Step 4: To a stirred solution of sodium hydride (0.18 g, 5.4 mmol) and diethyl (cyanomethyl)-phosphonate (0.85 mL, 5.4 mmol) in DME (20 mL) was added product from Step 3 (2.7 mmol, 1.2 g) and the reaction was stirred at room temperature for 16 h. The reaction was then diluted with diethyl ether (100 mL), washed with water (100 mL) and brine (100 mL). The organic layer was collected, dried over $MgSO_4$, filtered and the filtrate was concentrated to give 1.5 g of crude 3,4-bis-benzyloxy-5-benzyloxymethyl-3-ethyl-tetrahydro-furan-2-yl)-acetonitrile, as an oil, which was used as such for the next step.

Example A-9

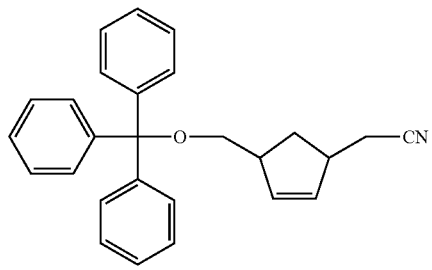

2-(4-(Trityloxymethyl)cyclopent-2-enyl)acetonitrile (Scheme A-7)

Step 1: To a stirred solution of (4-hydroxymethyl-cyclopent-2-enyl)-methanol (13.8 g, 107.81 mmol, prepared by method of Mekrami et al., Tetrahedron: Asymmetry 1992, 3, 431) in methylene chloride (100 mL) was added pyridine (25.5 g, 118.59 mmol) and trityl chloride (33.06 g, 118.59 mmol) at room temperature and the mixture was stirred for 18 h. After addition of water (50 mL), the reaction mixture was diluted with methylene chloride (100 mL) and the organic layer was separated. The aqueous layer was further extracted with methylene chloride (100 mL). The combined organic layers were washed with water (100 mL), brine (50 mL), and dried ($MgSO_4$). After filtration, the filtrate was concentrated and the residue was purified on a silica gel column using ethyl acetate in hexanes (0 to 30%), which afforded 18.25 g (45.7%) of desired product, (4-trityloxymethyl-cyclopent-2-enyl)-methanol.
$^1$HNMR (DMSO-d$_6$): δ 7.39-7.22 (m, 15H), 5.77-5.72 (m, 2H), 4.53 (t, J=5.4 Hz, 1H, D$_2$O exchangeable), 3.22-3.18 (m, 2H), 2.93-2.84 (m, 3H), 2.74-2.69 (m, 1H), 2.10 (m, 1H), 1.12-1.03 (m, 1H); MS (ES$^+$) 393.47 (M+23).

Step 2: To a stirred solution of product from Step 1 (18 g, 48.45 mmol) in pyridine (50 mL) was added p-toluenesulfonyl chloride at room temperature and the mixture was stirred for 48 h. After concentration, the residue was dissolved in ethylacetate (200 mL), washed with water (2×100 mL), brine (50 mL), and dried (MgSO$_4$). After filtration, the filtrate was concentrated and the residue was purified on silica gel column using ethyl acetate in hexanes (0 to 30%), which afforded 21.45 g (84.4%) of desired product, toluene-4-sulfonic acid 4-trityloxymethyl-cyclopent-2-enylmethyl ester.

$^1$HNMR (DMSO-d$_6$): δ 7.69 (d, J=8.3 Hz, 2H), 7.40 (d, J=8.3 Hz, 2H), 7.38-7.22 (m, 15H), 5.79 (d, J=5.4 Hz, 1H), 5.57 (d, J=5.6 Hz, 1H), 3.91-3.77 (m, 2H), 2.94-2.83 (m, 4H), 2.37 (s, 3H), 2.09-1.98 (m, 1H), 1.08-0.99 (m, 1H).

Step 3: To a stirred solution of compound from Step 2, toluene-4-sulfonic acid 4-trityloxymethyl-cyclopent-2-enylmethyl ester (21.3 g, 40.59 mmol) in dimethylformamide (150 mL) was added sodium cyanide (3.58 g, 73.18 mmol) at room temperature and the reaction was stirred at 70° C. for 48 h. After cooling, the reaction mixture was extracted with ethyl acetate (2×250 mL), washed with water (2×100 mL), brine (50 mL) and dried (MgSO$_4$). After filtration, the filtrate was concentrated and the residue was purified on a silica gel column using ethyl acetate in hexanes (0 to 30%), which afforded 14.96 g (97.1%) of desired product, (4-trityloxymethyl-cyclopent-2-enyl)-acetonitrile, as a colorless solid.

$^1$HNMR (DMSO-d$_6$): δ 7.40-7.23 (m, 15H), 5.84 (d, J=5.1 Hz, 1H), 5.69 (d, J=5.4 Hz, 1H), 3.00-2.90 (m, 4H), 2.53 (d, J=6.4 Hz, 2H), 2.30-2.20 (m, 1H), 1.16-1.07 (m, 1H).

Example A-10

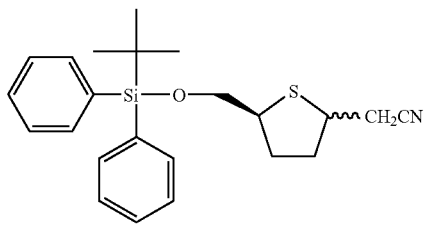

2-(5-((tert-Butyldiphenylsilyloxy)methyl)-tetrahydrothiophen-2-yl)acetonitrile (Scheme A-8)

It was prepared from 5-O-(tert-butyldiphenylsilyl)-2,3-dideoxy-4-thioribofuranose (Secrist III et al., J. Med. Chem. 1992, 35, 533) by following the same method used in Example A-3, Step 3.

$^1$H NMR (CDCl$_3$) δ in ppm 7.70-7.40 (m, 10H), 4.10 (m, 1H), 3.65 (m, 3H), 3.60 (m, 2H), 2.10 (m, 2H), 1.80 (m, 2H), 1.10 (s, 9H).

Example A-11

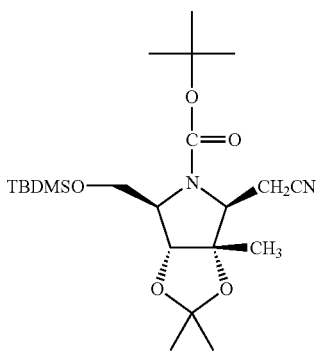

tert-Butyl 6-((tert-butyldimethylsilyloxy)methyl)-4-(cyanomethyl)-2,2,3a-trimethyl-tetrahydro-[1,3]dioxolo[4,5-c]pyrrole-5-carboxylate This was prepared by following the method reported in application Ser. No. 11/157,867 filed on Jun. 22, 2005.

Example B-1

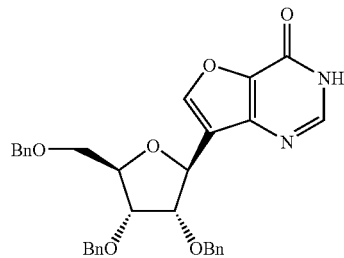

7-β-(2',3',5'-Tri-O-benzyl-D-ribofuranosyl)-furo[3,2-d]pyrimidin-4(3H)-one (Scheme B-1)

Step 1: To a stirred solution of compound from Step 4 of example A-2, (3S,4R,5R)-(3,4-bis-benzyloxy-5-benzyloxymethyl-tetrahydro-furan-2-yl)-acetonitrile (10.7 g, 24.12 mmol) in DMF (150 mL) was added tert-butoxybis(dimethylamino)methane (21.02 g, 120.62 mmol) at room temperature and stirred for 12 h. The reaction mixture was diluted with toluene (700 mL) and washed with water (2×250 mL), brine (1×50 mL) and dried (MgSO$_4$). After filtration, the filtrate was concentrated to give (13.8 g) of desired product, which was used as such for next step.

Step 2: The compound from Step 1 (13.8 g, 24.12 mmol) was dissolved in chloroform (250 mL), trifluoroacetic acid (4.59 g, 40.29 mmol) and water (137 mL) at room temperature and stirred for 18 h. The organic layer was separated and the aqueous layer was extracted with chloroform (2×200 mL). The combined organic extracts were washed with water (2×200 mL), brine (1×100 mL), and dried (MgSO$_4$). After filtration, the filtrate was concentrated to afford 12.59 g of desired product. A small amount was taken out and purified on silica gel column using ethyl acetate and hexanes.

MS (ES$^+$) 494.20 (M+23), (ES$^-$) 470.28 (M−1); Anal. Calcd for C$_{29}$H$_{29}$NO$_5$.0.75H$_2$O: C, 71.80; H, 6.33; N, 2.88. Found: C, 71.95; H, 6.04; N, 2.88.

Step 3: To a stirred solution of product from Step 2, (186.5 g, 395.4 mmol) in DMF (1500 mL) was added sodium hydride (19.7 g, 60%, 494.3 mmol) in four portions at 0° C. over a period of 1.5 h followed by 2-bromodiethylmalonate (118.1 g, 494.3 mmol) over a period of 30 min at 0° C. and stirred at room temperature for 12 h. After diluting with water (1000 mL), the reaction mixture was extracted with ethyl acetate (3×2000 mL). The combined organic extracts were washed with water (2×1000 mL), brine (1×200 mL), and dried (MgSO$_4$). After filtration, the filtrate was concentrated to give 296 g of crude desired product, which was used in the next reaction without further purification.

Step 4: To a compound from Step 3 (296 g, crude) in EtOH (1000 mL) was added 1,5-diazabicyclo[4.3.0]non-5-ene (58.9 g, 474.48 mmol) at room temperature and stirred for 18 h. The reaction mixture was concentrated and the residue was dissolved in ethyl acetate (4000 mL), washed with water (2×1000 mL), brine (2×500 mL), and dried (MgSO$_4$). After filtration, the filtrate was concentrated and the crude residue was purified by flash chromatography on silica gel using ethyl acetate and hexanes to afford 29 g, (13.1%) of the desired product as light brown oil.

Step 5: To a stirred solution of compound from Step 4 (29.0 g, 52.04 mmol) in EtOH (600 mL) was added formamidine acetate (135 g, 1301 mmol) at room temperature and heated at reflux for four days and the solid material was removed by filtration and filtrate was concentrated. The residue was dissolved in chloroform (400 mL), washed with water (2×100 mL), brine (1×100 mL), and dried (MgSO$_4$). The crude residue was purified by flash chromatography on silica gel using CMA-80 in chloroform (0 to 20%) to afford 12 g (42.8%) of the desired product (12 g, 42.8%) as a colorless crystalline solid; mp 88-100° C.

$^1$H NMR (DMSO-d$_6$): δ 12.66 (bs, 1H, D$_2$O exchangeable), 8.11 (s, 1H), 8.05 (d, J=2.8 Hz, 1H), 7.33-7.25 (m, 15H), 5.11 (d, J=4.8 Hz, 1H), 4.61 (s, 2H), 4.58-4.48 (m, 4H), 4.4 (t, J=4.7 Hz, 1H), 4.19-4.12 (m, 2H), 3.63 (ddd, J=23.3, 10.7. 3.2 Hz, 2H); MS (ES$^+$) 539.43 (M+1), 561.42 (M+23), (ES$^-$) 537.44 (M−1); Anal. Calcd for C$_{32}$H$_{30}$N$_2$O$_6$: C, 71.36; H, 5.61; N, 5.20. Found: C, 71.30; H, 5.54; N, 5.10.

Example B-2

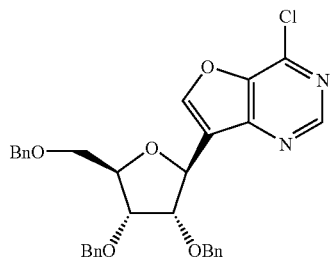

4-Chloro-7-β-(2',3',5'-tri-O-benzyl-D-ribofuranosyl)-furo[3,2-d]pyrimidine (Scheme B-2)

To a stirred solution of compound from Example B-1, Step 5, (6.26 g, 11.62 mmol), benzyltriethylammonium chloride (5.29 g, 23.24 mmol), N,N-dimethylaniline (2.12 g, 17.43 mmol) in acetonitrile (50 mL) was added phosphorous oxychloride (10.69 g, 69.74 mmol) at 80° C. and further stirred at 80° C. for 30 min. Then the reaction was concentrated to dryness, dissolved in chloroform (100 mL) and quenched with water (50 mL). The organic layer was separated and aqueous layer was further extracted with chloroform (2×50 mL). The combined chloroform extracts were washed with water (2×100 mL), sat. NaHCO$_3$ (1×50 mL), water (1×100 mL), and brine (1×50 mL), and dried (MgSO$_4$). After filtration, the filtrate was concentrated and the residue was purified by flash chromatography on silica gel column using ethyl acetate in hexanes (0 to 25%) to afford 5.62 g (86.8%) of desired product as a colorless crystalline solid.

$^1$H NMR (DMSO-d$_6$): δ 8.87 (s, 1H), 8.54 (s, 1H), 7.33-7.19 (m, 15H), 5.21 (d, J=5.1 Hz, 1H), 4.66-4.47 (m, 7H), 4.24-4.18 (m, 2H), 3.66 (ddd, J=23.1, 10.5. 3.5 Hz, 2H); Anal. Calcd for C$_{32}$H$_{29}$ClN$_2$O$_5$: C, 68.99; H, 5.24; Cl, 6.36; N, 5.02. Found: C, 69.12; H, 5.19; Cl, 6.30; N, 5.04.

Example B-3

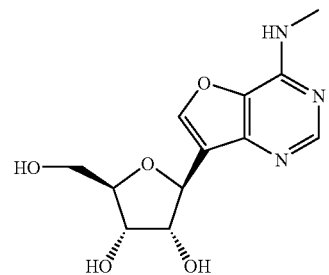

4-Methylamino-7-β-(D-ribofuranosyl)-furo[3,2-d]pyrimidine (Scheme B-3)

Step 1: To a stirred solution of product from Example B-2 (0.5 g, 0.897 mmol), methylamine hydrochloride (0.36 g, 5.38 mmol) in EtOH (10 mL) was added triethylamine (1.815 g, 17.94 mmol) at room temperature and stirred at 45° C. for 5 h and at room temperature for 12 h. The reaction mixture was concentrated to dryness, dissolved in chloroform (100 mL), washed with water (2×25 mL), brine (1×20 mL), and dried (MgSO$_4$). After filtration, the filtrate was concentrated and the residue was purified on silica gel column using ethyl acetate in hexanes (0 to 50%) which afforded 0.266 g (53.7%) of desired product as a colorless solid.

MS (ES$^+$) 574.42 (M+23), (ES$^-$) 550.72 (M−1).

Step 2: To a stirred solution of product from Step 1 (0.258 g, 0.468 mmol) in methylene chloride (20 mL) was added boron trichloride (4.68 mL, 4.68 mmol, 1M solution in methylene chloride) at −78° C. and stirred at the same temperature for 1 h. Then the reaction was brought to −30° C. over a period of 30 min, and quenched by adding a mixture of methanol:chloroform (2:1, 5 mL). After the reaction mixture reached to room temperature, it was neutralized with aqueous NH$_3$ in MeOH (10%, 5 mL) and was concentrated to dryness. The solid obtained was suspended in MeOH (15 mL) and 4N HCl in dioxane (2 mL) was added and reaction mixture was concentrated. The residue was purified by flash chromatography on silica gel using CMA-80 in chloroform (0 to 100%) which afforded 118 mg (89.6%) of the desired product as a colorless crystalline solid; mp 88-100° C.

$^1$H NMR (DMSO-d$_6$): δ 8.30 (s, 1H), 8.21(s, 1H), 7.93 (d, J=4.7 Hz, 1H, D$_2$O exchangeable), 5.80 (dd, J=9.4, 3.3 Hz, 1H, D$_2$O exchangeable), 5.05 (d, J=6.4 Hz, 1H, D$_2$O exchangeable), 4.88 (d, J=4.3 Hz, 1H), 4.77 (d, J=7.3, Hz, 1H, D$_2$O exchangeable), 4.35-4.29 (m, 1H), 1.04-4.00 (m, 1H), 3.89 (dd, J=5.4, 2.6 Hz, 1H), 3.63 (td, J=12.0, 3.0 Hz, 1H), 3.52-3.44 (m, 1H), 2.97 (d, J=4.5 Hz, 3H); IR (KBr) 3324.6, 2931.8, 1649.4, 1557.1, 1520.0, 1442.4, 1403.8, 1332.5, 1221.1, 1180.1, 1101.5, 1080.1, 1021.9, 956.9, 892.8, 821.7, 787.4, 742.6, 586.4 and 524.6 cm$^{-1}$; MS (ES$^+$) 282.51 (M+1); Anal. Calcd for C$_{12}$H$_{15}$N$_3$O$_5$.0.6H$_2$O: C, 49.34; H, 5.59; N, 14.38. Found: C, 49.41; H, 5.46; N, 14.06.

Example B-4

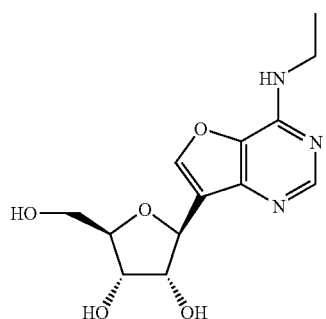

4-Ethylamino-7-β-(D-ribofuranosyl)-furo[3,2-d]pyrimidine (Scheme B-3)

This was prepared according to the procedure used for Example B-3, and using ethylamine instead of methylamine, mp 76-88° C., yield 32% in two steps.

$^1$H NMR (DMSO-$d_6$): δ 8.27 (s, 1H), 8.21 (s, 1H), 8.00 (t, J=5.8 Hz, 1H, $D_2O$ exchangeable), 5.81 (d, J=10.1 Hz, 1H, $D_2O$ exchangeable), 5.04 (d, J=7.62 Hz, 1H, $D_2O$ exchangeable), 4.68 (d, J=6.2 Hz, 1H, $D_2O$ exchangeable), 4.76 (d, J=7.3 Hz, 1H), 4.35-4.29 (m, 1H), 4.04-4.00 (m, 1H), 3.89 (dd, J=5.4, 2.8 Hz, 1H), 3.63 (d, J=13.1 Hz, 1H), 3.54-3.46 (m, 3H), 1.18 (t, J=7.15 Hz, 3H); IR (KBr) 3427.5, 3249.4, 3110.9, 2926.5, 2874.6, 2779.2, 2618.3, 2525.0, 1640.4, 1558.5, 1502.9, 1419.6, 1330.9, 1249.9, 1224.2, 1171.3, 1118.7, 1082.5, 1014.6, 900.8, 853.2, 749.5, 653.9, 653.6, 588.3 and 547.8 cm$^{-1}$; MS (ES$^+$) 296.52 (M+1); Anal. Calcd for $C_{13}H_{17}N_3O_5 \cdot H_2O \cdot 0.25CH_3OH$: C, 49.52; H, 6.27; N, 13.07. Found: C, 49.83; H, 5.99; N, 12.80.

Example B-5

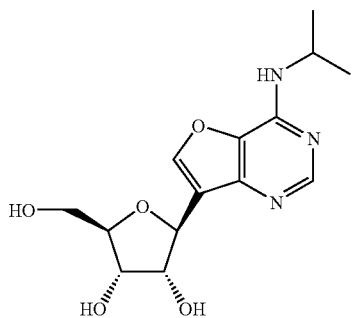

4-Isopropylamino-7-β-(D-ribofuranosyl)-furo[3,2-d]pyrimidine (Scheme B-3)

This was prepared according to the procedure used for Example B-3, and using isopropylamine instead of methylamine, mp 58-80° C., yield 32% in two steps.

$^1$H NMR (DMSO-$d_6$): δ 8.27 (s, 1H), 8.21 (s, 1H), 7.84 (d, J=8.1 Hz, 1H, $D_2O$ exchangeable), 5.83 (bs, 1H, $D_2O$ exchangeable), 5.03 (d, J=6.4 Hz, 1H, $D_2O$ exchangeable), 4.88 (d, J=4.3 Hz, 1H, $D_2O$ exchangeable), 4.76 (d, J=7.3 Hz, 1H), 4.45-4.29 (m, 2H), 4.04-4.00 (m, 1H), 3.89 (dd, J=5.2, 2.6 Hz, 1H), 3.63 (dd, J=12.0, 2.6 Hz, 1H), 3.53-3.44 (m, 1H), 1.21 (d, J=6.5 Hz, 6H); IR (KBr) 3300.2, 2973.9, 2928.4, 1637.7, 1557.4, 1502.5, 1450.5, 1423.5, 1332.4, 1217.8, 1176.6, 1120.7, 1086.5, 1020.8, 892.4, 821.7, 700.4, 588.3 and 537.6 cm$^{-1}$; MS (ES$^-$) 308 (M−1); Anal. Calcd for $C_{14}H_{19}N_3O_5 \cdot 0.8H_2O$: C, 51.94; H, 6.41; N, 12.98. Found: C, 52.24; H, 6.41; N, 12.50.

Example B-6

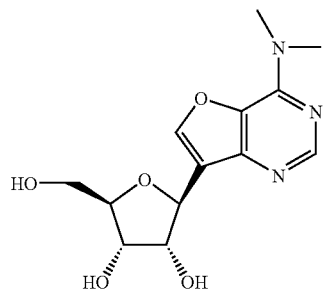

4-Dimethylamino-7-β-(D-ribofuranosyl)-furo[3,2-d]pyrimidine (Scheme B-3)

This was prepared according to the procedure used for Example B-3, and using dimethylamine instead of methylamine, mp 210° C., yield 45% in two steps.

$^1$H NMR (DMSO-$d_6$): δ 8.29 (s, 1H), 8.24 (s, 1H), 5.76 (dd, J=9.4, 3.4 Hz, 1H, $D_2O$ exchangeable), 5.05 (d, J=6.2 Hz, 1H, $D_2O$ exchangeable), 4.88 (d, J=4.5 Hz, 1H, $D_2O$ exchangeable), 4.78 (d, J=7.3 Hz; 1H), 4.35-4.29 (m, 1H), 4.04-4.00 (m, 1H), 3.89 (dd, J=5.8, 3.0 Hz, 1H), 3.63 (dd, J=12.4, 3.4 Hz, 1H), 3.52-3.44 (m, 1H), 3.33 (s, 6H); IR (KBr) 3361.4, 3120.5, 2972.9, 2930.6, 2865.1, 1627.5, 1515.9, 1428.7, 1406.1, 1368.8, 1348.9, 1304.8, 1275.0, 1224.0, 1115.1, 1098.3, 1081.7, 1018.5, 869.3, 848.3, 748.2 and 593.3 cm$^{-1}$; MS (ES$^+$) 296.51 (M+1); Anal. Calcd for $C_{13}H_{17}N_3O_5$: C, 52.87; H, 5.80; N, 14.23. Found: C, 52.80; H, 5.87; N, 14.07.

Example B-7

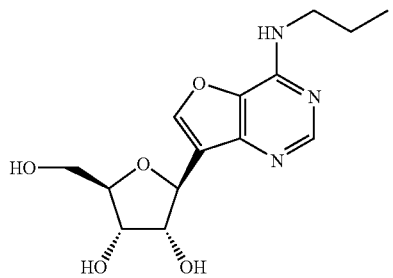

4-n-Propylamino-7-β-(D-ribofuranosyl)-furo[3,2-d]pyrimidine (Scheme B-3)

This was prepared according to the procedure used for Example B-3, and using propylamine instead of methylamine, mp 58-80° C., yield 21% in two steps.

¹H NMR (DMSO-d$_6$): δ 8.27 (s, 1H), 8.21 (s, 1H), 8.03 (bs, 1H, D$_2$O exchangeable), 5.81 (dd, J=9.8, 3.4 Hz, 1H, D$_2$O exchangeable), 5.04 (d, J=6.4 Hz, 1H, D$_2$O exchangeable), 4.88 (d, J=4.3 Hz, 1H, D$_2$O exchangeable), 4.76 (d, J=7.3 Hz, 1H), 4.36-4.29 (m, 1H), 4.04-4.00 (m, 1H), 3.89 (dd, J=5.4, 2.6 Hz, 1H), 3.65-3.60 (m, 1H), 3.52-3.40 (m, 3H), 1.65-1.54 (m, 2H), 0.90 (t, J=7.3 Hz, 3H); IR (KBr) 3310.5, 2931.8, 2207.9, 1911.5, 1640.7, 1557.6, 1510.3, 1422.2, 1333.6, 1304.4, 1238.3, 1170.5, 1116.8, 1082.1, 1020.2, 891.1, 821.7, 746.4 and 586.4 cm$^{-1}$; MS (ES$^+$) 310 (M+1), (ES$^-$) 308.48 (M−1); Anal. Calcd for C$_{14}$H$_{19}$N$_3$O$_5$.0.75H$_2$O: C, 52.08; H, 6.40; N, 13.01. Found: C, 52.10; H, 6.08; N, 12.62.

Example B-8

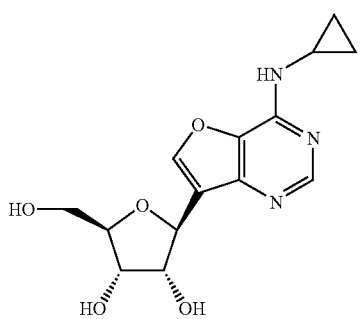

4-Cyclopropylamino-7-β-(D-ribofuranosyl)-furo[3,2-d]pyrimidine (Scheme B-3)

This was prepared according to the procedure used for Example B-3, and using cyclopropylamine instead of methylamine, mp 88-100° C., yield 44% in two steps.

¹H NMR (DMSO-d$_6$): δ 8.31 (s, 1H), 8.23 (s, 1H), 8.14 (d, J=3.5 Hz, 1H, D$_2$O exchangeable), 5.77 (dd, J=9.4, 3.4 Hz, 1H, D$_2$O exchangeable), 5.05 (d, J=6.4 Hz, 1H, D$_2$O exchangeable), 4.88 (d, J=4.3 Hz, 1H, D$_2$O exchangeable), 4.77 (d, J=7.3 Hz, 1H), 4.36-4.29 (m, 1H), 4.04-4.00 (m, 1H), 3.89 (dd, J=5.8, 3.2 Hz, 1H), 3.63-3.44 (m, 2H), 3.01-2.92 (m, 1H), 0.79-0.73 (m, 2H), 0.62-0.57 (m, 2H); IR (KBr) 3295.5, 2924.1, 2189.0, 1640.2, 1557.4, 1502.5, 1425.4, 1354.4, 1300.6, 1227.4, 1120.1, 1086.2, 1022.1, 892.7, 824.1, 787.0, 744.3, 702.1, 589.2 and 534.3 cm$^{-1}$; MS (ES$^+$) 308.52 (M+1), (ES$^-$) 306.46 (M−1); Anal. Calcd for C$_{14}$H$_{17}$N$_3$O$_5$.H$_2$O: C, 51.68; H, 5.88; N, 12.91. Found: C, 51.89; H, 5.80; N, 12.59.

Example B-9

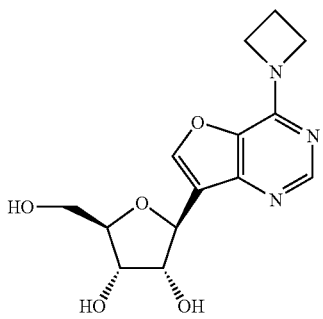

4-Azetidino-7-β-(D-ribofuranosyl)-furo[3,2-d]pyrimidine (Scheme B-3)

This was prepared according to the procedure used for Example B-3, and using azetidine instead of methylamine, mp 192° C., yield 56% in two steps.

¹H NMR (DMSO-d$_6$): δ 8.28 (s, 1H), 8.23 (s, 1H), 5.72 (dd, J=9.2, 3.2 Hz, 1H, D$_2$O exchangeable), 5.04 (d, J=6.4 Hz, 1H, D$_2$O exchangeable), 4.88 (d, J=4.5 Hz, 1H, D$_2$O exchangeable), 4.77 (d, J=7.3 Hz, 1H), 4.35-4.28 (m, 5H), 4.03-3.99 (m, 1H), 3.88 (dd, J=5.8, 3.0 Hz, 1H), 3.65-3.44 (m, 2H), 2.49-2.40 (m, 2H); IR (KBr) 3413.0, 3211.5, 3062.0, 2943.4, 2879.7, 2650.0, 1896.7, 1633.2, 1592.4, 1547.5, 1508.3, 1440.8, 1401.7, 1340.3, 1296.8, 1244.1, 1213.4, 1171.9, 1118.7, 1082.1, 1013.0, 974.1, 904.6, 866.0, 818.3, 787.4, 748.4, 687.9, 663.5 and 590.1 cm$^{-1}$; MS (ES$^+$) 308.52 (M+1); Anal. Calcd for C$_{14}$H$_{17}$N$_3$O$_5$.0.15H$_2$O: C, 54.24; H, 5.62; N, 13.55. Found: C, 54.27; H, 5.56; N, 13.41.

Example B-10

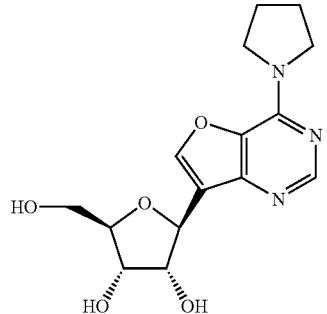

4-Pyrrolidino-7-β-(D-ribofuranosyl)-furo[3,2-d]pyrimidine (Scheme B-3)

This was prepared according to the procedure used for Example B-3, and using pyrrolidine instead of methylamine, mp 198° C., yield 54% in two steps.

¹H NMR (DMSO-d$_6$): δ 8.33 (s, 1H), 8.29 (s, 1H), 5.91 (bs, 1H, D$_2$O exchangeable), 5.11 (d, J=6.2 Hz, 1H, D$_2$O exchangeable), 4.95 (d, J=4.3 Hz, 1H, D$_2$O exchangeable), 4.84 (d, J=7.3 Hz, 1H), 4.41-4.35 (m, 1H), 4.10-4.01 (m, 1H), 3.96 (dd, J=5.8, 3.0 Hz, 1H), 3.94-3.67 (m, 5H), 3.58-3.51 (m, 1H), 2.07-1.97 (bs, 4H); IR (KBr) 3456.4, 3261.6, 3113.1, 2949.2, 2914.8, 2871.0, 2794.8, 2629.6, 1624.6, 1544.8, 1501.3, 1456.3, 1345.9, 1325.1, 1252.8, 1229.2, 1188.3, 1117.7, 1087.7, 1014.5, 980.4, 901.1, 846.7, 787.1, 748.4, 633.4, 588.3 and 545.9 cm$^{-1}$; MS (ES$^+$) 322.54 (M+1); Anal. Calcd for C$_{15}$H$_{19}$N$_3$O$_5$.0.25H$_2$O: C, 55.29; H, 6.03; N, 12.89. Found: C, 55.53; H, 6.01; N, 12.72.

Example B-11

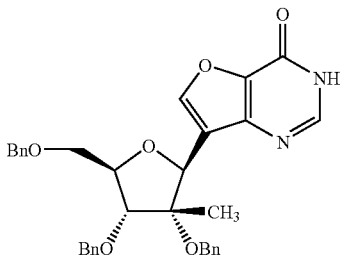

7-β-(2',3',5'-Tri-O-benzyl-2'-C-methyl-D-ribofurano-
syl)-furo[3,2-d]pyrimidin-4(3H)-one (Scheme B-1)

This was prepared according to the procedure used for Example B-1, starting from Example A-5 instead of A-2.

$^1$H NMR (DMSO-d$_6$): δ 12.67 (bs, 1H, D$_2$O exchangeable), 8.14 (s, 1H), 8.09 (s, 1H), 7.38-7.25 (m, 15H), 5.21 (s, 1H), 4.75-4.52 (m, 6H), 4.2-4.15 (m, 1H), 4.05 (d, J=7.72 Hz, 1H), 3.78-3.68 (m, 2H), 1.21 (s, 3H); MS (ES$^+$) 553.37 (M+1); Anal. Calcd for C$_{33}$H$_{32}$N$_2$O$_6$: C, 71.72; H, 5.84; N, 5.07. Found: C, 71.51; H, 5.89; N, 5.07.

Example B-12

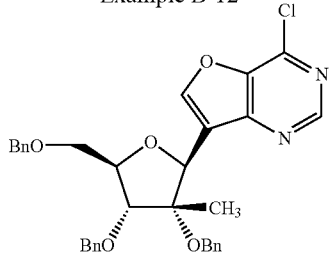

4-Chloro-7-β-(2',3',5'-tri-O-benzyl-2'-C-methyl-D-
ribofuranosyl)-furo[3,2-d]pyrimidine (Scheme B-2)

This was prepared according to the procedure used for Example B-2, using starting material from Example B-11 instead of B-1, yield 92%.

$^1$H NMR (DMSO-d$_6$): δ 8.98 (s, 1H), 8.57 (s, 1H), 7.38-7.24 (m, 15H), 5.31 (s, 1H), 4.70 (dd, J=16.7, 11.6 Hz, 2H), 4.67-4.53 (m, 4H), 4.24-4.19 (m, 1H), 4.10 (d, J=7.5 Hz, 1H), 3.75 (ddd, J=21.8, 10.9, 3.2 Hz, 2H), 1.21 (s, 3H); Anal. Calcd for C$_{33}$H$_{31}$ClN$_2$O$_5$: C, 69.40; H, 5.47; N, 4.90. Found: C, 69.65; H, 5.48; N, 4.92.

Example B-13

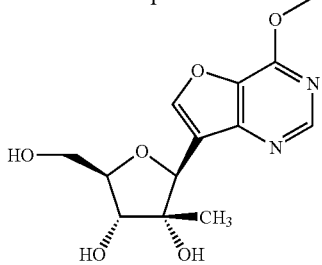

4-Methoxy-7-β-(2'-C-methyl-D-ribofuranosyl)-furo
[3,2-d]pyrimidine (Scheme B-3)

Step 1: To a stirred solution of freshly prepared sodium methoxide {prepared from Na (0.022 g, 3.27 mmol) in MeOH (5 mL)} was added compound from Example B-12 (0.187 g, 0.327 mmol) in methanol (5 mL) at room temperature and further stirred for 2 h. After concentrating the reaction mixture, the residue was suspended in water (15 mL) and extracted with ethylacetate (2×50 mL). The combined organic extracts were washed with water (2×20 mL), brine (20 mL), and dried (MgSO$_4$). After filtration, the filtrate was concentrated and the residue was purified on a silica gel column, which gave 157 mg (84%) of desired product as a colorless sticky material.

$^1$H NMR (DMSO-d$_6$): δ 8.65 (s, 1H), 8.30 (d, J=0.5 Hz, 1H), 7.40-7.25 (m, 15H), 5.29 (d, J=0.5 Hz, 1H), 4.71 (dd, J=15.6, 11.6 Hz, 2H), 4.63 (dd, J=15.4, 11.5 Hz, 2H), 4.57 (dd, J=16.4, 11.8 Hz, 2H), 4.23-4.18 (m, 1H), 4.12 (d, J=7.9 Hz, 1H), 4.10 (s, 3H), 3.79 (dd, J=10.9, 3.2 Hz, 1H), 3.71 (dd, J=10.7, 4.5 Hz, 1H), 1.19 (s, 3H); MS (ES$^+$) 567.39 (M+1), 589.37 (M+23).

Step 2: To a suspension of 10% Pd—C (0.05 g) in methanol (3 mL) was added a solution of compound from Step 1 (0.15 g, 0.264 mmol) in MeOH (10 mL) followed by 1N HCl (0.79 mL, 0.79 mmol). The mixture was hydrogenated at 60 psi for 6 h and filtered through a small pad of Celite and the filtrate was concentrated to dryness. The residue was purified on a column of silica gel using CMA-80 in chloroform (0 to 10%), which afforded 65 mg (83.1%) of desired product as a colorless solid.

$^1$H NMR (DMSO-d$_6$): δ 8.64 (s, 1H), 8.37 (d, J=0.8 Hz, 1H), 5.02 (d, J=0.8 Hz, 1H), 5.01 (d, 1H, D$_2$O exchangeable), 4.88 (dd, J=6.0, 4.7 Hz, 1H, D$_2$O exchangeable), 4.78 (s, 1H, D$_2$O exchangeable), 4.10 (s, 3H), 3.88-3.83 (m, 1H), 3.81-3.72 (m, 2H), 3.64-3.57 (m, 1H), 0.90 (s, 3H); IR (KBr): 3399.7, 2926.2, 1623.4, 1552.7, 1486.2, 1444.1, 1371.7, 1321.0, 1226.8, 1184.9, 1154.3, 1105.2, 1076.1, 1045.8, 925.4, 870.1, 835.2, 796.6, 698.3, 642.4 and 591.1 cm−1; MS (ES$^+$) 297.44 (M+1); Anal. Calcd for C$_{13}$H$_{16}$N$_2$O$_6$.0.25H$_2$O: C, 51.91; H, 5.52; N, 9.31. Found: C, 52.09; H, 5.65; N, 9.09.

Example B-14

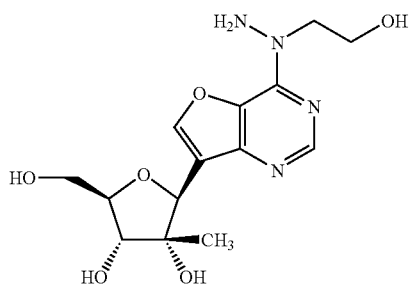

4-[(N-1-Hydroxyethyl)hydrazino]-7-β-(2'-C-methyl-
D-ribofuranosyl)-furo[3,2-d]pyrimidine (Scheme
B-3)

Step 1: To a stirred solution of compound from Example B-12 (0.2 g, 0.35 mmol) in ethanol (10 mL) and chloroform (5 mL) was added N-hydroxyethylhydrazine (0.079 g, 1.05 mmol) at room temperature and stirred for 48 h. After concentrating the reaction mixture, the residue was diluted with water (10 mL) and extracted with chloroform (3×20 mL). The combined organic extracts were washed with brine (10 mL) and dried (MgSO$_4$). After filtration, the filtrate was concentrated and the residue was purified on silica gel column using methanol in chloroform (0 to 5%), which afforded 186 mg (87.1%) of desired product.

$^1$H NMR (DMSO-d$_6$): δ 8.29 (s, 1H), 8.13 (s, 1H), 7.39-7.25 (m, 15H), 5.26 (s, 1H), 5.13 (s, 2H, D$_2$O exchangeable), 4.75 (t, J=5.4 Hz, 1H, D$_2$O exchangeable), 4.73-4.53 (m, 6H), 4.20-4.11 (m, 2H), 3.88 (t, J=6.4 Hz, 2H), 3.78 (dd, J=10.9, 2.6 Hz, 1H), 3.72-3.67 (m, 3H), 1.20 (s, 3H); MS, (ES$^-$) 609.28 (M−1).

Step 2: To a stirred solution of compound from Step 1 (180 mg, 0.29 mmol) in methylene chloride (20 mL) was added 1M solution of boron trichloride in dichloromethane (2.95 mL, 2.95 mmol) at −78° C. and stirred further at this temperature for 1.5 h. After the temperature became 0° C., it was quenched by adding chloroform (2 mL) and methanol (3 mL). To the mixture was added aqueous saturated ammonia (5 mL) and it was stirred for 30 min at room temperature. After concentration, the residue was dissolved in methanol (10 mL), treated with 1M dry HCl in methanol (2 mL) and stirred for 1 h. The resultant suspension was concentrated to dryness and the residue was purified on a silica gel column using CMA-80 in chloroform (0 to 10%), which afforded 68 mg (68.8%) of desired product as a colorless solid; mp 84-92° C.

$^1$H NMR (DMSO-d$_6$): δ 8.25 (s, 1H), 8.17 (s, 1H), 5.16 (bs, 3H, D$_2$O exchangeable), 4.99-4.95 (m, 2H, D$_2$O exchangeable), 4.80 (s, 1H), 4.77-4.73 (m, 1H, D$_2$O exchangeable), 3.92-3.86 (m, 3H), 3.80-3.66 (m, 4H), 3.63-3.55 (m, 1H), 0.89 (s, 3H); IR (KBr) 3412.8, 2926.0, 1612.5, 1577.1, 1539.9, 1487.4, 1437.0, 1352.1, 1305.8, 1072.4, 1045.4, 830.3, 788.9, 634.6 and 588.3 cm$^{-1}$; MS (ES$^+$) 341.39 (M+1), 363.37 (M+23), (ES$^-$) 339.36 (M−1); Anal. Calcd for C$_{14}$H$_{20}$N$_4$O$_6$.0.25H$_2$O: C, 48.76; H, 5.99; N, 16.24. Found: C, 49.01; H, 6.08; N, 15.71.

Example B-15

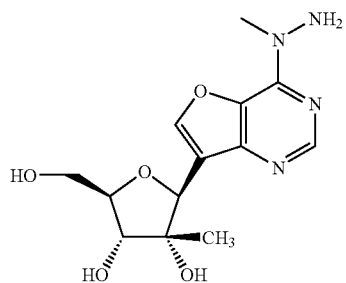

4-[(N-1-Methyl)hydrazino]-7-β-(2'-C-methyl-D-ribofuranosyl)-furo[3,2-d]pyrimidine (Scheme B-3)

Step-1: This was prepared according to the procedure used for Example B-14 (Step 1), using N-methylhydrazine instead of N-hydroxyethylhydrazine, yield 89%.

$^1$H NMR (DMSO-d$_6$): δ 8.29 (s, 1H), 8.12 (d, J=0.7 Hz, 1H), 7.38-7.25 (m, 15H), 5.25 (s, 1H), 5.20 (s, 2H, D$_2$O exchangeable), 4.72 (s, 2H), 4.68-4.53 (m, 4H), 4.20-4.10 (m, 2H), 3.74 (ddd, J=23.7, 10.7, 2.6 Hz, 2H), 3.37 (s, 3H), 1.19 (s, 3H); MS (ES$^+$) 581.36 (M+1), 603.31 (M+23).

Step 2: This was prepared according to the procedure used for Example B-2 (Step 2), using product from Step 1; mp 70-84° C., yield 87%.

$^1$H NMR (DMSO-d$_6$): δ 8.25 (d, J=0.56 Hz, 1H), 8.16 (s, 1H), 5.23 (s, 2H, D$_2$O exchangeable), 5.06 (dd, J=6.7, 4.7 Hz, 1H, D$_2$O exchangeable), 4.96 (d, J=7.5 Hz, 2H, D$_2$O exchangeable), 4.80 (s, 1H), 3.90 (dd, J=8.66, 6.9 Hz, 1H), 3.80-3.71 (m, 2H), 3.64-3.56 (m, 1H), 3.37 (s, 3H), 0.88 (s, 3H); IR (KBr): 3821.1, 2926.6, 1663.4, 1615.1, 1581.2, 1537.3, 1497.4, 1441.6, 1413.8, 1355.9, 1306.4, 1109.1, 1074.3, 1041.6, 957.8, 868.0, 835.2, 790.1, 636.5 and 589.0 cm$^{-1}$; M; MS (ES$^+$) 311.49 (M+1), 333.45 (M+23), (ES$^-$) 309.45 (M−1); Anal. Calcd for C$_{13}$H$_{18}$N$_4$O$_5$I.0.25H$_2$O: C, 49.59; H, 5.92; N, 17.79. Found: C, 49.76; H, 6.13; N, 16.97.

Example B-16

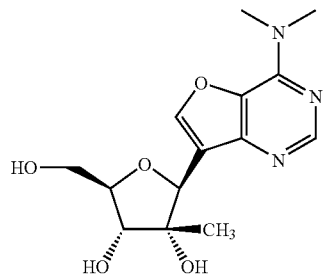

4-Dimethylamino-7-β-(2'-C-methyl-D-ribofuranosyl)-furo[3,2-d]pyrimidine (Scheme B-3)

Step 1: To a stirred solution of compound from Example B-12 (0.11 g, 0.19 mmol) was added 40% solution of N,N-dimethylamine in water (5 mL) at room temperature and was stirred at same temperature for 18 h. After concentrating the reaction mixture, the residue was purified on a column of silica gel using ethyl acetate and hexanes mixture as eluent to afford 106 mg (96.3%) of desired product.

$^1$H NMR (DMSO-d$_6$): δ 8.32 (s, 1H), 8.14 (s, 1H), 7.37-7.25 (m, 15H), 5.25 (s, 1H), 4.72-4.52 (m, 6H), 4.19-4.11 (m, 2H), 3.78 (dd, J=10.7, 2.6 Hz, 1H), 3.69(dd, J−10.9, 3.9 Hz, 1H), 3.30 (bs, 6H), 1.20 (s, 3H); MS (ES$^+$) 580.34 (M+1), 602.40 (M+23); Anal. Calcd for C$_{35}$H$_{37}$N$_3$O$_5$: C, 72.51; H, 6.43; N, 7.24. Found: C, 72.42; H, 6.56; N, 7.17.

Step 2: To a suspension of 10% Pd—C (20 mg) in methanol (3 mL) was added a solution of compound from Step 1 (0.09 g, 0.155 mmol) in MeOH (20 mL) followed by 1N HCl (1 mL, 1 mmol). The mixture was hydrogenated at 70 psi for 3 h and filtered through a small pad of Celite and the filtrate was concentrated to dryness. The residue was dissolved in methanol (2 mL) and triturated with ether (2×3 mL). The solid was separated and collected by filtration to afford 40 mg (83.4%) of desired product as a colorless solid.

$^1$H NMR (DMSO-d$_6$-D$_2$O): δ 8.57 (s, 1H), 8.41 (s, 1H), 4.99 (s, 1H), 3.84-3.60 (m, 4H), 3.45 (bs, 6H), 0.87 (s, 3H); MS (ES$^+$) 310.38 (M+1); Anal. Calcd for C$_{14}$H$_{19}$N$_3$O$_5$.3HCl.1.5H$_2$O.0.15Et$_2$O: C, 38.38; H, 5.84; N, 9.19. Found: C, 38.29; H, 5.50; N, 8.95.

Example B-17

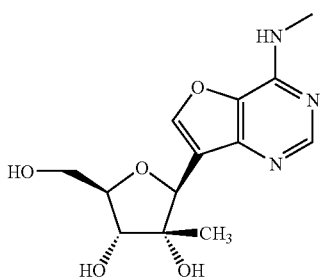

4-Methylamino-7-β-(2'-C-methyl-D-ribofuranosyl)-furo[3,2-d]pyrimidine (Scheme B-3)

This was prepared according to the procedure used for Example B-16, using methylamine instead of dimethylamine, yield 63% in two steps.

$^1$H NMR (DMSO-$d_6$): δ 8.30 (s, 1H), 8.16(s, 1H), 7.84 (d, 1H, $D_2O$ exchangeable), 5.07 (dd, J=6.5, 4.5 Hz, 1H, $D_2O$ exchangeable), 4.97 (d, J=6.5 Hz, 1H, $D_2O$ exchangeable), 4.96 (s, 1H), 4.77 (s, 1H, $D_2O$ exchangeable), 3.92 (dd, J=8.4, 6.9 Hz, 1H), 3.80-3.72 (m, 2H), 3.64-3.56 (m, 1H), 2.95 (d, J=4.5 Hz, 3H), 0.89 (s, 3H); MS (ES$^+$) 296.51 (M+1), 318.45 (M+23), (ES$^-$) 294.47 (M–1).

Example B-18

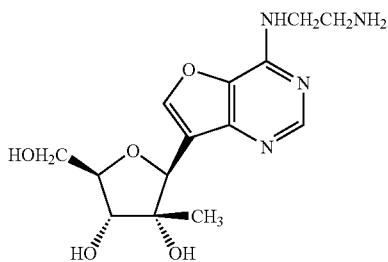

4-Aminoethylamino-7-β-(2'-C-methyl-D-ribofuranosyl)-furo[3,2-d]pyrimidine (Scheme B-3)

Step 1: A solution of compound from Example B-12 (212 mg, 0.37 mmol) in ethanol (15 mL) and chloroform (15 mL) was treated with ethane-1,2-diamine (0.5 mL, 7.4 mmol) followed by stirring at room temperature for 16 h. Additional ethane-1,2-diamine (0.25 mL, 3.7 mmol) was added and stirring was continued for 6 h. The reaction mixture was concentrated and purified on a silica gel column using chloroform/CMA-80 (1:0 to 0:1) as eluent to give 157 mg (71%) of desired product as a light yellow oil.

$^1$H NMR (MeOH-$d_4$): δ 8.31 (s, 1H), 8.05 (d, J=0.7 Hz, 1H), 7.44-7.20 (m, 15H), 5.37 (d, J=0.7 Hz, 1H), 4:79 (s, 2H), 4.64 (s, 2H), 4.64-4.50 (m, 2H), 4.34-4.26 (m, 1H), 4.15 (d, J=7.9 Hz, 1H), 3.88-3.60 (m, 2H), 3.65 (t, J=6.2 Hz, 2H), 2.93 (t, J=6.2 Hz, 2H), 1.19 (s, 3H); IR (neat, cm$^{-1}$): 3363, 2867, 1635, 1497, 1090; MS (ES$^+$) 595.46 (M+H)$^+$ Anal. Calcd for $C_{35}H_{38}N_4O_5 \cdot 0.5H_2O$: C, 69.63; H, 6.51; N, 9.28. Found: C, 69.59; H, 6.46; N, 9.22.

Step 2: A solution of product from Step 1 (120 mg, 0.20 mmol) in dichloromethane (3.7 mL) was cooled to –78° C. and treated with BCl$_3$ dropwise (1M in dichloromethane, 2.0 mL) followed by stirring at –78° C. for 2 h and at –25° C. for 2 h. The reaction mixture was treated with CH$_2$Cl$_2$:MeOH (1:1, 2.2 mL) and stirred at –15° C. for 0.5 h. It was then neutralized with conc. NH$_4$OH at 0° C. and stirred at room temperature for 15 min followed by concentration under vacuum. The residue was treated with MeOH (12 mL) and 20% HCl in MeOH (15 mL) and stirred at room temperature for 1 h followed by concentration. The residue was purified on a silica gel column using CMA-80:CMA-50 (1:0 to 1:1) as eluent to give 62 mg (96%) of desired product as a yellow solid.

$^1$H NMR (MeOH-$d_4$): δ 8.39 (s, 1H), 8.09 (d, J=0.9 Hz, 1H), 5.12 (d, J=0.9 Hz, 1H), 4.04-3.78 (m, 4H), 3.91 (t, J=5.8 Hz, 2H), 3.28 (t, J=5.8 Hz, 2H), 1.02 (s, 3H); IR (KBr, cm$^{-1}$) 3367, 1642, 1507, 1410, 1075; MS (ES$^+$) 325.46 (M+H)$^+$.

Example B-19

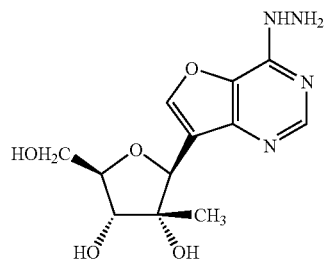

4-Hydrazino-7-β-(2'-C-methyl-D-ribofuranosyl)-furo[3,2-d]pyrimidine (Scheme B-3)

Step 1: A solution of compound from Example B-12 (219 mg, 0.38 mmol) in ethanol (15 mL) and chloroform (15 mL) was treated with hydrazine (98%, 0.05 mL, 1.56 mmol) followed by stirring at room temperature for 16 h. Additional hydrazine (0.10 mL, 3.12 mmol) was added and stirring was continued for 23 h. The reaction mixture was concentrated and purified on a silica gel column using chloroform/CMA-80 (1:0 to 2:1) as eluent to give 129 mg (60%) of desired product as an off-white solid.

$^1$H NMR (MeOH-$d_4$): δ 8.37 (s, 1H), 8.07 (d, J=0.9 Hz, 1H), 7.45-7.20 (m, 15H), 5.39 (d, J=0.9 Hz, 1H), 4.81 (s, 2H), 4.70-4.54 (m, 4H), 4.34-4.27 (m, 1H), 4.17 (d, J=7.9 Hz, 1H), 3.90-3.71 (m, 2H), 1.21 (s, 3H); IR (neat, cm$^{-1}$) 3316, 3030, 2895, 1624, 1453, 1088; MS (ES$^+$) 567.44 (M+H)$^+$; Anal. Calcd for $C_{33}H_{34}N_4O_5$: C, 69.95; H, 6.05; N, 9.89. Found: C, 69.86; H, 6.02; N, 9.69.

Step 2: A solution of compound from Step 1 (98 mg, 0.17 mmol) in dichloromethane (3.1 mL) was cooled to –78° C. and treated with BCl$_3$ (1M in dichloromethane, 1.7 mL) dropwise followed by further stirring at –78° C. for 2 h and at –25° C. for 2 h. The reaction mixture was treated with CH$_2$Cl$_2$/MeOH (1:1, 1.9 mL) and stirred at –15° C. for 0.5 h. It was then neutralized with conc. NH$_4$OH at 0° C. and stirred at room temperature for 15 min followed by concentration under vacuum. The residue was treated with MeOH (10 mL) and 20% HCl in MeOH (12.5 mL) and stirred at room temperature for 1 h followed by concentration. The residue was purified on a silica gel column using chloroform/CMA-80 (1:0 to 0:1) as eluent to give 32 mg (64%) of desired product as a light brown solid.

$^1$H NMR (MeOH-d$_4$): δ 8.04 (s, 1H), 7.79 (s, 1H), 4.94 (s, 1H), 3.92-3.64 (m, 4H), 0.82 (s, 3H); IR (KBr, cm$^{-1}$): 3316, 2927, 1634, 1072; MS (ES$^+$): 297.47 (M+H)$^+$.

Example B-20

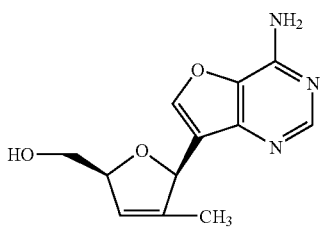

((2S,5R)-(5-(4-Aminofuro[3,2-d]pyrimidin-7-yl)-4-methyl-2,5-dihydrofuran-2-yl)methanol (Scheme B-6)

Step 1: To a solution of compound from Example A-7 (Step 7) (55 g, 0.139 mmol) in DMF (695 mL) was added tert-butoxybis(dimethylamino)methane (73 g, 0.417 mmol) and heated at 60° C. for 6 h. After evaporating most of the solvent under reduced pressure, the residue was suspended in water (500 mL) and extracted with Et$_2$O (3×350 mL). Combined organic extracts were washed with water (2×250 mL), dried over MgSO$_4$, filtered and the filtrate was concentrated to give 72 g of desired product, dimethyl-[2-(3-methyl-5-trityloxymethyl-2,5-dihydro-furan-2-yl)-propenyl]-amine, which was used as such for the next step.

Step 2: To a solution of compound from Step 1 (70 g crude) in CHCl$_3$ (1200 mL), was added water (750 mL) followed by trifluoroacetic acid (17 mL). The reaction mixture was stirred at room temperature for 17 h and the organic layer was separated. The aqueous layer was further extracted with CHCl$_3$ (200 mL) and the combined organic layers were washed with water (500 mL), sat. NaHCO$_3$ (200 mL), and dried over MgSO$_4$. After filtration, the filtrate was concentrated to give 48 g of the corresponding enol. This was used as such in the next step.

Step 3: To a stirring suspension of the compound obtained from Step 2 (47 g crude), DMF (1000 mL), KF (12.8 g, 0.22 mol) and 18-crown-6 (23 g, 0.088 mol) was added chloroacetonitrile (25 g, 0.333 mol) and the reaction mixture was stirred for 24 h at room temperature. After removing most of the solvent under reduced pressure, water (1000 mL) was added and the mixture was extracted with Et$_2$O (2×700 mL). The combined organic extracts were washed with water (2×250 mL), dried over MgSO$_4$, and filtered. The filtrate was concentrated and the residue was purified on a column of silica gel (450 g) using 10 to 40% EtOAc in hexanes to give 21 g (32% in three steps) of corresponding cyanomethyl enol ether.

MS (ES$^+$) 485.21 (M+Na).

Step 4: To a cold solution (−78° C.) of the compound obtained from Step 3 in THF (530 mL) was added LDA (2M in THF, 65 mL) at such a rate that the reaction temperature never exceeded above −70° C. After another 0.5 h stirring at −78° C., the reaction mixture was quenched with water (50 mL) and allowed to attain room temperature. After removing the solvent, the residue was purified on a silica gel column (450 g) using 0 to 20% EtOAc in hexanes as eluent. Two more successive column chromatography were needed to purify the compound and to give 3.02 g (15%) of 3-amino-4-((2S)-3-methyl-5-(trityloxymethyl)-2,5-dihydrofuran-2-yl)furan-2-carbonitrile, as a white solid; mp 68° C. (R$_f$=0.5 in 30% EtOAc in hexanes).

$^1$H NMR (DMSO-d$_6$): 7.62 (s, 1H), 7.23-7.42 (m, 15H), 5.56-5.68 (m, 4H), 5.07 (m, 1H), 2.96 (m, 2H), 1.62 (s, 3H).); IR (KBr): 3357, 2864, 2203, 1635, 1444, 1071, 704 cm$^{-1}$; MS (ES$^+$) 485.34 (M+Na); Anal. Calcd for C$_{30}$H$_{26}$N$_2$O$_3$: C, 77.90; H, 5.66; N, 6.05. Found: C, 77.59; H, 5.75; N, 5.85.

Further elution provided 2.17 g (11%) of 3-amino-4-((2R)-3-methyl-5-(trityloxymethyl)-2,5-dihydrofuran-2-yl)furan-2-carbonitrile as a white solid, mp 138-144° C. (R$_f$=0.48 in 30% EtOAc in hexanes).

$^1$H NMR (DMSO-d$_6$): 7.20-7.40 (m, 16H), 5.87 (br, 2H), 5.65 (m, 1H), 5.53 (m, 1H), 4.86 (m, 1H), 3.06 (dd, J=9.6 and 6.7 Hz, 1H), 2.9 (dd, J=9.6 and 3.0 Hz, 1H) 1.66 (s, 3H); IR (KBr): 3361, 2868, 2201, 1637, 1444, 1085, 700 cm$^{-1}$; MS (ES$^+$) 485.28 (M+Na); Anal. Calcd for C$_{30}$H$_{26}$N$_2$O$_3$: C, 77.90; H, 5.66; N, 6.05. Found: C, 77.72; H, 5.75; N, 5.93.

Step 5: A mixture of compound from Step 4, 3-amino-4-((2R)-3-methyl-5-(trityloxymethyl)-2,5-dihydrofuran-2-yl)furan-2-carbonitrile (1.45 g, 3.13 mol) and formamidine acetate (6.5 g, 62.69 mmol) in EtOH (25 mL) was heated at reflux for 24 h. Additional formamidine acetate (3.25 g, 31.34 mmol) was added and continued heating for further 40 h. Most of the solvent was evaporated, water (100 mL) was added and the mixture was extracted with EtOAc (2×75 mL). The combined organic extracts were washed with water (2×50 mL), dried over MgSO$_4$ and filtered. The filtrate was concentrated and the residue was purified on a silica gel column (40 g) using 0 to 10% EtOAc in hexanes as eluent to give 1.2 g (78%) of 7-((2R)-3-methyl-5-(trityloxymethyl)-2,5-dihydrofuran-2-yl)furo[3,2-d]pyrimidin-4-amine as a white solid; mp 128-132° C. (R$_f$=0.67 in 10% MeOH in CHCl$_3$).

$^1$H NMR (DMSO-d$_6$): 8.06 (s, 1H), 7.97 (s, 1H), 7.16-7.37 (m, 17H), 5.77 (m, 1H), 5.64(s, 1H), 4.96 (m, 1H), 3.30 (m, 1H), 2.98 (m, 1H), 1.61 (s, 3H); IR (KBr): 3328, 1645, 1438, 704 cm$^{-1}$; MS (ES$^+$) 512.32 (M+Na); Anal. Calcd for C$_{31}$H$_{27}$N$_3$O$_3$.0.5H$_2$O: C, 74.67; H, 5.66; N, 8.42. Found: C, 74.53; H, 5.53; N, 8.25.

Step 6: To a solution of compound from Step 6, 7-((2R)-3-methyl-5-(trityloxymethyl)-2,5-dihydrofuran-2-yl)furo[3,2-d]pyrimidin-4-amine (40 mg, 0.082 mmol) in dioxane (4 mL) was added 4N aqueous HCl (0.125 mL) at room temperature. The reaction mixture was stirred at room temperature for 30 min and the mixture was evaporated, redissolved in MeOH (3 mL) and neutralized with 0.1 N NaOH. The solution was purified on a silica gel column using 0 to 10% of MeOH in CHCl$_3$ to give 12 mg (23%) of desired target, ((2S,5R)-5-(4-aminofuro[3,2-d]pyrimidin-7-yl)-4-methyl-2,5-dihydrofuran-2-yl)methanol as a thick oil.

$^1$H NMR (DMSO-d$_6$): 8.16 (s, 1H), 8.04 (s, 1H), 5.75-5.79 (m, 1H), 5.61-5.65 (m, 1H), 4.90-4.96 (m, 1H), 3.87 (dd, J=12.4 and 2.0 Hz, 1H), 3.70 (dd, J=12.4 and 2.8 Hz, 1H) and 1.58 (s, 3H); MS (ES$^+$) 248.45 (M+H).

Example B-21

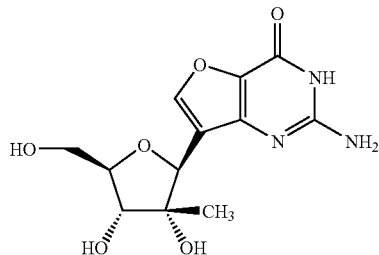

2-Amino-7-β-(2'-C-methyl-D-ribofuranosyl)-furo[3,2-d]pyrimidin-4(3H)-one (Scheme B-4)

Steps 1 through 4 were carried out the same way as in Example B-1 starting from A-5 instead of A-2.

Step 4 product: $^1$H NMR (DMSO-d$_6$): δ 7.50 (d, J=0.8 Hz, 1H), 7.39-7.25 (m, 15H), 5.29 (bs, 2H), 4.88 (1, 1H), 4.64-4.53 (m, 6H), 4.30-4.15 (m, 3H), 3.92 (d, J=5 Hz, 1H), 3.73-3.67 (m, 2H), 1.24 (t, 3H), 1.15 (s, 3H); IR (KBr) 3462, 3349, 2871, 1705, 1672, 1632, 1591, 1537, 1455, 1369, 1323, 1107, 1026 cm$^{-1}$; MS (ES$^+$) 572.31 (M+Na); Anal. Calcd for C$_{34}$H$_{37}$NO$_7$: C, 71.43; H, 6.52; N, 2.45. Found: C, 71.15; H, 6.50; N, 2.26.

Step 5: To a solution of product from Step 4 (0.8 g, 1.4 mmol) in pyridine (14 mL) was added triethylamine (0.98 mL, 7 mmol), mercury (II) chloride (0.76 g, 2.8 mmol), 1,3 dicarbomethoxy-2-methyl-2-thiopsuedourea (0.58 g, 2.8 mmol) and the reaction mixture was stirred at room temperature overnight. Solvent was removed under vacuum and the residue was triturated with ethyl acetate (100 mL) and filtered through a pad of Celite® to remove insoluble impurities. The filtrate was concentrated under vacuum and the residue obtained was purified by column chromatography (silica gel 40 g, eluting with 0-75% ethyl acetate in hexanes) to furnish 0.44 g (10%) of desired product as yellow oil.

$^1$H NMR (DMSO-d$_6$): δ 11.20 (s, 1H), 9.82 (s, 1H), 7.78 (d, J=0.9 Hz, 1H), 7.35-7.22 (m, 15H), 5.25 (s, 1H), 4.60-4.35 (m, 7H), 4.22-4.11 (m, 2H), 3.79 (d, J=4.5 Hz, 1H), 3.64 (m, 2H), 3.60 (s, 3H), 3.49 (s, 3H), 1.20 (t, 3H), 1.07 (s, 3H); IR (KBr) 3439, 3285, 3152, 2951, 2363, 1810, 1734, 1629, 1449, 1409, 1271, 1225, 1184, 1111, 1067, 737, 698 cm$^{-1}$; MS (ES$^+$) 730.42 (M+1); Anal. Calcd for C$_{39}$H$_{43}$N$_3$O$_{11}$.0.5H$_2$O: C, 63.39; H, 6.01; N, 5.69. Found: C, 63.04; H, 5.94; N, 5.97.

Step 6: To a solution of product from Step 5 (0.4 g, 0.55 mmol) in methanol (6 mL) was added sodium methoxide (5.4M solution in methanol, 0.126 mL) and stirred at room temperature overnight. After 24 h, additional sodium methoxide (5.4M in methanol, 0.126 mL) was added and stirred for 6 h. The reaction was quenched with glacial acetic acid (0.09 mL, 1.5 mmol) and concentrated under vacuum to dryness. The residue obtained was purified by column chromatography (silica gel 10 g, eluting with 0-25% CMA-80 in chloroform) to furnish 0.304 g (89%) of desired product, 2-methoxycarbonylamino-7-(3,4-bis-benzyloxy-5-benzyloxymethyl-3-methyl-tetrahydro-furan-2-yl)-3H-furo[3,2-d]pyrimidin-4-one, as yellow oil.

Step 7: To the product from Step 6 (0.3 g, 0.49 mmol) in methanol (2.5 mL) was added 1N NaOH (2.5 mL, 2.5 mmol) and heated at 50° C. for 3 h. Additional 1N NaOH (2.5 mL, 2.5 mmol) was added and continued heating at 50° C. for 3 h. The reaction mixture was cooled to room temperature and pH adjusted to 6 using glacial acetic acid (0.3 mL). The reaction mixture was concentrated under vacuum to remove methanol and the yellow solid obtained was collected by filtration, washed with water and hexane to furnish 0.25 g (90%) of desired product as a yellow solid; mp 80-84° C.

$^1$H NMR (DMSO-d$_6$): δ 11.11 (bs, 1H), 7.89 (s, 1H), 7.38-7.25 (m, 15H), 6.38 (bs, 2H), 5.04 (s, 1H), 4.75-4.52 (m, 6H), 4.16-4.11 (m, 1H), 4.05 (d, J=7.5 Hz, 1H), 3.80-3.67 (m, 2H), 1.22 (s, 3H); IR (KBr) 3324, 3144, 3030, 2897, 2869, 1696, 1643, 1532, 1496, 1453, 1364, 1317, 1099, 1026, cm$^{-1}$; MS (ES$^+$) 568.38 (M+1), (ES$^-$): 566.22 (M−1); Anal. Calcd for C$_{33}$H$_{33}$N$_3$O$_6$.0.5H$_2$O: C, 68.72; H, 5.95; N, 7.29. Found: C, 68.94; H, 5.75; N, 7.21.

Step 8: A mixture of compound from Step 7 (0.2 g, 0.35 mmol) in ethanol (5 mL) containing Pd—C (10%, 40 mg) and 1N HCl (1.75 mL) was hydrogenated at 70 psi for 12 h. The reaction mixture was filtered through Celite to remove catalyst and the filtrate was concentrated under vacuum to dryness. The residue was purified by column chromatography (silica gel 4 g, eluting with 0-25% methanol in chloroform) to furnish 0.082 g (67%) of desired product as an off-white solid.

$^1$HNMR (DMSO-d$_6$): δ 11.02 (bs, 1H, D$_2$O exchangeable), 7.93 (d, J=0.7 Hz, 1H), 6.39 (bs, 2H, D$_2$O exchangeable), 4.96-4.82 (m, 2H, D$_2$O exchangeable), 4.81 (d, J=0.7 Hz, 1H), 4.77-4.60 (m, 1H, D$_2$O exchangeable), 3.76-3.66 (m, 3H), 3.61-3.53 (m, 1H), 0.94 (s, 3H); $^{13}$CNMR (DMSO-d$_6$/D$_2$O): δ 153.75, 147.28, 132.59, 121.66, 82.45, 80.57, 78.23, 74.27, 73.92, 61.22, 22.07; IR (KBr) 3381.5, 2926.8 1699.64, 1645.5, 1533.4, 1490.0, 1373.3, 1179.2, 1118.7, 1075.0, 1040.3, 881.6, 822.0, 781.2, 673.4, 582.5 and 492.1 cm$^{-1}$; MS (ES$^+$) 298.37 (M+1), (ES$^-$) 296.35 (M−1).

Example B-22

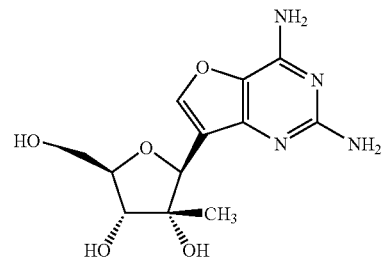

2,4-Diamino-7-β-(2'-C-methyl-D-ribofuranosyl)-furo[3,2-d]pyrimidine (Scheme B-5)

Step 1: To a solution of compound from Example B-21, Step 7 (0.5 g, 0.85 mmol) in CH$_3$CN (5 mL) was added benzyl triethylammonium chloride (0.38 g, 1.7 mmol) and N,N dimethylaniline (0.16 mL, 1.28 mmol). After the reaction mixture was heated to 80° C., phosphorus oxychloride (0.5 mL, 5.1 mmol) was added and maintained at this temperature for 1 h. The reaction mixture was concentrated, ice cold water (20 mL) was added to it and was extracted with CHCl$_3$ (50 mL). The organic layer was separated, washed with aqueous sodium bicarbonate solution (2×20 mL) and dried over MgSO$_4$. After filtration, the filtrate was concentrated and the residue was purified on a silica gel column using 0 to 10% MeOH in CHCl$_3$ to give 0.41 g (81%) of the desired product.

MS (ES$^-$) 585.20 (M−1).

Step 2: Compound from Step 1 (0.35 g, 0.59 mmol) was taken in a pressure vessel with methanol saturated with ammonia (20 mL) and the vessel was heated to 100° C. for 12 h. After evaporation of the solvent, the residue was partitioned between CHCl$_3$ (50 mL) and water (50 mL). The organic layer was collected, dried over MgSO$_4$, filtered and the filtrate was concentrated. The residue was dissolved in EtOH (20 mL) and 10% Pd—C (50 mg) and 1N HCl (0.2 mL) were added to it. The reaction was shaken under hydrogen atmosphere (70 psi) for 18 h and filtered through Celite. The filtrate was concentrated and the residue was purified on a column of silica gel using 0 to 50% CMA-50 in CMA-80 to give 81 mg (61%) of the desired target. P $^1$H NMR (CD$_3$OD) δ in ppm 7.60 (s, 1H), 4.80 (s, 1H), 3.85 (m, 1H), 3.75 (m, 2H), 3.60 (m, 1H), 0.80 (s, 3H); MS (ES$^+$) 297.50 (M+H)$^+$.

Example B-23

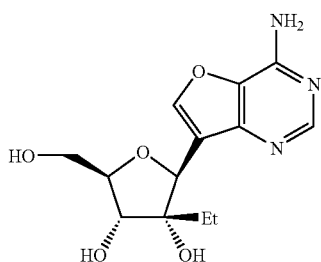

4-Amino-7-β-(2'-C-ethyl-D-ribofuranosyl)-furo[3,2-d]pyrimidine (Scheme B-6)

This compound was prepared from the product of Example A-8 according to the procedures used for Example B-20 except at the last step of deprotection. The last step of deprotection was achieved through catalytic hydrogenation in the presence of 10% Pd—C in ethanol containing two equivalents of HCl.

$^1$H NMR (DMSO-d$_6$) δ 8.30 (s, 1H), 8.25 (s, 1H), 7.45 (brs, 2H), 5.1 (m, J=5.0 Hz, 1H), 5.00 (m, 1H), 4.50 (m, 1H), 4.12 (m, 3H), 8.80-3.60 (m, 3H), 3.10 (m, 1H), 1.20 (m, 2H), 0.70 (t, J=7.1 Hz, 1H); MS (ES$^+$) 296.49 (M+H)$^+$; Anal. Calcd for C$_{13}$H$_{17}$N$_3$O$_5$·HCl·H$_2$O: C, 44.68; H, 5.77; N, 12.0. Found: C, 44.78; H, 5.44; N, 11.34.

Example B-24

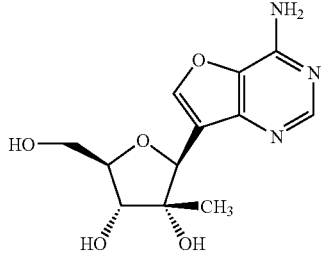

4-Amino-7-β-(2'-C-methyl-D-ribofuranosyl)-furo[3,2-d]pyrimidine (Scheme B-6)

Step 1: A solution of compound from Example A-3, Step 3 (4.02 g, 8.63 mmol) in DMF (45 mL) was treated with t-BuOCH(NMe$_2$)$_2$ (12.07 g, 69.25 mmol) and stirred at room temperature overnight. The reaction mixture was diluted with toluene (800 mL) and washed with water (2×400 mL) and brine (300 mL), and dried over MgSO$_4$. After filtration the filtrate was concentrated to give 5.01 g of the desired product as a light yellow oil, which was used as such for the next step.

Step 2: The product from Step 1 (4.98 g) was dissolved in chloroform (150 mL) and treated with a solution of TFA (2.25 mL) in water (100 mL) and stirred vigorously at room temperature for 17 h. The organic layer was separated and washed with water (2 x), and dried over MgSO$_4$. After filtration, the filtrate was concentrated to give 4.26 g of the desired product as light yellow oil, and was used as such for next step.

Step 3: A mixture of compound from Step 2 (1.55 g), 18-crown-6 (0.66 g, 2.5 mmol) and KF (365 mg, 6.28 mmol) in DMF (30 mL) was treated dropwise with chloroacetonitrile (709 mg, 9.39 mmol) followed by stirring at room temperature for 14 h (TLC showed that TBDPS group was lost). After concentration, the residue was taken in pyridine (10 mL) and treated with trityl chloride (1.35 g, 4.75 mmol) followed by stirring at 70° C. for 19 h. The reaction mixture was diluted with EtOAc (150 mL) and washed with water (2×70 mL) and brine (70 mL), then dried over MgSO$_4$. After filtration and concentration of the filtrate, the residue was purified on a silica gel column using hexanes:ethyl acetate (1:0 to 2:1) as eluent to give 727 mg (43%, three steps) of desired product as a mixture of Z, E, α, and β isomers, as a white foam, which was used as such for the next step.

MS (ES$^+$) 559.30 (M+Na)$^+$.

Step 4: A solution of above mixture from Step 3 (520 mg, 0.97 mmol) in THF (15 mL) was cooled to −78° C. and treated with LDA dropwise (2M in THF/heptane/ethylbenzene, 1.95 mL, 3.9 mmol) followed by stirring at −78° C. for 2 h. The reaction was quenched with water (320 μL) and stirred at room temperature for 1 h. After concentration, the residue was purified on a silica gel column using hexanes:ethyl acetate (1:0 to 3:1) as eluent to give 15 mg (2.9%) of desired product as a light yellow syrup.

$^1$H NMR (CDCl$_3$): δ 7.50-7.18 (m, 16H), 4.71 (s, 1H), 4.35-4.25 (m, 2H), 3.42-3.30 (m, 2H), 1.59 (s, 3H), 1.39 (s, 3H), 1.22 (s, 3H); MS (ES$^+$) 559.26 (M+Na)$^+$.

Step 5: A mixture of compound from Step 4 (23 mg, 0.043 mmol) and formamidine acetate (45 mg, 0.43 mmol) in EtOH (5 mL) was refluxed for 23 h. It was then refluxed for five additional days with addition of formamidine acetate (total of 300 mg added, 2.88 mmol, 100 mg every day for first three days). The reaction mixture was concentrated and purified on a silica gel column using chloroform:methanol (1:0 to 95:5) as eluent to give 14 mg (58%) of desired product as a colorless oil.

$^1$H NMR (MeOH-d$_4$): δ 8.14 (s, 1H), 7.78 (s, 1H), 7.45-7.37 (m, 6H), 7.28-7.10 (m, 9H), 5.07 (s, 1H), 4.20 (d, J=3.0 Hz, 1H), 4.17-4.11 (m, 1H), 3.27 (d, J=5.0 Hz, 2H), 1.53 (s, 3H), 1.27 (s, 3H), 1.06 (s, 3H); MS (ES$^+$) 586.39 (M+Na)$^+$.

Step 6: A solution of compound from Step 5 (14 mg, 0.025 mmol) in MeOH (2 mL) was treated with 20% HCl in MeOH (2.5 mL) and stirred at room temperature for 1 h followed by concentration. The residue was redissolved in a small amount of MeOH and treated with ether to precipitate the desired compound, which was collected by filtration to give 3 mg (43%) of desired product as hydrochloride.

$^1$H NMR (MeOH-d$_4$): δ 8.45 (s, 1H), 8.25 (s, 1H), 5.03 (s, 1H), 4.05-3.81 (m, 3H), 3.76 (d, J=7.3 Hz, 1H), 0.96 (s, 3H); MS (ES$^+$) 282.41 (M+H)$^+$.

Alternate Synthesis:

This compound was also prepared from the benzyl protected tetrahydrofuran derivative:

Step 1: A solution of compound from Example A-4, Step 3 (3.8 g, 6.38 mmol) in DMF (50 mL) was treated with t-BuOCH(NMe$_2$)$_2$ (4.33 g, 24.86 mmol) and stirred at room temperature overnight. The reaction mixture was diluted with toluene (100 mL) and washed with water (75 mL). The aqueous phase was extracted further with toluene (50 mL) and the combined extracts were washed with water (2×) and dried over MgSO$_4$. After filtration, the filtrate was concentrated to give 5.0 g of the desired product which was used as such for the next step.

Step 2: The product from Step 1 (4.9 g) was treated with a solution of THF/HOAc/H$_2$O (1:1:1, 30 mL) and stirred at room temperature for 3 h. The reaction mixture was diluted with chloroform (100 mL) and water (100 mL). The organic layer was separated and washed with water (1×), sat. NaHCO$_3$ (2×), water (1×), and dried over MgSO$_4$. After filtration, the filtrate was concentrated to give 3.08 g of the desired product, which was used as such for next step.

Step 3: A mixture of product from Step 2 (3.0 g), 18-crown-6 (1.02 g, 3.86 mmol) and KF (0.56 g, 4.83 mmol) in DMF (40 mL) was treated dropwise with chloroacetonitrile (1.1 g, 14.49 mmol) followed by stirring at room temperature for 18 h. After concentration, the residue was taken in EtOAc and filtered through Celite. The filtrate was concentrated and the residue was purified on a silica gel column using hexanes:ethyl acetate (1:0 to 2:1) as eluent to give 1.41 g (33%, three steps) of desired product (a mixture of Z, E, α, and β isomers) as a light colorless oil, which was used as such for the next step.

MS (ES$^+$) 685.25 (M+Na)$^+$.

Step 4: A solution of above mixture from Step 3 (817 mg, 1.23 mmol) in THF (19 mL) was cooled to −78° C. and treated with LDA dropwise (1M in THF, 4.92 mL) followed by further stirring at −78° C. for 2 h. The reaction was quenched with water (405 μL) and stirred at room temperature for 1 h. After concentration, the residue was purified on a silica gel column using hexanes:ethyl acetate (1:0 to 3:1) as eluent to give 79 mg (9.7%) of desired product as a light yellow syrup.

$^1$H NMR (CDCl$_3$): δ 7.42-7.14 (m, 12H), 4.94 (d, J=1.2 Hz, 1H), 4.76-4.50 (m, 6H), 4.37-4.29 (m, 1H), 3.95-3.68 (m, 3H), 1.23 (s, 3H); MS (ES$^−$) 659.68 (M−H)$^−$.

Step 5: A mixture of compound from Step 4 (75 mg, 0.113 mmol) and formamidine acetate (300 mg, 2.85 mmol) in EtOH (10 mL) was refluxed for 21 h. Additional formamidine acetate (200 mg, 1.90 mmol) was added and it was refluxed again for 19 h. The reaction mixture was concentrated and purified on a silica gel column using chloroform:methanol (1:0 to 95:5) as eluent to give 62 mg (80%) of desired product as a light yellow syrup.

$^1$H NMR (MeOH-d$_4$): δ 8.45 (s, 1H), 8.29 (d, J=0.7 Hz, 1H), 7.74-7.40 (m, 11H), 5.58 (d, J=0.7 Hz, 1H), 5.15-4.79 (m, 6H), 4.55-4.49 (m, 1H), 4.44 (d, J=7.6 Hz, 1H), 4.16-4.00 (m, 2H), 1.51 (s, 3H); MS (ES$^+$) 710.29 (M+Na)$^+$.

Step 6: A solution of compound from Step 5 (58 mg, 0.084 mmol) in dichloromethane (1.5 mL) was cooled to −78° C. and treated with BCl$_3$ dropwise (1M in dichloromethane, 0.84 mL) followed by stirring at −78° C. for 2 h and at −25° C. for 2.5 h. The reaction mixture was treated with CH$_2$Cl$_2$/MeOH (1:1, 0.9 mL) and stirred at −15° C. for 0.5 h. It was then neutralized with conc. NH$_4$OH at 0° C. and stirred at room temperature for 15 min followed by concentration under vacuum. The residue was treated with MeOH (6 mL) and 20% HCl in MeOH (7.5 mL) and stirred at room temperature for 1 h followed by concentration. The residue was purified on a silica gel column using chloroform:methanol (1:0 to 3:1) as eluent to give the product, which was treated with MeOH (5 mL) and 20% HCl in MeOH (0.5 mL), then stirred for 10 min. After concentration, the residue was re-dissolved in a small amount of MeOH and treated with ether to precipitate the desired compound as HCl salt. The filtration and washing with ether provided 20 mg (75%) of desired product.

$^1$H NMR matched with the compound obtained from the previous approach; IR (KBr, cm$^{-1}$) 3380, 3113, 2693, 1678, 1611, 1079; MS (ES$^+$) 304.36 (M+Na)$^+$.

Example B-25

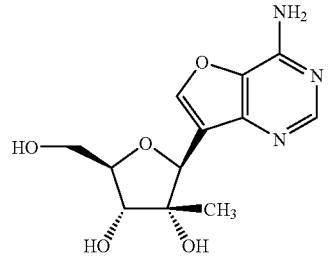

4-Amino-7-α-(2'-C-methyl-D-ribofuranosyl)-furo[3,2-d]pyrimidine (Scheme B-6)

Step 1: When Example B-24 was prepared from Example A-3, at Step 4 in the first approach, another isomer was isolated during chromatography, which corresponded to the alpha isomer (86 mg, 17%).

$^1$H NMR (CDCl$_3$): δ 7.48-7.20 (m, 16H), 4.71 (s, 1H), 4.47 (d, J=1.2 Hz, 1H), 4.33-4.26 (m, 1H), 3.36-3.22 (m, 2H), 1.48 (s, 3H), 1.42 (s, 3H), 1.42 (s, 3H); MS (ES$^+$) 559.94 (M+Na)$^+$.

Step 2: A mixture of compound from Step 1 (65 mg, 0.12 mmol) and formamidine acetate (130 mg, 99%, 1.24 mmol) in EtOH (5 mL) was refluxed for 22 h. Additional formamidine acetate (100 mg) was added and the reaction mixture was refluxed for 7 h followed by concentration. The residue was purified on a silica gel column using chloroform:methanol (1:0 to 95:5) as eluent to give 60 mg (89%) of desired compound, as a light yellow oil.

$^1$H NMR (CDCl$_3$): δ 8.43 (s, 1H), 7.94 (s, 1H), 7.51-7.20 (m, 15H), 5.68 (bs, 2H), 5.17 (s, 1H), 4.49 (s, 1H), 4.35 (t,

J=6.3 Hz, 1H), 3.38-3.22 (m, 2H), 1.52 (s, 3H), 1.49 (s, 3H), 1.39 (s, 3H); MS (ES$^+$): 564.49 (M+H)$^+$.

Step 3: A solution of compound from Step 2 (55 mg, 0.10 mmol) in MeOH (2 mL) was treated with 20% HCl in MeOH (2.5 mL) and stirred at room temperature for 1 h followed by concentration. The residue was redissolved in a small amount of MeOH and treated with ether to precipitate the desired HCl salt, which was collected by filtration to give 19 mg (54%) of desired product as hydrochloride, as yellow solid.

$^1$H NMR (MeOH-d$_4$): δ 8.71 (s, 1H), 8.55 (d, J=0.4 Hz, 1H), 5.17 (s, 1H), 4.45-4.37 (m, 1H), 4.29 (d, J=8.3 Hz, 1H), 4.12-3.87 (m, 2H), 1.45 (s, 3H); IR (KBr, cm$^{-1}$): 3409, 3132, 1677, 1036; MS (ES$^+$) 304.37 (M+Na)$^+$.

Example B-26

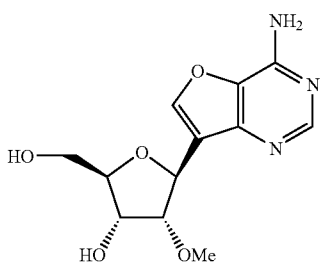

4-Amino-7-β-(2'-O-methyl-D-ribofuranosyl)-furo[3,2-d]pyrimidine (Scheme B-6)

Step 1: A solution of anomeric isomers from Example A-6, Step 3 (3.07 g, 8.36 mmol) in DMF (48 mL) was treated with t-BuOCH(NMe$_2$)$_2$ (10 mL, 48.43 mmol) and stirred at room temperature for 15 h. The reaction mixture was diluted with toluene (300 mL), washed with water (2×150 mL) and brine (150 mL), and dried over MgSO$_4$. After filtration, the filtrate was concentrated to give 3.75 g of desired product as yellow oil, which was used as such for next step.

MS (ES$^+$) 445.48 (M+Na)$^+$.

Step 2: The product from Step 1 (3.7 g crude) was dissolved in chloroform (75 mL) and treated with a solution of TFA (1.1 mL) in H$_2$O (50 mL) followed by vigorous stirring at room temperature for 20 h. The reaction mixture was diluted with chloroform (75 mL) and was washed with water (75 mL). The organic layer was separated and dried over MgSO$_4$. After filtration, the filtrate was concentrated to give 3.67 g of desired product as a yellow oil, which was used as such for next step.

MS (ES$^+$) 396.45 (M+H)$^+$.

Step 3: A mixture of compound from Step 2 (3.62 g), 18-crown-6 (1.78 g, 6.73 mmol) and KF (0.97 g, 16.7 mmol) in DMF (75 mL) was treated dropwise with chloroacetonitrile (1.6 mL, 25 mmol) followed by stirring at room temperature for 23 h. The reaction mixture was diluted with EtOAc (200 mL), washed with water (2×100 mL) and brine (100 mL), and dried over MgSO$_4$. After filtration, the filtrate was concentrated to give 3.24 g of desired product as brown oil, which was used as such for next step.

MS (ES$^+$) 457.40 (M+Na)$^+$.

Step 4: A solution of compound from Step 3 (3.19 g) in THF (95 mL) was cooled to −78° C. and treated with LDA (2M in heptane/THF/ethylbenzene, 14.5 mL) dropwise followed by stirring at −78° C. for 3 h. The reaction was quenched with water (2.4 mL) and stirred at room temperature for 1 h. After concentration, the residue was purified on a silica gel column using hexanes:ethyl acetate (1:0 to 2:1) as eluent to give 863 mg (24% for four steps, R$_f$=0.50, hexanes/EtOAc=2:1) of desired product as a brown oil.

$^1$H NMR (DMSO-d$_6$): δ 7.64 (s, 1H), 7.40-7.28 (m, 10H), 5.79 (s, 2H), 4.74 (d, J=7.3 Hz, 1H), 4.60-4.46 (m, 4H), 4.20-3.95 (m, 2H), 3.88 (dd, J=7.4, 5.1 Hz, 1H), 3.65-3.45 (m, 2H), 3.30 (s, 3H); MS (ES$^+$) 435.44 (M+H)$^+$.

Step 5: A mixture of compound from Step 4 (404 mg, 0.93 mmol) and formamidine acetate (1.96 g, 18.6 mmol) in EtOH (14 mL) was refluxed for 40 h. The reaction mixture was concentrated and purified on a silica gel column using chloroform:methanol (1:0 to 96:4) as eluent to give 317 mg (74%) of desired product as a light brown oil.

$^1$H NMR (CDCl$_3$): δ 8.40 (s, 1H), 7.82 (d, J=,0.9 Hz, 1H), 7.36-7.26 (m, 10H), 5.54 (bs, 2H), 5.28 (dd, J=3.4, 0.8 Hz, 1H), 4.68-4.49 (m, 4H), 4.35-4.28 (m, 1H), 4.22-4.15 (m, 2H), 3.84-3.60 (m, 2H), 3.53 (s, 3H); MS (ES$^+$) 462.43 (M+H)$^+$.

Step 6: A solution of compound from Step 5 (161 mg, 0.35 mmol) in MeOH (15 mL) was treated with 1N aqueous HCl (1 mL) and Pd—C (10%, 60 mg) followed by hydrogenation (∼50 psi) for 6 h. After filtration and concentration, the residue was purified on a silica gel column using chloroform/MeOH (1:0 to 4:1) as eluent to give 57 mg (58%) of desired product.

$^1$H NMR (MeOH-d$_4$): δ 8.25 (s, 1H), 8.08 (d, J=0.4 Hz, 1H), 5.03 (d, J=8.0 Hz, 1H), 4.43 (dd, J=4.9, 2.2 Hz, 1H), 4.18 (dd, J=7.9, 4.9 Hz, 1H), 4.12 (dd, J=4.5, 2.2 Hz; 1H), 3.90-3.67 (m, 2H), 3.39 (s, 3H); IR (KBr, cm$^{-1}$) 3419, 2925, 1656, 1438, 1090; MS (ES$^+$) 282.54 (M+H)$^+$; Anal. Calcd for C$_{12}$H$_{15}$N$_3$O$_5$.0.75 MeOH.0.25H$_2$O: C, 49.43; H, 6.02; N, 13.56. Found: C, 49.02; H, 5.77; N, 13.31.

Example B-27

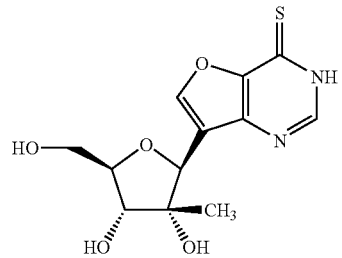

7-β-(2'-C-Methyl-D-ribofuranosyl)-furo[3,2-d]pyrimidin-4(3H)-thione (Scheme B-7)

Step 1: To a solution of compound from Example B-1, Step 2 (17 g, 35.01 mmol) in DMF (250 mL) was added potassium fluoride (4.06 g, 70.02 mmol), 18-crown-6 (7.31 g, 27.65 mmol) followed by chloroacetonitrile (7.93 g, 105.03 mmol) and the mixture was stirred for 18 h at room temperature. The reaction was diluted with ethylacetate (1 L) and washed with water (2×200 mL), brine (1×200 mL) and dried (MgSO$_4$). After filtration, the filtrate was concentrated to afford 16.5 g of desired product, which was used in the next reaction without further purification.

MS (ES+) 525.28 (M+1).

Step 2: To a stirred solution of product from Step 1 (15 g, 28.62 mmol) in THF (450 mL) was added lithiumdiisopropylamide (57.2 mmol, 114.5 mmol, 2M solution in THF) at −78° C. over a period of 30 min and stirred further at same temperature for 30 min. After quenching the reaction mixture with water (10 mL), it was concentrated and the residue was purified on a column of silica gel using ethyl acetate:hexanes (0 to 20%) as eluent to afford 2.8 g (18.5%) of desired product.

$^1$H NMR (DMSO-$d_6$): δ 7.52 (d, J=0.9 Hz, 1H), 7.38-7.26 (m, 15H), 5.63 (bs, 2H, $D_2O$ exchangeable), 4.83 (d, J=0.9 Hz, 1H), 4.62-4.54 (m, 6H), 4.17 (q, J=4.7 Hz, 1H), 3.89 (d, J=4.9 Hz, 1H), 3.69-3.59 (m, 2H), 1.15 (s, 3H); IR (neat): 3446.8, 3344.5, 3233.6, 3063.0, 3031.6, 2977.6, 2871.3, 2202.3, 1955.7, 1879.2, 1814.9, 1766.3, 1726.9, 1636.1, 1551.5, 1494.8, 1450.5, 1364.0, 1260.6, 1176.7, 1095.2, 1027.6, 912.4, 873.6, 819.6, 787.0, 737.7 and 698.3 cm$^{-1}$; MS (ES+) 547.33 (M+23), (ES−): 523.24 (M−1); Anal. Calcd for $C_{32}H_{32}N_2O_5$: C, 73.26; H, 6.14; N, 5.33. Found: C, 73.67; H, 6.33; N, 4.90.

Step 3: To a stirred solution of compound from Step 2 (2.8 g, 5.34 mmol) in pyridine (100 mL) was added triethylamine (35 mL) and $H_2S$ gas was bubbled for 30 min. The reaction mixture was transferred to a steel bomb and stirred at 60° C. for 16 h. After concentration, the residue was purified on a column of silica gel using ethyl acetate:hexanes as eluent to provide 2.35 g (78.8%) of desired product as a yellow brown solid.

$^1$H NMR (DMSO-$d_6$): δ 8.48 (bs, 1H, $D_2O$ exchangeable), 8.32 (bs, 1H, $D_2O$ exchangeable), 7.43 (s, 1H), 7.37-7.25 (15H), 6.46 (bs, 2H, $D_2O$ exchangeable), 4.89 (s, 1H), 4.65 (m, 6H), 4.17 (dd, J=9.0, 4.3 Hz, 1H), 3.92 (d, J=5.3 Hz, 1H), 3.71 (dd, J=10.7, 4.1 Hz, 1H), 3.65 (dd, J=10.7, 4.3 Hz, 1H), 1.16 (s, 3H); MS (ES+) 559.27 (M+1), 581.23 (M+23).

Step 4: A mixture of product from Step 3 (2.3 g, 4.12 mmol) and triethylorthoformate (100 mL) was heated at 100° C. for 18 h. After concentration, the residue was purified on a column of silica gel using ethyl acetate:hexanes as eluent to afford 1.32 g (56.5%) of desired product along with some unidentified products.

$^1$H NMR (DMSO-$d_6$): δ 14.10 (bs, 1H, $D_2O$ exchangeable), 8.34 (s, 1H), 8.26 (s, 1H), 7.38-7.25 (m, 15H), 5.21 (s, 1H), 4.73-4.52 (m, 6H), 4.20-4.15 (m, 1H), 4.03 (d, J=7.5 Hz, 1H), 3.79-3.66 (m, 2H), 1.20 (s, 3H); MS (ES+) 569.74 (M+1), 591.37 (M+23); Anal. Calcd for $C_{33}H_{32}N_2O_5S$: C, 69.69; H, 5.67; N, 4.92. Found: C, 69.94; H, 5.70; N, 4.88.

Step 5: To a stirred solution of product from Step 4 (0.1 g, 0.176 mmol) in dichloromethane (10 mL) was added $BCl_3$ (1.7 mL, 1.7 mmol, 1M solution in dichloromethane) at −78° C. and further stirred at this temperature for 30 min and at −30° C. for another 30 min. The reaction was quenched by adding water (1.5 mL) and brought to room temperature over a period of 30 min. After neutralization with aqueous $NH_3$ and concentrating, the residue was purified on a column of silica gel using methanol and chloroform (0 to 30%) as eluent to afford 10 mg (19%) of product as a colorless solid.

$^1$H NMR (DMSO-$d_6$): δ 14.00 (bs, 1H, $D_2O$ exchangeable), 8.39 (s, 1H), 8.26, (s, 1H), 5.00 (d, J=4.8 Hz, 1H, $D_2O$ exchangeable), 4.94 (s, 1H), 4.82 (t, J=5.4 Hz, 1H, $D_2O$ exchangeable), 4.75 (s, 1H, $D_2O$ exchangeable), 3.77-3.70 (m, 3H), 3.63-3.54 (m, 1H), 0.92 (s, 3H); MS (ES+) 321.26 (M+1), (ES−) 297.30 (M+35); Anal. Calcd for $C_{12}H_{14}N_2O_5S.0.75H_2O$: C, 46.22; H, 5.01; N, 8.98. Found: C, 46.85; H, 5.24; N, 8.36.

Example B-28

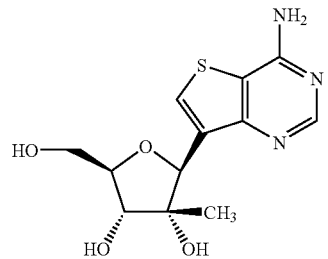

4-Amino-7-β-(2'-C-methyl-D-ribofuranosyl)-thieno[3,2-d]pyrimidine (Scheme B-8)

Step 1: A solution of compound from Example B-24, Step 2 (1.23 g, 2.49 mmol) in dichloromethane (10 mL) at 0° C. was treated with triethylamine (0.44 mL) followed by addition of methyl sulfonyl chloride (343 mg, 3.0 mmol) in dichloromethane (6 mL) over a period of 10 min. The reaction mixture was stirred at 0° C. for 1 h and diluted with chloroform (20 mL) and was washed with brine (2×) and dried over $MgSO_4$. After filtration, the filtrate was concentrated to give desired product (1.43 g) and used as such for next step.

MS (ES+) 594.28 (M+Na)+.

Step 2: A mixture of the product from Step 1 (1.43 g), acetylthioacetonitrile (575 mg, 5.0 mmol), and anhydrous $Na_2CO_3$ (530 mg, 5.0 mmol) in absolute ethanol (30 mL) was refluxed for 6 h and concentrated to dryness. The residue was partitioned between chloroform and water. The organic layer was separated and further washed with water and dried over $MgSO_4$. After filtration, the filtrate was concentrated and the residue was purified on a silica gel column using hexanes:ether (1:0 to 7:3) as eluent to give 140 mg (10% for two steps) of desired product as an oil.

$^1$H NMR (DMSO-$d_6$): δ 7.54-7.47 (m, 4H), 7.35-7.26 (m, 6H), 7.09 (d, J=1.2 Hz, 1H), 5.86 (bs, 2H), 4.53 (s, 1H), 4.30 (d, J=2.3 Hz, 1H), 4.04-3.99 (m, 1H), 3.68 (t, J=4.4 Hz, 2H), 1.40 (s, 3H), 1.20 (s, 3H), 0.85 (bs, 12H); MS (ES+) 571.37 (M+Na)+.

Step 3: A mixture of compound from Step 2 (120 mg, 0.22 mmol) and formamidine acetate (227 mg, 2.16 mmol) in EtOH (5 mL) was refluxed for 16 h. Additional formamidine acetate (227 mg, 2.16 mmol) was added followed by reflux for 16 h. After concentration, the residue was taken in chloroform and washed with water and dried over $MgSO_4$. After filtration, the filtrate was concentrated and the residue was purified on a silica gel column using hexanes:ether (1:0 to 1:1) as eluent to give 11 mg (9%) of desired product as an oil.

$^1$H NMR ($CDCl_3$): δ 8.65 (s, 1H), 7.80-7.70 (m, 4H), 7.64 (d, J=1.2 Hz, 1H), 7.50-7.36 (m, 6H), 5.56 (s, 1H), 5.38 (bs, 2H), 4.51 (d, J=3.1 Hz, 1H), 4.25 (dd, J=7.2, 3.8 Hz, 1H), 4.00-3.92 (m, 2H), 1.75 (s, 3H), 1.45 (s, 3H), 1.12 (s, 3H), 1.10 (s, 9H); MS (ES+) 576.49 (M+H)+.

Step 4: A solution of compound from Step 3 (28 mg, 0.049 mmol) in 12% dry HCl/MeOH (2 mL) was stirred at room temperature for 0.5 h followed by concentration. The residue was treated with 12% dry HCl/MeOH (2 mL) again and stirred at room temperature for 15 min followed by concentration. This process was repeated once more with 1 mL of dry 12% HCl/MeOH. The residue was washed with ether (2×) and dried under vacuum to afford 16 mg (88%) of desired product as hydrochloride.

$^1$H NMR (D$_2$O): δ 8.45 (s, 1H), 8.18 (s, 1H), 5.14 (s, 1H), 3.98-3.75 (m, 4H), 0.80 (s, 3H); MS (ES$^+$) 298.41 (M+H)$^+$.

Example B-29

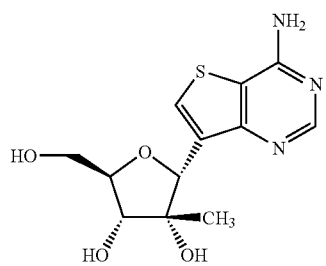

4-Amino-7-α-(2'-C-methyl-D-ribofuranosyl)-thieno [3,2-d]pyrimidine (Scheme B-8)

Step 1: Under Example B-28 in Step 2, another product alpha isomer was also isolated.

$^1$H NMR (DMSO-d$_6$): δ 7.49-7.42 (m, 4H), 7.34-7.20 (m, 7H), 5.99 (s, 2H), 4.61 (s, 1H), 4.25 (s, 1H), 3.92 (t, J=6.8 Hz, 1H), 3.59-3.53 (m, 2H), 1.19 (s, 3H), 1.15 (s, 3H), 1.12 (s, 3H), 0.83 (s, 9H); IR (neat, cm$^{-1}$) 3473, 3359, 2932, 2858, 2198, 1428, 1109; Anal. Calcd for C$_{30}$H$_{36}$N$_2$O$_4$Si: C, 65.66; H, 6.61; N, 5.10. Found: C, 65.42; H, 6.68; N, 4.94; MS (ES): 571.49 (M+Na)$^+$.

Step 2: A mixture of compound from Step 1 (230 mg, 0.42 mmol) and formamidine acetate (437 mg, 4.20 mmol) in EtOH (6 mL) was refluxed for 6 h. Additional formamidine acetate (437 mg, mmol) was added followed by reflux for 18 h. The reaction mixture was concentrated and the residue was taken in chloroform, washed with water, and dried over MgSO$_4$. After filtration, the filtrate was concentrated and the residue was purified on a silica gel column using hexanes:EtOAc (1:0 to 1:1) as eluent to give 195 mg (81%) of desired product as an oil.

$^1$H NMR (DMSO-d$_6$): 8.40 (s, 1H), δ 7.99 (s, 1H), 7.78-7.41 (m, 10H), 5.43 (s, 1H), 4.63 (s, 1H), 4.24 (t, J=5.5 Hz, 1H), 3.86 (d, J=5.3 Hz, 2H), 1.55 (s, 3H), 1.43 (s, 3H), 1.33 (s, 3H), 1.09 (s, 9H); IR (neat, cm$^{-1}$) 3450, 3337, 2932, 2858, 1636, 1573, 1513, 1109; MS (ES$^+$) 598.40 (M+Na)$^+$; Anal. Calcd for C$_{31}$H$_{37}$N$_3$O$_4$SSi·H$_2$O: C, 62.70; H, 6.62; N, 7.08. Found: C, 62.40; H, 6.37; N, 6.99.

Step 3: Compound from Step 2 (90 mg, 0.16 mmol) was treated the same way as Step 4 in Example B-28. It gave 43 mg (74%) of desired product as hydrochloride.

$^1$H NMR (MeOH-d$_4$): δ 9.54 (bs, 2H), 8.74 (s, 2H), 8.43 (s, 1H), 5.13 (s, 1H), 4.27-4.17 (m, 1H), 4.00 (d, J=8.0 Hz, 1H), 3.76-3.52 (m, 2H), 1.16 (s, 3H); IR (KBr, cm$^{-1}$) 3367, 1661, 1607, 1568, 1036; MS (ES$^+$) 298.41 (M+H)$^+$; Anal. Calcd for C$_{12}$H$_{15}$N$_3$O$_4$S·HCl·1.5H$_2$O: C, 39.95; H, 5.31; N, 11.65. Found: C, 40.48; H, 5.37; N, 11.24.

Example B-30

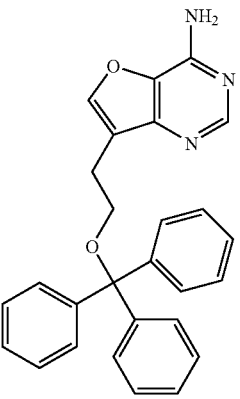

7-(2-(Trityloxy)ethyl)furo[3,2-d]pyrimidin-4-amine (Scheme B-6)

It was prepared by following the method (alternate approach, Steps 1-5) used for compound B-24 starting from Example A-1.

$^1$H NMR (DMSO-d$_6$): δ 8.18 (s, 1H), 8.02 (s, 1H), 7.32-7.22 (m, 15H), 3.25 (t, J=6.6 Hz, 2H), 2.87 (t, J=6.6 Hz, 2H).

Example B-31

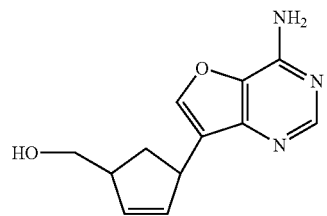

(cis)(4-(4-Aminofuro[3,2-d]pyrimidin-7-yl)cyclopent-2-enyl)methanol (Scheme B-6)

It was prepared by following the method used for compound B-24 starting from Example A-9.

$^1$H NMR (CDCl$_3$): δ 8.42 (s, 1H), 7.58 (s, 1H), 5.89 (td, J=5.4, 2.3 Hz, 1H), 5.76 (td, J=5.4, 2.3 Hz, 1H), 5.22 (bs, 2H, D$_2$O exchangeable), 4.54 (bs, 1H, D$_2$O exchangeable), 4.18-4.10 (m, 1H), 3.88 (dd, J=10.9, 3.7 Hz, 1H), 3.76 (dd, J=10.7, 3.0 Hz, 1H), 3.22-3.13 (m, 1H), 2.64 (td, J=13.9, 9.7 Hz, 1H), 2.07 (td, J=13.9, 6.4 Hz, 1H); MS (ES$^+$) 254.52 (M+23).

Example B-32

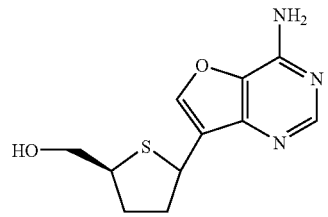

(5-(4-Aminofuro[3,2-d]pyrimidin-7-yl)-tetrahydrothiophen-2-yl)methanol (Scheme B-6)

It was prepared by following the method used for compound B-24 starting from Example A-10.

$^1$H NMR (CD$_3$OD): δ 8.58 (s, 1H), 8.32 (s, 1H), 4.70 (t, J=6.4 Hz, 1H), 3.85 (t, J=6.5 Hz, 1H), 3.65 (m, 2H), 2.50 (m, 1H), 2.20 (m, 2H), 1.95 (m, 1H); MS (ES$^+$) 252.53 (M+H)$^+$.

Example B-33

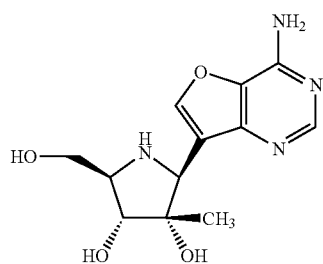

2-(4-Aminofuro[3,2-d]pyrimidin-7-yl)-5-(hydroxymethyl)-3-methylpyrrolidine-3,4-diol (Scheme B-6)

It was prepared by following the method used for compound B-24 starting from Example A-11.

$^1$H NMR (D$_2$O): 8.58 (s, 1H), 8.53 (s, 1H), 5.05 (s, 1H), 4.51 (d, J=9.2 Hz, 1H), 4.10-4.12 (m, 2H), 3.80-3.90 (m, 1H), 1.17 (s, 3H); $^{13}$C NMR (D$_2$O): 152.16, 148.59, 147.63, 143.90, 133.77, 113.80, 78.89, 73.45, 63.16, 60.67, 57.82, 19.51; MS (ES$^+$) 281.41.

Example B-34

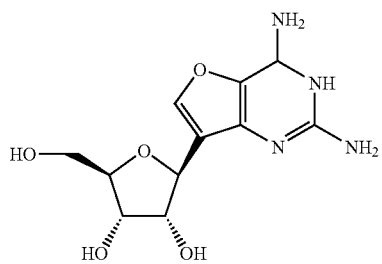

2-Amino-7-β-(1)-ribofuranosyl)-furo[3,2-d]pyrimidin-4(3H)-one (Scheme B-4)

It was prepared from Example A-2 by following the same procedure used for Example B-21.

$^1$H NMR (DMSO-d$_6$): δ 8.11 (s, 1H), 4.69 (d, J=6.9 Hz, 1H), 4.05-4.01 (m, 1H), 3.97-3.95 (m, 1H), 3.89-3.86 (m, 1H), 3.80-3.63 (m, 2H); MS (ES$^-$) 282.34 (M−1). Anal. Calcd for C$_{11}$H$_{13}$N$_3$O$_5$.2HCl.1.5H$_2$O: C, 34.55; H, 4.75; N, 10.99. Found: C, 34.37; H, 4.98; N, 10.87.

Example B-35

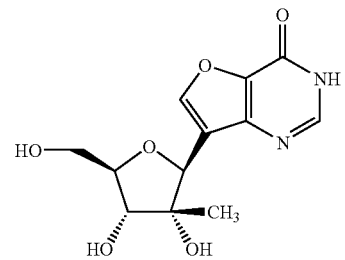

7-β-(2'-C-Methyl-D-ribofuranosyl)-furo[3,2-d]pyrimidin-4(3H)-one (Scheme B-1)

It was prepared by deprotection of Example B-11 by hydrogenation under the same conditions used with Example B-16.

$^1$H NMR (DMSO-d$_6$): δ 12.42 (bs, 1H, D$_2$O exchangeable), 8.20 (s, 1H), 8.08 (s, 1H), 4.98 (d, J=6.4 Hz, 1H), 4.93 (s, 1H), 4.83 (t, J=5.0 Hz, 1H, D$_2$O exchangeable), 4.73 (s, 1H, D$_2$O exchangeable), 3.78-3.70 (m, 2H), 3.64-3.54 (m, 1H), 0.93 (s, 3H); MS (ES$^-$) 281.34 (M−1); Anal. Calcd for C$_{12}$H$_{14}$N$_2$O$_6$.CH$_4$O: C, 49.66; H, 5.77; N, 8.91. Found: C, 49.63; H, 5.61; N, 8.26.

Example C-1

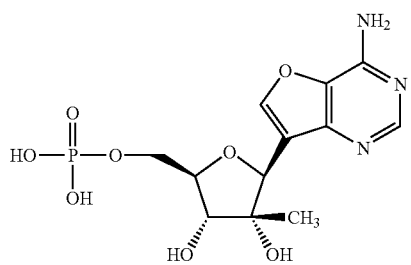

4-Amino-7-β-(2'-C-methyl-D-ribofuranosyl)-furo[3,2-d]pyrimidine-5'-monophosphate (Scheme C-1)

Step 1: A solution of Example B-24 (50 mg, 0.18 mmol) in THF (6 mL) was treated with 1-H-tetrazole (39 mg, 98%, 0.55 mmol) and cooled with ice/water followed by dropwise addition of dibenzyl N,N-diisopropylphosphoramidite (75 μL, 0.22 mmol). The reaction mixture was stirred at 0° C. for 1 h and at room temperature for 2 h. Additional dibenzyl N,N-diisopropylphosphoramidite (25 μL, 0.075 mmol) was added and the mixture was stirred at room temperature further for 1 h. The reaction mixture was cooled to −40° C., and treated with m-CPBA (82 mg, max. 77%) followed by stirring at 0° C. for 2 h. After diluting with chloroform (100 mL), the mixture was washed with 5% Na$_2$SO$_3$ (2×30 mL), sat. NaHCO$_3$ (2×30 mL) and water (2×30 mL), and dried over MgSO$_4$. After filtration, the filtrate was concentrated and the residue was purified on a silica gel column using chloroform/MeOH (1:0 to 10:1) as eluent to give 40 mg (41%) of desired product as a white solid.

¹H NMR (DMSO-d₆): δ 8.22 (s, 1H), 8.10 (s, 1H), 7.39 (bs, 2H), 7.36-7.27 (m, 10H), 5.23 (d, J=6.4 Hz, 1H), 5.02 (s, 2H), 5.00 (s, 2H), 4.99 (s, 1H), 4.91 (s, 1H), 4.34-4.26 (m, 2H), 4.12-3.96 (m, 2H), 0.92 (s, 3H); MS (ES⁺) 542.31 (M+H)⁺.

Step 2: A mixture of product from Step 1 (35 mg, 0.065 mmol) and Pd—C (10%, 20 mg) in MeOH (15 mL) was hydrogenated for 16 h (~50 psi). After-removing the catalyst by filtration, the filtrate was concentrated and the residue was treated with water (10 mL) and washed with EtOAc (2×10 mL) and chloroform (2×10 mL). The aqueous phase was concentrated to dryness. The residue was dissolved in 2 mL of H₂O and filtered, which gave a 24.4 mM (measured by UV at 274 nM) solution of desired monophosphate.

¹H NMR (D₂O): δ 8.13 (bs, 1H), 8.03 (s, 1H), 5.03 (s, 1H), 4.20-4.08 (m, 1H), 4.06-3.85 (m, 3H), 0.88 (s, 3H); ³¹P NMR (D₂O): δ 0.83 (bs, 1P); MS (ES⁺) 362.42 (M+H)⁺.

Example C-2

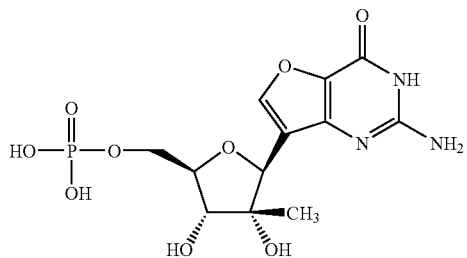

2-Amino-7-β-(2'-C-methyl-D-ribofuranosyl)-furo[3,2-d]pyrimidin 4(3H)-one-5'-monophosphate
(Scheme C-1)

Step 1: A mixture of Example B-21 (48 mg, 0.15 mmol), 2,2-dimethoxypropane (0.34 mL, 98%, 2.72 mmol), and p-toluenesulfonic acid monohydrate (40 mg, 0.21 mmol) in acetone (2 mL) and DMF (2 mL) was stirred at room temperature of 2 h followed by neutralization with 0.5 N aqueous NaOH. The mixture was concentrated to dryness and used as such for the next step.
MS (ES⁺) 338.37 (M+H)⁺.

Step 2: The product from Step 1 was mixed with imidazole (60 mg, 0.88 mmol) and TBDMSCl (45 mg, 0.30 mmol) in DMF (3 mL) and stirred at room temperature for 8 h. Additional imidazole (120 mg) and TBDMSCl (90 mg) were added and the reaction mixture was further stirred at room temperature for 17 h followed by concentration to dryness. The residue was purified on a silica gel column using chloroform/MeOH (1:0 to 95:5) as eluent to give 50 mg (74% for two steps) of desired product as a colorless film.

¹H NMR (MeOH-d₄): δ 7.58 (d, J=1.0 Hz, 1H), 4.91 (s, 1H), 4.29 (d, J=2.9 Hz, 1H), 4.02-3.95 (m, 1H), 3.78-3.66 (m, 2H), 1.49 (s, 3H), 1.28 (s, 3H), 1.11 (s, 3H), 0.81 (s, 9H), 0.00 (s, 6H); MS (ES⁺) 452.44 (M+H)⁺.

Step 3: A mixture of compound from Step 2 (50 mg, 0.11 mmol) and 4-methoxytrityl chloride (70 mg, 0.22 mmol) in pyridine (3 mL) was stirred at 70° C. for 13 h. The reaction mixture was diluted with EtOAc (100 mL) and washed with water (2×50 mL), brine (50 mL), and dried over MgSO₄. After filtration, the filtrate was concentrated and the residue was purified on a silica gel column using hexanes/EtOAc (1:0 to 1:1) as eluent to give 45 mg (57%) of desired product as a colorless film.

¹H NMR (CDCl₃): δ 9.91 (bs, 1H), 7.36-7.00 (m, 13H), 6.90 (bs, 1H), 6.68 (d, J=8.8 Hz, 2H), 4.72 (s, 1H), 4.23 (d, J=3.2 Hz, 1H), 4.00-3.94 (m, 1H), 3.68 (d, J=4.0 Hz, 2H), 3.66 (s, 3H), 1.38 (s, 3H), 1.28 (s, 3H), 0.99 (s, 3H), 0.82 (s, 9H), 0.00 (s, 6H);
MS (ES⁺) 746.31 (M+Na)⁺.

Step 4: A solution of product from Step 3 (45 mg, 0.062 mmol) in THF (3 mL) was treated with Bu₄NF (1M in THF, 0.12 mL) followed by stirring at room temperature for 2.5 h. The reaction mixture was concentrated and the residue was purified on a silica gel column using hexanes/EtOAc/MeOH (1:1:0 to 1:1:0.1) as eluent to give 39 mg (100%) of desired product as a colorless film.

¹H NMR (CDCl₃): δ 7.77 (bs, 1H), 7.60 (s, 1H), 7.40-7.20 (m, 12H), 6.87 (d, J=8.9 Hz, 2H), 6.30 (s, 1H), 5.17 (s, 1H), 4.64 (d, J=1.4 Hz, 1H), 4.34 (bs, 1H), 4.03-3.68 (m, 2H), 3.80 (s, 3H), 1.60 (s, 3H), 1.41 (s, 3H), 1.36 (s, 3H); (MS (ES⁺) 632.28 (M+Na)⁺.

Step 5: A solution of product from Step 4 (39 mg, 0.62 mmol) in dichloromethane (2 mL) was treated with 1-H-tetrazole (14 mg, 98%, 0.20 mmol) and the suspension was stirred at room temperature for 5 min followed by addition of dibenzyl N,N-diisopropylphosphoramidite (35 μL, 0.1 mmol). The reaction mixture was stirred at room temperature for 3.5 h, cooled to −40° C., and treated with a solution of m-CPBA (30 mg, max. 77%) in dichloromethane (1 mL) followed by stirring at 0° C. for 2 h. The reaction mixture was diluted with chloroform (50 mL) and washed with 5% Na₂SO₃ (2×15 mL), NaHCO₃ (2×15 mL), water (2×20 mL), and dried over MgSO₄. After filtration, the filtrate was concentrated, and the residue was purified on a silica gel column using hexanes/EtOAc/MeOH (1:1:0 to 1:1:0.1) as eluent to give 38 mg (70% for two steps) of desired product as a white solid.

¹H NMR (DMSO-d₆): δ 10.88 (s, 1H), 7.69 (s, 1H), 7.44-7.10 (m, 23H), 6.81 (d, J=8.8 Hz, 2H), 5.06 (s, 2H), 5.03 (s, 2H), 4.51 (s, 1H), 4.12 (d, J=2.3 Hz, 1H), 4.05-3.95 (m, 3H), 3.69 (s, 3H), 1.24 (s, 3H), 1.23 (s, 3H), 0.81 (s, 3H); IR (KBr, cm⁻¹) 3339, 2984, 1699, 1611, 1252, 1017; MS (ES⁺) 870.30 (M+H)⁺; Anal. Calcd for C₄₉H₁₈N₃O₁₀P.0.75H₂O: C, 66.62; H, 5.65; N, 4.76. Found: C, 66.68; H, 5.64; N, 4.80.

Step 6: A mixture of product from Step 5 (30 mg, 0.034 mmol) and Pd—C (10%, 20 mg) in MeOH (15 mL) was hydrogenated for 20 h (~50 psi). After removing the catalyst by filtration, the filtrate was concentrated, and the residue was treated with TFA (3 mL) and stirred at room temperature for 1 h followed by concentration to dryness. The residue was stirred with EtOAc (20 mL), water (20 mL), and TEAB (pH=8.0, 1M, 2 mL) for 30 min. The organic layer was collected, the aqueous phase was further extracted with EtOAc (2×20 mL) and the combined organic extracts were concentrated to dryness. The residue was treated with MeOH (6 mL) and 20% dry HCl in MeOH (7.5 mL) followed by stirring at room temperature for 1.2 h. The reaction mixture was concentrated to dryness and purified by HPLC (CH₃CN/1M TEAB buffer, pH=8.0, 0-20 min, 0-35% CH₃CN; 20-22 min, 35-60% CH₃CN, monitoring at 260 nm) to give the desired product (t_R=14.1 min). All the fractions containing product were pooled together and reconstituted to 2 mL with water, which gave 6.1 mM (measured by UV at 288 nm)-solution of desired monophosphate.

¹H NMR (D₂O): δ 7.78 (d, J=0.7 Hz, 1H), 4.91 (d, J=0.6 Hz, 1H), 4.15-4.07 (m, 1H), 4.04-3.86 (m, 3H), 0.95 (s, 3H); ³¹P NMR (D₂O): 1.81 (s, 1P); MS (ES⁺) 378.30 (M+H)⁺.

Example C-3

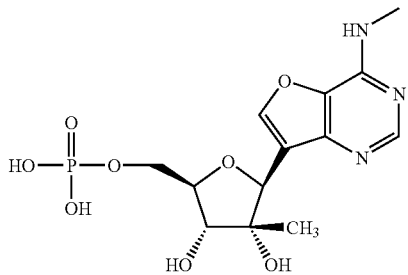

4-Methylamino-7-β-(2'-C-methyl-D-ribofuranosyl)-furo[3,2-d]pyrimidine-5'-monophosphate (Scheme C-1)

A solution of Example B-17 (50 mg, 0.17 mmol) in THF (5 mL) was cooled to 0° C. and to this were added, tetrazole (0.51 mmol, 35 mg) and dibenzyl diisopropylphosphoramidate (0.17 mmol, 61 μL) and the mixture was stirred for 1 h. Additional 0.2 equivalents of the phosphorylating reagents were added and stirring continued for 2 h at room temperature. The reaction was then cooled to −40° C. and m-chloroperbenzoic acid (80 mg, 0.34 mmol) was added and the reaction was allowed to warm to room temperature. The reaction was quenched by the addition of 10% aqueous sodium sulfite (3 mL), and diluted with CHCl$_3$ (20 mL). The organic layer was washed with water (20 mL), aqueous saturated sodium bicarbonate solution (2×20 mL), and dried over MgSO$_4$. After filtration, the filtrate was concentrated and the residue was purified on a silica gel column using 0 to 5% MeOH in chloroform as eluent to give 70 mg of desired product. This product was dissolved in MeOH (10 mL) and to the solution was added 10% Pd—C (50 mg). The suspension was hydrogenated for 18 h at 50 psi, the catalyst was removed by filtration through Celite and the residue was taken in water and ethyl acetate (20 mL each). The organic layer was removed, and the aqueous layer was concentrated and purified by HPLC (gradient 0 to 100% CH$_3$CN in water on reverse phase C18 column, $t_R$-7.8 min). The desired fractions were collected and concentrated to give 46 mg (70%) of desired phosphate.

$^1$H NMR (D$_2$O δ in ppm) 8.05 (s, 1H), 8.04 (s, 1H), 5.20 (s, 1H), 3.90 (m, 4H), 2.90 (s, 3H), 0.90 (s, 3H). $^{31}$P NMR 4.7 ppm. MS (ES$^+$) 376 (M+H)$^+$, 398 (M+Na)$^+$, MS (ES$^-$) 374.30 (M−H)$^-$.

Example C-4

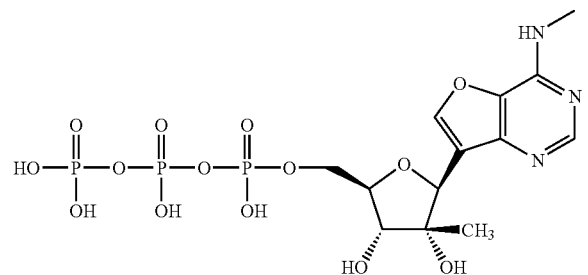

4-Methylamino-7-β-(2'-C-methyl-D-ribofuranosyl)-furo[3,2-d]pyrimidine-5'-triphosphate (Scheme C-2)

Step 1: A mixture of Example B-17 (95 mg, 0.32 mmol), MMTrCl (550 mg, 98%, 1.75 mmol), DMAP (25 mg, 0.20 mmol), and pyridine (3.2 mL) in DMF (2 mL) was stirred at room temperature for 19 h followed by addition of triethylamine (2.4 mL, 17.22 mmol), DMAP (20 mg, 0.16 mmol), and 4-nitrobenzoyl chloride (1.22 g, 98%, 6.44 mmol) and stirred at room temperature for five days. The reaction mixture was diluted with ethyl acetate (100 mL), washed with water (2×50 mL), brine (50 mL), and dried over MgSO$_4$. After filtration, the filtrate was concentrated and the residue was purified on a silica gel column using hexanes/EtOAc (1:0 to 1:1) as eluent to give 110 mg (34%) of desired product as a brown syrup.

$^1$H NMR (CDCl$_3$): δ 8.88 (s, 1H), 7.89 (s, 1H), 8.51-7.20 (m, 24H), 6.85 (d, J=9.0 Hz, 2H), 5.95 (d, J=4.0 Hz, 1H), 5.65 (J=0.8 Hz, 1H), 4.27 (dd, J=8.0, 4.2 Hz, 1H), 3.80 (s, 3H), 3.76 (s, 3H), 3.66-3.62 (m, 2H), 1.48 (s, 3H).

Step 2: A solution of product from Step 1 (105 mg, 0.1 mmol) in acetonitrile (10 mL) was treated with 0.2 N aqueous HCl (0.5 mL) and stirred at room temperature for 2 h. The reaction mixture was neutralized with 0.5 N aqueous NaOH to pH=5 followed by dilution with water (20 mL) and concentration to remove most of acetonitrile. The aqueous mixture was extracted with chloroform (2×50 mL) and EtOAc (2×25 mL). The combined organic extracts were dried over MgSO$_4$. After filtration, the filtrate was concentrated and the residue was purified on a silica gel column using hexanes/EtOAc/MeOH (1:0:0 to 1:1:0.1) as eluent to give 600 mg (81%) of desired product as a yellow solid.

$^1$H NMR (DMSO-d$_6$): δ 9.13 (s, 1H), 8.46 (d, J=0.8 Hz, 1H), 8.41-7.66 (m, 12H), 5.72 (d, J=3.2 Hz, 1H), 5.60 (s, 1H), 5.18 (t, J=6.0 Hz, 1H), 4.25 (dd, J=6.8, 3.6 Hz, 1H), 3.85-3.79 (m, 2H), 3.66 (s, 3H), 1.37 (s, 3H); MS (ES$^+$): 743.26 (M+H)$^+$.

Step 3: A suspension of product from Step 2 (50 mg, 0.067 mmol) in a mixture of pyridine (75 μL) and dioxane (220 μL) was treated with a freshly prepared solution of chloro-4H-1,3,2-benzodioxaphosphorin-4-one (1M in dioxane, 80 μL) and was stirred at room temperature for 20 min followed by treatment with a solution of tributylammonium pyrophosphate (1.6 Bu$_3$N.1.0 H$_4$P$_2$O$_7$, 51 mg, 0.11 mmol) in DMF (220 μL) and n-butylamine (70 μL) simultaneously. A clear solution formed which was stirred at room temperature for 30 min and treated with 2.8 mL of 1% I$_2$ in Py/H$_2$O (98/2). Excess iodine was reduced by addition of 5% aqueous sodium thiosulphate (230 μL) and the resulting solution was concentrated to dryness. The residue was treated with conc. NH$_4$OH (20 mL) and was stirred at room temperature overnight followed by concentration to dryness. The residue was dissolved in H$_2$O (20 mL) and washed with CH$_2$Cl$_2$ (2×15 mL). The aqueous phase was concentrated under vacuum for a short period of time to remove the trace of CH$_2$Cl$_2$ and purified by DEAE ion exchange column chromatography with a linear gradient of TEAB buffer (1M TEAB buffer, pH=8.0/H$_2$O, 250 mL/250 mL, 0:1 to 1:0). The fractions containing the desired nucleotide were combined and concentrated. The residue was redissolved in H$_2$O and purified further by HPLC (CH$_3$CN/0.1M TEAB buffer, pH=8.0, 0-20 min, 0-35% CH$_3$CN; 20-28 min, 35-100% CH$_3$CN, monitoring at 260 nm) to give the product ($t_R$=15.6 min). The desired fractions were pooled together and re-dissolved in 2 mL of water to give 3.3 mM (measured by UV at 278 nm) solution of desired triphosphate.

$^1$H NMR (D$_2$O): δ 8.17 (s, 1H), 8.04 (s, 1H), 5.11 (s, 1H), 4.30-4.10 (m, 2H), 4.02 (s, 2H), 2.95 (s, 3H), 0.98 (s, 3H); $^{31}$P NMR (D$_2$O): δ −8.20 (d, J=17.8 Hz, 1P), −9.86 (d, J=17.3, 1P), −21.50 (t, J=17.9 Hz, 1P); MS (ES$^-$) 534.14 (M−1).

Example C-5

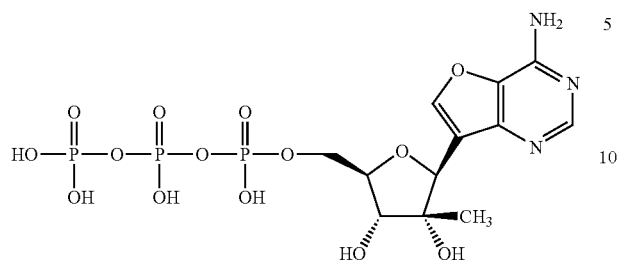

4-Amino-7-β-(2'-C-methyl-D-ribofuranosyl)-furo[3,2-d]pyrimidine-5'-triphosphate (Scheme C-2)

Step 1: A mixture of Example B-24 (138 mg, 0.49 mmol) and imidazole (175 mg, 2.57 mmol) in DMF (5 mL) was treated with TBDMSCl (130 mg, 0.86 mmol) followed by stirring at room temperature for 17 h. To this mixture were added triethylamine (3.2 mL), DMAP (30 mg, 0.25 mmol), 4-nitrobenzoyl chloride (1.66 g, 98%, 8.76 mmol), and DMF (3 mL) and stirring was continued for another 24 h. The reaction mixture was diluted with EtOAc (150 mL), washed with water (2×75 mL), brine (75 mL), and dried over $MgSO_4$. After filtration, the filtrate was concentrated and the residue was purified by column chromatography on a silica gel column using hexanes/ethyl acetate (1:0 to 1:1) as eluent to give 266 mg of product, which was used as such for next step.
MS (ES$^-$) 841.47 (M−1).

Step 2: A solution of compound from Step 1 (260 mg) in THF (25 mL) was treated with tetrabutyl ammonium fluoride (1M in THF, 0.4 mL). The reaction mixture was stirred at room temperature for 2 h and additional tetrabutyl ammonium fluoride (1 mL) was added followed by stirring at room temperature for 5 h and concentration. The residue was purified by column chromatography on silica gel (hexanes/ethyl acetate/methanol, 1:1:0 to 1:1:0.1) to give 40 mg (11% for two steps) of desired product.
$^1$H NMR (DMSO-$d_6$): δ 11.96 (s, 1H), 9.25 (s, 1H), 8.60 (s, 1H), 8.50-8.17 (m, 12H), 5.78 (d, J=3.3 Hz, 1H), 5.71 (s, 1H), 4.30 (m, 1H), 3.89-3.83 (m, 2H), 1.52 (s, 3H); MS (ES$^-$) 727.58 (M−1).

Step 3: A suspension of product from Step 2 (37 mg, 0.051 mmol) in a mixture of pyridine (55 µL) and dioxane (165 µL) was treated with a freshly prepared solution of chloro-4H-1,3,2-benzodioxaphosphorin-4-one (1M in dioxane, 60 µL). The reaction mixture was stirred at room temperature for 20 min followed by treatment with a solution of tributylammonium pyrophosphate (1.6 Bu$_3$N.1.0H$_4$P$_2$O$_7$, 39 mg, 0.082 mmol) in DMF (165 µL) and n-butylamine (55 µL) simultaneously. A clear solution formed which was stirred at room temperature for 30 min followed by treatment with 2.1 mL of 1% I$_{2-}$ in Py/H$_2$O (98/2). Excess iodine was reduced by addition of 5% aqueous sodium thiosulphate (175 µL) and the resulting solution was concentrated to dryness. The residue was treated with conc. NH$_4$OH (15 mL) and was stirred at room temperature overnight followed by concentration to dryness. The residue was dissolved in H$_2$O (20 mL) and washed with CH$_2$Cl$_2$ (2×15 mL). The aqueous phase was concentrated under vacuum for a short period of time to remove the trace of CH$_2$Cl$_2$ and purified by DEAE ion exchange column chromatography with a linear gradient of TEAB buffer (1M TEAB buffer, pH=8.0/H$_2$O, 0:1 to 1:0). The fractions containing the desired nucleotide were combined and concentrated and the residue was redissolved in H$_2$O and purified further by HPLC (CH$_3$CN/0.1M TEAB buffer, pH=8.0, 0-20 min, 0-35% CH$_3$CN; 20-28 min, 35-100% CH$_3$CN, monitoring at 260 nm) to give desired triphosphate (t$_R$=14.7 min). The fractions containing desired product were pooled together, concentrated and re-dissolved in 2 mL of water to give 1.38 mM (measured by UV at 274 nM) solution of triphosphate.
$^1$H NMR (D$_2$O): δ 8.15 (s, 1H), 8.09 (s, 1H), 5.12 (s, 1H), 4.29-4.10 (m, 2H), 4.02 (bs, 2H), 0.97 (s, 3H); $^{31}$P NMR (D$_2$O): δ −8.50 (d, J=15.8 Hz, 1P), −9.88 (d, J=16.8, 4.5 Hz, 1P), −21.5 (dd, J=15.8, 16.8 Hz, 1P); MS (ES$^-$) 520.53 (M−1).

Example C-6

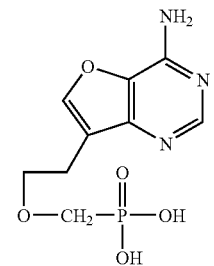

(2-(4-Aminofuro[3,2-d]pyrimidin-7-yl)ethoxy)methylphosphonic acid (Scheme C-3)

Step 1: To a stirred solution of compound from Example B-30, 7-(2-trityloxyethyl)-furo[3,2-d]pyrimidin-4-ylamine (0.52 g, 1.23 mmol) in pyridine (20 mL) was added triphenylchloromethane (0.68 g, 2.46 mmol) at room temperature and the mixture was stirred at 70° C. for 16 h. Additional triphenylchloromethane (6.8 g, 24.6 mmol) was added and again stirred at 70° C. for 48 h. To the reaction mixture was added MeOH (50 mL) and stirred for 1 h at 70° C. The reaction mixture was concentrated and the residue was dissolved in chloroform (100 mL), washed with water (2×50 mL), brine (50 mL), and dried (MgSO$_4$). After filtration, the filtrate was concentrated and the residue was purified on a silica gel column using ethyl acetate in hexanes (0 to 50%), which afforded 0.788 g (96.5%) of desired trityl-[7-(2-trityloxyethyl)-furo[3,2-d]pyrimidin-4-yl]-amine, as a colorless solid.
$^1$H NMR (DMSO-$d_6$): δ 8.20 (s, 1H, D$_2$O exchangeable), 8.09 (s, 1H), 7.88 (s, 1H), 7.70-7.14 (m, 30H), 3.22 (t, J=6.6 Hz, 2H), 5.87 (t, J=6.4 Hz, 2H); MS (ES$^+$) 664.64 (M+1).

Step 2: A solution of compound from Step 1 (753 mg, 1.13 mmol) in acetonitrile (130 mL) was treated with aqueous 0.2 N HCl (6.5 mL, 1.3 mmol) followed by stirring at room temperature for 8 h. The reaction mixture was neutralized with aqueous 0.5 N NaOH, diluted with 150 mL of water, and concentrated under vacuum to remove most of the acetonitrile. The aqueous residue was extracted with chloroform (200 mL) and ethyl acetate (200 mL, 100 mL). The combined organic extracts were dried over MgSO$_4$. After filtration and concentration, the residue was purified on a silica gel column using hexanes:ethyl acetate:methanol (1:1:0 to 1:1:0.1) as eluent to give 394 mg (83%) of desired product as a white solid.

¹H NMR (DMSO-d₆): δ 8.18 (s, 1H), 8.04 (s, 1H), 7.95 (s, 1H), 7.40-7.14 (m, 15H), 4.80 (t, J=5.5 Hz, 1H), 3.72-3.62 (m, 2H), 2.72 (t, J=6.8 Hz, 2H); MS (ES⁺) 422.43 (M+H)⁺.

Step 3: A solution of product from Step 2 (345 mg, 0.82 mmol) in DMF (7 mL) was treated with sodium hydride (60%, 132 mg, 3.3 mmol) at room temperature and the mixture was stirred for 1 h. To this solution was added a solution of (di-isopropoxyphosphono)methyl tosylate (345 mg, 0.98 mmol) in DMF (1 mL) and the mixture was stirred at room temperature for 18 h. The reaction mixture was diluted with ethyl acetate (100 mL), neutralized with acetic acid and washed with water (2×) and brine and the organic layer was dried over MgSO₄. After filtration, the filtrate was concentrated and the residue was purified on a silica gel column using ethyl acetate:hexanes:methanol (1:1:0 to 1:1:0.1), then CMA-80 as eluents to give 160 mg (33%) of desired product as a colorless film.

MS (ES⁺) 622.43 (M+Na)⁺.

Another compound with loss of one isopropyl group, 170 mg (37%) was isolated as a white solid.

MS (ES⁺) 558.43 (M+H)⁺.

The mixture of both compounds was used for the next step.

Step 4: A solution of products from Step 3, (139 mg, 0.23 mmol) and (142 mg, 0.25 mmol), in DMF (4.8 mL) was treated with triethylamine (0.42 mL) followed by trimethylsilyliodide (0.69 mL, 4.83 mmol) and the reaction mixture flask was covered with aluminum foil to protect from light and stirred for 24 h at room temperature. It was then diluted with TEAB buffer (13 mL), water (50 mL) and chloroform (85 mL) and stirred for 1 h. The organic phase was collected and the aqueous phase was re-extracted with chloroform (3×50 mL). The combined organic extracts were dried over MgSO₄. After filtration, the filtrate was concentrated and the residue was used as such for next step. MS (ES⁺) 516.40 (M+H)⁺.

Step 5: A solution of compound from Step 4 in MeOH (21 mL) was treated with conc. HCl (21 mL) and stirred at room temperature for 20 h. The reaction mixture was concentrated to dryness and treated with 10 mL of water followed by extraction with ethyl acetate (2×10 mL). The aqueous layer was concentrated to about 5 mL, filtered (0.2 μm), and purified by HPLC (CH₃CN/0.1 M TEAB buffer, pH=8.0, 0-20 min, 0-35% CH₃CN; 20-28 min, 35-100% CH₃CN, monitoring at 260 nm) to give the desired product ($t_R$=14.74 min). Fractions containing the desired product were pooled together, concentrated and re-dissolved in 2 mL of H₂O and give 10.48 mM (measured by UV at 274 nm) solution of the monophosphate.

¹H NMR (H₂O-d₂): δ 8.10 (s, 1H), 7.78 (s, 1H), 3.74 (t, J=6.2 Hz, 2H), 3.53 (d, J=8.5 Hz, 2H), 2.79 (t, J=6.2 Hz, 2H); ³¹P NMR (H₂O-d₂): 17.02 (bs, 1P); MS (ES⁺): 274.46 (M+H)⁺.

Example D-1

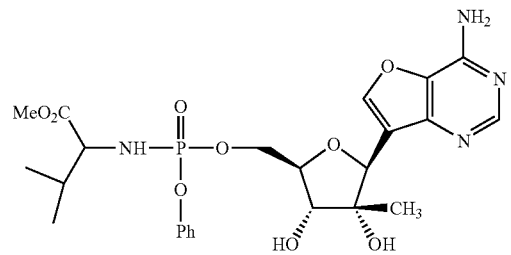

Methyl 2-(((5-(4-aminofuro[3,2-d]pyrimidin-7-yl)-3, 4-dihydroxy-4-methyl-tetrahydrofuran-2-yl)methoxy)(phenoxy)phosphorylamino)-3-methylbutanoate (Scheme D-1)

Step 1: To a solution of POCl₃ (10 mL, 107 mmol) in CH₂Cl₂ (30 mL) at −50° C. (dry ice/acetone) was added a solution of phenol (2.86 g, 30.3 mmol) and Et₃N (4.25 mL, 30.4 mmol) in CH₂Cl₂ (25 mL) over a period of 15 min. The temperature was allowed to go to 10° C. over a period of 1.5 h and stirred at room temperature overnight. The white solid was removed by filtration under nitrogen atmosphere and the filtrate was evaporated to dryness. To the residue, Et₂O (20 mL) was added and the white solid was removed again by filtration. The concentration of the filtrate provided 8.1 g of phenyl phosphorodichloridate, which was used as such for the next step.

Step 2: To a solution of L-valine-methyl ester hydrochloride (2.4 g, 14.36 mmol) and phenyl phosphorodichloridates from Step 1 (3.02 g) in CH₂Cl₂ (60 mL) at −78° C. (dry ice/acetone) was added a solution of Et₃N (4.02 mL, 28.72 mmol) in CH₂Cl₂ (20 mL) over a period of 30 min. The reaction mixture was further stirred at −50 to −30° C. for 4.5 h and then evaporated to dryness. To the residue was added Et₂O (20 mL) and the white solid was removed under nitrogen. The filtrate was concentrated to give 3.0 g (68%) of phenyl methylvaline phosphorochloridate, which was used as such for the next step.

Step 3: To a solution of Example B-24 (63 mg, 0.225 mmol) and N-methyl imidazole (74 mg, 0.9 mmol) in THF (1 mL) was added a solution of phosphorochloridate from Step 2 (137 mg, 0.45 mmol) in THF (1 mL) at room temperature and the mixture was stirred for 4 h. Additional phosphorochloridate (137 mg, 0.45 mmol) and N-methyl imidazole (74 mg, 0.9 mmol) were added and stirred for 17 h at room temperature. The reaction mixture was concentrated and the residue was purified on a column of silica gel using 0 to 5% MeOH in CHCl₃ to give 28 mg (23%) of desired product as a white solid, mp 58-62° C.

¹H NMR (DMSO-d₆): 8.23 (s, 1H), 8.08 (s, 1H), 7.00-7.40 (m, 7H), 5.85-6.00 (m, 1H), 5.17 (brs, 1H, D₂O exchangeable), 4.99 and 4.97 (2s, 1H), 4.89 (brs, 1H, D₂O exchangeable), 3.92-4.35 (m, 3H), 3.66 and 3.57 (2s, 3H), 3.33-3.68 (m, 2H), 1.78-1.96 (m, 1H), 0.92 (s, 3H), 0.80 (d, J=6.8 Hz, 3H) and 0.73 (d, J=6.8 Hz, 3H); IR (KBr) 3341, 3205, 2965, 1739, 1653, 1491, cm⁻¹; MS (ES⁺) 573.30 (M+Na); Anal. Calcd for C₂₄H₃₁N₄O₉P.2H₂O: C, 49.14; H, 6.01; N, 9.55. Found: C, 49.24; H, 5.78; N, 9.33.

Example D-2

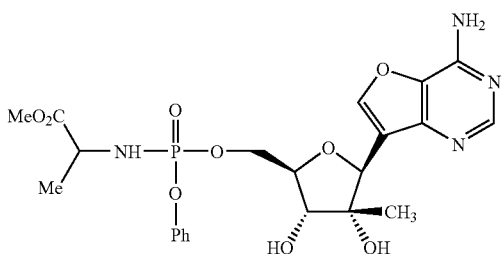

Methyl 2-(((5-(4-Aminofuro[3,2-d]pyrimidin-7-yl)-3,4-dihydroxy-4-methyl-tetrahydrofuran-2-yl)methoxy)(phenoxy)phosphorylamino)propanoate (Scheme D-1)

This compound was prepared the same way as Example D-1 except that L-alanine-methyl ester hydrochloride was used in this preparation instead of L-valine-methyl ester hydrochloride, yield (48%).

$^1$H NMR (DMSO-$d_6$): 8.24 and 8.23 (2s, 1H, for both isomers), 8.08 and 8.07 (2s, 1H, both isomers), 7.10-7.40 (m, 7H, ArH and NH$_2$), 5.94-6.00 (m, 1H), 5.14-5.20 (m, 1H), 4.96 and 4.99 (2s, 1H), 4.90 (s, 1H), 4.14-4.35 (m, 2H), 3.94-4.02 (m, 2H), 3.78-3.89 (m, 1H), 3.52 and 3.56 (2s, 3H), 1.15 and 1.23 (2d, J=7.34 and 6.94 Hz, 3H), 0.92 (s, 3H); IR (KBr): 3335, 3201, 1741, 1653, 1489, 1213, 935 cm$^{-1}$; MS (ES$^+$) 545.28 (M+Na); Anal. Calcd for C$_{22}$H$_{27}$N$_4$O$_9$P·0.75H$_2$O: C, 49.30; H, 5.35; N, 10.45. Found: C, 49.51; H, 5.18; N, 9.94.

Example D-3

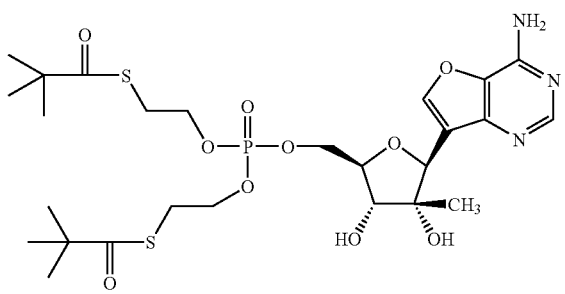

S,S'-2,2'-(((5-(4-Aminofuro[3,2-d]pyrimidin-7-yl)-3,4-dihydroxy-4-methyl-tetrahydrofuran-2-yl)methoxy)phosphoryl)bis(oxy)bis(ethane-2,1-diyl)bis(2,2-dimethylpropanethioate) (Scheme D-2)

To a solution of Example B-24 (0.16 g, 0.6 mmol) in THF (20 mL) at 0° C. were added tetrazole (120 mg, 1.8 mmol) and 2,2-dimethyl-thiopropionic acid S-{diisopropylamino-[2-(2,2-dimethyl-propionylsulfanyl)-ethoxy]-phosphanyloxymethyl} ester (0.51 g, 1.2 mmol) dropwise followed by stirring for 2 h at room temperature. After the reaction mixture was cooled to −40° C., 70% m-chloroperbenzoic acid (0.27 g, 0.7 mmol) was added and the reaction was allowed to warm to room temperature and was quenched by the addition of aqueous 10% sodium sulfite (3 mL) and diluted with CHCl$_3$ (20 mL). The organic layer was washed with water (20 mL), aqueous saturated sodium bicarbonate solution (2×20 mL) and dried over MgSO$_4$. After filtration, the filtrate was concentrated and the residue was purified on a silica gel column using 0 to 10% MeOH in chloroform as eluent to give 90 mg (20%) of desired product.

$^1$H NMR (DMSO-$d_6$ δ in ppm) 8.25 (s, 1H), 8.15 (s, 1H), 7.40 (br s, 2H), 5.20 (m, 1H), 4.90 (m, 2H), 4.20 (m, 2H), 4.00 (m, 6H), 3.10 (m, 4H), 1.15 (m, 18H), 0.90 (s, 3H); $^{31}$P NMR 0.68 ppm; MS (ES$^+$) 650.32 (M+H)$^+$; Anal. Calcd for C$_{26}$H$_{40}$N$_3$O$_{10}$PS$_2$: C, 48.05; H, 6.20; N, 6.47. Found: C, 48.02; H, 6.37; N, 6.23.

Example D-4

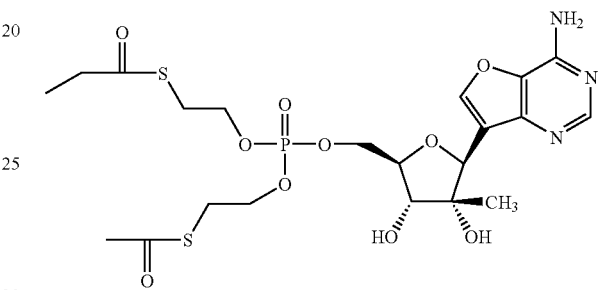

S,S'-2,2'-(((5-(4-Aminofuro[3,2-d]pyrimidin-7-yl)-3,4-dihydroxy-4-methyl-tetrahydrofuran-2-yl)methoxy)phosphoryl)bis(oxy)bis(ethane-2,1-diyl)diethanethioate (Scheme D-2)

This compound was prepared the same way as Example D-3 using, compound from Example B-24 and thioacetic acid S-{2-[(2-acetylsulfanyl-ethoxy)-diisopropylaminophosphanyloxy]-ethyl} ester, yield 8.6 mg (3%).

$^1$H NMR (DMSO-$d_6$ δ in ppm) 8.26 (s, 1H), 8.12 (s, 1H), 7.35 (br s, 2H), 5.20 (m, 1H), 4.95 (m, 2H), 4.30 (m, 2H), 4.00 (m, 6H), 3.20 (m, 4H), 2.30 (m, 6H), 0.90 (s, 3H); $^{31}$P NMR 0.61 ppm; MS (ES$^+$) 566.28 (M+H)$^+$.

Example D-5

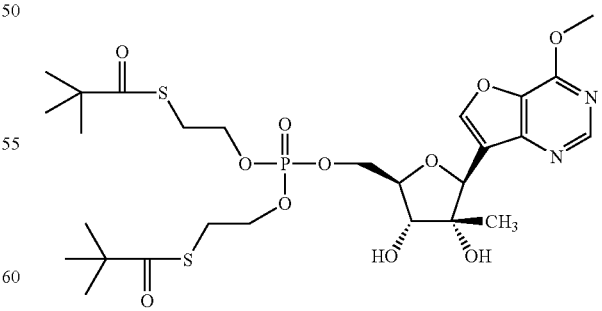

S,S'-2,2'-(((3,4-Dihydroxy-5-(4-methoxyfuro[3,2-d]pyrimidin-7-yl)-4-methyl-tetrahydrofuran-2-yl)methoxy)phosphoryl)bis(oxy)bis(ethane-2,1-diyl)bis(2,2-dimethylpropanethioate) (Scheme D-2)

This compound was prepared the same way as Example D-3 using compound from Example B-13 and 2,2-dimethyl-thiopropionic acid S-{diisopropylamino-[2-(2,2-dimethyl-propionylsulfanyl)-ethoxy]-phosphanyloxymethyl} ester, yield 15 mg (13%).

$^1$H NMR (CDCl$_3$ δ in ppm) 8.60 (s, 1H), 7.90 (s, 1H), 5.20 (m, 1H), 4.40 (m, 3H), 4.25 (s, 3H), 4.20 (m, 6H), 3.90 (m, 1H), 3.20 (m, 4H), 1.20 (m, 18H), 1.00 (s, 3H); $^{31}$P NMR 0.0 ppm; MS (ES$^+$) 665.28 (M+H)$^+$, MS (ES$^-$) (M+Cl)$^-$ 699.19.

Example D-6

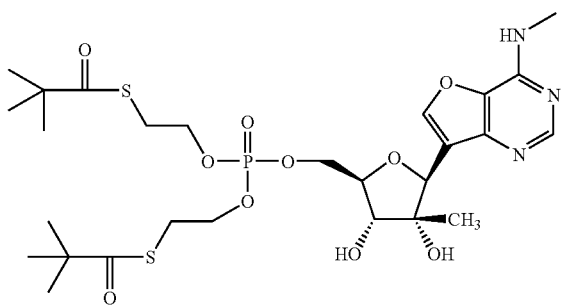

S,S'-2,2'-(((3,4-Dihydroxy-4-methyl-5-(4-(methylamino)furo[3,2-d]pyrimidin-7-yl)-tetrahydrofuran-2-yl)methoxy)phosphoryl)bis(oxy)bis(ethane-2,1-diyl)bis(2,2-dimethylpropanethioate) (Scheme D-2)

This compound was prepared the same way as Example D-3 using compound from Example B-17 and 2,2-dimethyl-thiopropionic acid S-{diisopropylamino-[2-(2,2-dimethyl-propionylsulfanyl)-ethoxy]-phosphanyloxymethyl}ester, yield 107 mg (48%).

$^1$H NMR (DMSO-d$_6$ δ in ppm) 8.35 (s, 1H), 8.00 (s, 1H), 7.80 (br s, 1H), 5.20 (d, J=6.5 Hz, 1H), 4.97 (m, 1H), 4.90 (m, 1H), 4.26 (m, 2H), 3.99 (m, 6H), 3.00 (m, 4H), 2.96 (m, 3H), 1.14 (m, 18H), 0.91 (s, 3H); $^{31}$p NMR 0.60 ppm; MS (ES$^+$) 686.27 (M+Na)$^+$, MS (ES$^-$) (M-H)$^-$ 662.30; Anal. Calcd for C$_{27}$H$_{42}$N$_3$O$_{10}$PS$_2$: C, 47.24; H, 6.54; N, 6.12. Found: C, 47.16; H, 6.27; N, 6.10.

Example D-7

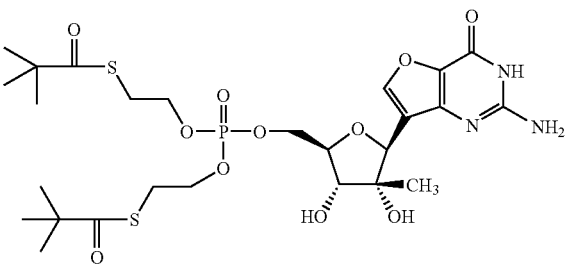

S,S'-2,2'-((5-(2-Amino-4-oxo-3,4-dihydrofuro[3,2-d]pyrimidin-7-yl)-3,4-dihydroxy-4-methyl-tetrahydrofuran-2-yl)methoxy)phosphoryl)-bis(oxy)bis(ethane-2,1-diyl)bis(2,2-dimethylpropanethioate) (Scheme D-2)

This compound was prepared the same way as Example D-3 using compound from Example B-21 and 2,2-dimethyl-thiopropionic acid S-{diisopropylamino-[2-(2,2-dimethyl-propionylsulfanyl)-ethoxy]-phosphanyloxymethyl}ester, yield 28 mg (33%).

$^1$H NMR (DMSO-d$_6$ δ in ppm) 10.90 (br s, 1H), 7.80 (s, 1H), 6.30 (br s, 2H), 5.12 (m, 1H), 4.80 (m, 2H), 4.20 (m, 2H), 4.00 (m, 4H), 3.80 (m, 2H), 3.00 (m, 4H), 1.12 (m, 18H), 0.91 (s, 3H); $^{31}$P NMR 0.50 ppm; MS (ES$^+$) 666.36 (M+H)$^+$, MS (ES$^-$) (M-H)$^-$ 664.33.

Example D-8

The following illustrate representative pharmaceutical dosage forms, containing a compound of formula I, II, or III, or a pharmaceutically acceptable salt or prodrug thereof ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution | q.s. |

| -continued | |
|---|---|
| (pH adjustment to 7.0-7.5) Water for injection | q.s. ad 1 mL |
| (vi) Aerosol | mg/can |
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed:

1. The compound 4-Amino-7-β-(2'-C-methyl-D-ribofuranosyl)-furo[3,2-d]pyrimidine; or a pharmaceutically acceptable salt or prodrug thereof.

2. The compound of claim 1 which is a prodrug.

3. The compound of claim 2 which comprises one or more mono-, di-, or tri-phosphate groups.

4. The compound of claim 2 which comprises one or more mono-phosphate groups.

5. The compound of claim 3 wherein one or more pendent hydroxyl groups from the mono-, di-, or tri-phosphate group has been converted to an alkoxy, substituted alkoxy, aryloxy, or substituted aryloxy group.

6. The compound of claim 3 wherein one or more pendent hydroxyl groups from the mono-, di-, or tri-phosphate group has been converted to a group $R_y$—O—; wherein each $R_y$ is independently a 1-20 carbon branched or unbranched, saturated or unsaturated chain, wherein one or more of the carbon atoms is optionally replaced with —O— or —S— and wherein one or more of the carbon atoms is optionally substituted with oxo (=O) or thioxo (=S).

7. The compound of claim 3 wherein one or more pendent hydroxyl groups from the mono-, di-, or tri-phosphate group has been converted to a group $R_z$—N—; wherein each $R_z$ is a residue of an amino acid.

8. The compound of claim 7 wherein the amino acid is a natural amino acid.

9. The compound of claim 3 which comprises one or more groups of formula:

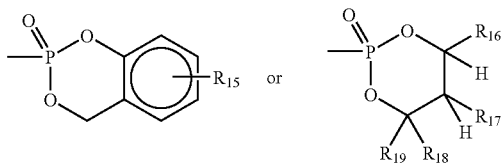

wherein:

$R_{15}$ is H, alkyl, substituted alkyl, aryl, substituted aryl, cycloalkyl, substituted cycloalkyl, heteroaryl, substituted heteroaryl, heterocyclic, substituted heterocyclic, or an amino acid;

$R_{16}$ is H, optionally substituted monocyclic aryl, or optionally substituted monocyclic heteroaryl; and $R_{17}$ is H, halogen, CN, —CO—$R_{20}$, —CON($R_{21}$)$_2$, —CO$_2R_{20}$, —SO$_2R_{20}$, —SO$_2$N($R_{21}$)$_2$, —OR$_{21}$, —SR$_{21}$, —R$_{21}$, —N($R_{21}$)$_2$, —O—COR$_{20}$, —O—CO$_2R_{20}$, —SCOR$_{20}$, —S—CO$_2R_{20}$, —NHCOR$_{21}$, —NHCO$_2R_{21}$, —(CH$_2$)$_p$—OR$_{22}$, or —(CH$_2$)$_p$—SR$_{22}$; or $R_{16}$ and $R_{17}$ are connected via an additional 3-5 atoms to form a cyclic group, optionally containing one heteroatom, that is fused to an aryl group at the beta and gamma position to the O attached to the phosphorus; or $R_{17}$ and $R_{18}$ are connected as described below;

$R_{18}$ and $R_{19}$ are each independently H, alkyl, aryl, heterocycloalkyl, aralkyl, optionally substituted monocyclic aryl or optionally substituted monocyclic heteroaryl; or $R_{18}$ and $R_{19}$ are connected via an additional 2-5 atoms to form a cyclic group, optionally containing 0-2 heteroatoms; or $R_{17}$ and $R_{18}$ are connected via an additional 3-5 atoms to form a cyclic group, optionally containing one heteroatom and $R_{19}$ is H, alkyl, aryl, heterocycloalkyl, aralkyl, optionally substituted monocyclic aryl or optionally substituted monocyclic heteroaryl;

$R_{20}$ is alkyl, aryl, heterocycloalkyl, or arylalkyl;

$R_{21}$ is H, alkyl, aryl, heterocycloalkyl, or arylalkyl;

$R_{22}$ is H or lower acyl;

n is an integer from 2-5;

m is an integer from 10-20; and p is an integer from 2-3.

10. A pharmaceutical composition comprising a compound as described in claim 1; or a pharmaceutically acceptable salt or prodrug thereof and a pharmaceutically acceptable carrier.

11. The composition of claim 10 which further comprises one or more additional anti-viral agents.

12. The composition of claim 11 wherein the one or more anti-viral agents are selected from ribavirin, levovirin, viramidine, thymosin alpha-1, an inhibitor of a serine proteases, an inhibitor of inosine monophosphatedehydrognease, interferon-α, and pegylated interferon-α (peginterferon-α).

13. The composition of claim 10 which further comprises one or more additional HCV polymerase inhibitors.

14. The composition of claim 10 which further comprises one or more protease inhibitors.

15. The composition of claim 10 which further comprises ribavirin.

16. The composition of claim 10 which further comprises interferon-α or pegylated interferon-α (peginterferon-α).

* * * * *